United States Patent
Hickey et al.

[11] Patent Number: 5,990,102
[45] Date of Patent: Nov. 23, 1999

[54] SUBSTITUTED AZETIDIN-2-ONES FOR TREATMENT OF ATHEROSCLEROSIS

[75] Inventors: Deirdre Mary Bernadette Hickey, Saffron Walden, United Kingdom; Dashyant Dhanak, West Chester, Pa.; Colin Andrew Leach; Robert John Ife, both of Hertfordshire, United Kingdom; David Graham Tew, Audubon, Pa.

[73] Assignee: SmithKline Beecham p.l.c., Brentford, United Kingdom

[21] Appl. No.: 08/860,162

[22] PCT Filed: Dec. 20, 1995

[86] PCT No.: PCT/EP95/05130

§ 371 Date: Nov. 21, 1997

§ 102(e) Date: Nov. 21, 1997

[87] PCT Pub. No.: WO96/19451

PCT Pub. Date: Jun. 27, 1996

[30] Foreign Application Priority Data

| Dec. 22, 1994 | [GB] | United Kingdom | 9426020 |
| Dec. 22, 1994 | [GB] | United Kingdom | 9426030 |
| Jun. 8, 1995 | [GB] | United Kingdom | 9511599 |
| Jun. 8, 1995 | [GB] | United Kingdom | 9511600 |

[51] Int. Cl.[6] ........................ A61K 31/395; C07D 205/09
[52] U.S. Cl. .............................................. 514/210; 540/360
[58] Field of Search ............................. 540/360; 514/210

[56] References Cited

FOREIGN PATENT DOCUMENTS

| 010358 | 4/1980 | European Pat. Off. . |
| 199630 | of 1986 | European Pat. Off. . |
| 481671 | of 1992 | European Pat. Off. . |

OTHER PUBLICATIONS

Kita et al., Tetrahedron Letters, 36(1) , pp. 115–118 (1995).

Kita et al., Chemical & Pharmaceutical Bulletin, 39(9), pp. 2225–2232 (1991).

Kametani, Chem Abs 109:6266, 1988.

Ihara, Tetrahedron, vol. 38, 2489, 1982.

*Primary Examiner*—Mark L. Berch
*Attorney, Agent, or Firm*—Wayne J. Dustman; William T. King; Charles M. Kinzig

[57] ABSTRACT

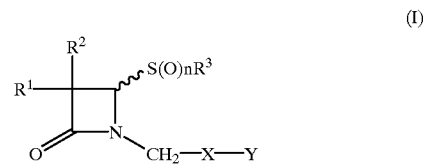

Compounds of formula (I) in which $R^1$ and $R^2$, which may be the same or different, is each selected from hydrogen, halogen or $C_{(1-8)}$alkyl; $R^3$ is aryl or aryl $C_{(1-4)}$alkyl which may be optionally substituted; X is a linker group; Y is an optionally substituted aryl group; and n is 0, 1 or 2; are inhibitors of the enzyme $Lp\text{-}PLA_2$ and thereof of use in treating atherosclerosis.

21 Claims, No Drawings

SUBSTITUTED AZETIDIN-2-ONES FOR TREATMENT OF ATHEROSCLEROSIS

This application is a 371 application of International Application PCT/EP95/05130, filed on Dec. 20, 1995.

The present invention relates to certain novel monocyclic β-lactam compounds, processes for their preparation, intermediates useful in their preparation, pharmaceutical compositions containing them and their use in therapy, in particular in the treatment of artherosclerosis.

Lipoprotein Associated Phospholipase $A_2$ (Lp-$PLA_2$). The sequence of the enzyme, the isolation and purification thereof, isolated nucleic acids encoding the enzyme, recombinant host cells transformed with DNA encoding the enzyme are described in patent application WO 95/00649 (SmithKline Beecham plc). Suggested therapeutic uses for inhibitors of the enzyme included artherosclerosis, diabetes, rheumatoid arthritis, stroke, myocardial infarction, reperfusion injury and acute and chronic inflammation. A later patent application (WO 95/09921, Icos Corporation) and a related publication in Nature (Tjoelker et al, vol 374, Apr. 6, 1995, 549) describe the same enzyme, although calling it by the name 'Platelet Activating Factor Acetyl Hydrolase' (PAF acetyl hydrolase) and suggest that it may have potential as a therapeutic protein for regulating pathological inflammatory events.

Lp-$PLA_2$ is responsible for the conversion of phosphatidylcholine to lysophosphatidylcholine, during the conversion of low density lipoprotein (LDL) to its oxidised form. The enzyme is known to hydrolyse the sn-2 ester of oxidised phosphatidylcholine to give lysophosphatidylcholine and an oxidatively modified fatty acid. Both products of Lp-$PLA_2$ action are biologically active with lysophosphatidylcholine, a component of oxidised LDL, known to be a potent chemoattractant for circulating monocytes. As such, lysophosphatidylcholine is thought play a significant role in atherosclerosis by being responsible for the accumulation of cells loaded with cholesterol ester in the arteries. Inhibition of the Lp-$PLA_2$ enzyme would therefore be expected to stop the build up of these macrophage enriched lesions (by inhibition of the formation of lysophosphatidylcholine and oxidised free fatty acids) and so be useful in the treatment of atherosclerosis.

The increased lysophosphatidylcholine content of oxidatively modified LDL is also thought to be responsible for the endothelial dysfunction observed in patients with atherosclerosis. Inhibitors of Lp-$PLA_2$ could therefore prove beneficial in the treatment of this phenomenon. A Lp-$PLA_2$ inhibitor could also find utility in other disease states that exhibit endothelial dysfunction including diabetes, hypertension, angina pectoris and after ischaemia and reperfusion.

Lp-$PLA_2$ inhibitors may also have a general application in any disorder that involves activated monocytes, macrophages or lymphocytes, as all of these cell types express Lp-PLA. Examples of such disorders include psoriasis.

Lp-$PLA_2$ inhibitors may also have a general application in any disorder that involves lipid peroxidation in conjunction with Lp-$PLA_2$ activity to produce the two injurious products, lysophosphatidylcholine and oxidatively modified fatty acids. Such conditions include the aforementioned conditions atherosclerosis, diabetes, rheumatoid arthritis, stroke, inflammatory conditions of the brain such as Alzheimer's Disease, myocardial infarction, reperfusion injury, sepsis and acute and chronic inflammation. Further such conditions include various neuropsychiatric disorders such as schizophrenia (see Psychopharmacology Bulletin, 31, 159–165, 1995).

We have now identified a series of compounds which have been found to act as inhibitors of Lp-$PLA_2$.

Accordingly, the present invention provides a compound of formula (I):

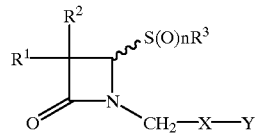

(I)

in which:

$R^1$ and $R^2$, which may be the same or different, is each selected from hydrogen, halogen or optionally substituted $C_{(1-8)}$alkyl;

$R^3$ is aryl or aryl $C_{(1-4)}$alkyl which may be optionally substituted;

X is a linker group;

Y is an optionally substituted aryl group; and n is 0, 1 or 2.

Compounds of formula (I) are inhibitors of Lp-$PLA_2$ and as such are expected to be of use in treating atherosclerosis and the other disease conditions noted above.

Representative examples of $R^1$ and $R^2$ include hydrogen, bromo, methyl and ethyl, optionally substituted with hyroxyl. Suitably, $R^1$ and $R^2$ is each hydrogen or one of $R^1$ and $R^2$ is hydrogen and the other of $R^1$ and $R^2$ is methyl (to give a trans-methyl). Preferably, $R^1$ and $R^2$ is each hydrogen.

Within $R^3$, representative examples of the aryl group include phenyl and naphthyl. Suitably, $R^3$ is aryl $C_{(1-3)}$alkyl. Suitable examples of $R^3$ include phenyl, benzyl, 2-phenylethyl and 3-phenylpropyl in each of which the phenyl ring may be optionally substituted by up to three substituents. It will be appreciated that an optional substituent may be located in the aryl portion and/or the alkyl portion (if present). Preferably, $R^3$ is optionally substituted benzyl, preferably substituted at the 4-position. Suitable substituents for a phenyl or naphthyl ring in $R^3$ include halo, hydroxy, $C_{(1-6)}$alkyl, $C_{(1-6)}$alkoxy, carboxy, $C_{(1-6)}$alkoxycarbonyl, $C_{(2-6)}$alkenyloxycarbonyl, carboxy $C_{(1-6)}$alkyl and $C_{(1-6)}$alkoxy-carbonyl $C_{(1-6)}$alkyl. More preferably, $R^3$ is 4-carboxybenzyl or a corresponding $C_{(1-6)}$alkyl or $C_{(2-6)}$ alkenyl ester thereof.

Preferably, n is 1 or 2 more preferably 1.

Preferably, $S(O)_nR^3$ is optionally substituted benzylsulphinyl, more preferably 4-carboxybenzylsulphinyl or a corresponding $C_{(1-6)}$alkyl or $C_{(2-6)}$alkenyl ester thereof.

Suitably X is a direct bond; a group $X'(CH_2)_m$ in which X' is CO, $CONR^5$, COO, $CONR^5CO$, or CONHO in which $R^5$ is hydrogen or $C_{(1-6)}$alkyl and m is 0 or an integer from 1 to 12; or a $C_{(1-12)}$alkylene chain optionally interupted by X'. Representative examples of X include $CO(CH_2)_m$, CONH $(CH_2)_m$, $COO(CH_2)_m$, $CONHCO(CH_2)_m$, $CONHO(CH_2)_m$ and $C_{(1-12)}$alkylene. Preferably, X' is CO or $CONR^5$, more preferably CONH. Preferably, m is 1, 2, 5, 6, 7 or 9, preferably 6. Preferably, X is $CONH(CH_2)_6$.

Suitably, Y is a benzene ring, optionally substituted by up to three further substituents. Suitable substituents include halo, hydroxy, $C_{(1-8)}$alkyl and $C_{(1-8)}$alkoxy. Preferably, Y is phenyl optionally substituted by halo, more preferably 4-chloro or 4-fluoro-phenyl, most preferably, 4-fluoro-phenyl.

It will be readily appreciated by the skilled person that C-4 of the β-lactam ring is a chiral centre which will give rise to the presence of stereoisomers. The present invention encompasses all such stereoisomers.

It will be further readily appreciated by the skilled person that, in compounds of formula (I) in which n is 1, that is sulphoxide compounds, the presence of the SO moiety will introduce an additional chiral centre into the molecule and therefore give rise to the existence of extra stereoisomers. The present invention encompasses all such stereoisomers.

In preferred compounds of formula (I), the relative configurations at C-4 and the SO moiety are R,S and S,R and in the most preferred compounds the absolute configurations at C-4 and the SO moiety are R and S respectively.

When used herein, the term 'alkyl' and similar terms such as 'alkoxy' includes all straight chain and branched isomers. Representative examples thereof include methyl, ethyl, n-propyl, iso-propyl, n-butyl, sec-butyl, iso-butyl, t-butyl, n-pentyl and n-hexyl.

Suitable substituents for an alkyl group include, for example, halogen, cyano, azido, nitro, carboxy, $(C_{1-6})$ alkoxycarbonyl, carbamoyl, mono- or di-$(C_{1-6})$ alkylcarbamoyl, sulpho, sulphamoyl, mono- or di-$(C_{1-6})$ alkylsulphamoyl, amino, mono- or di-$(C_{1-6})$alkylamino, acylamino, ureido, $(C_{1-6})$alkoxycarbonylamino, 2,2,2-trichloroethoxycarbonylamino, aryl, heterocyclyl, hydroxy, $(C_{1-6})$alkoxy, acyloxy, oxo, acyl, 2-thienoyl, $(C_{1-6})$alkylthio, $(C_{1-6})$alkylsulphinyl, $(C_{1-6})$alkylsulphonyl, hydroxyimino, $(C_{1-6})$alkoxyimino, hydrazino, hydrazono, benzohydroximoyl, guanaidino, amindino and iminoalkylamino.

When used herein, the term 'aryl' includes, unless otherwise defined, phenyl or naphthyl optionally substituted with up to five, preferably up to three substituents.

Suitable substituents for an aryl group include, for example, halogen, cyano, $(C_{1-6})$alkyl, $(C_{3-7})$cycloalkyl, $(C_{1-6})$alkoxy, halo$(C_{1-6})$alkyl, hydroxy, amino, mono- or di-$(C_{1-6})$alkylamino, acylamino, nitro, carboxy, $(C_{1-6})$ alkoxycarbonyl, $(C_{2-6})$alkenyloxycarbonyl, $(C_{1-6})$ alkoxycarbonyl$(C_{1-6})$alkyl, $(C_{2-6})$alkenoxycarbonyl$(C_{1-6})$ alkyl, $(C_{1-6})$alkylcarbonyloxy, carboxy$(C_{1-6})$alkoxy, $(C_{1-6})$ alkoxycarbonyl$(C_{1-6})$alkoxy, $(C_{2-6})$alkenoxycarbonyl$(C_{1-6})$ alkoxy, $(C_{1-6})$alkylcarbonyloxy, $(C_{1-6})$alkylthio, $(C_{1-6})$ alkylsulphinyl, $(C_{1-6})$alkylsulphonyl, sulphamoyl, mono- and di-$(C_{1-6})$-alkylsulphamoyl, carbamoyl, mono- and di-$(C_{1-6})$alkylcarbamoyl, and heterocyclyl.

When used herein, the terms 'halogen' and 'halo' include fluorine, chlorine, bromine and iodine and fluoro, chloro, bromo and iodo, respectively.

Preferred compounds of formula (I) include:
(4R,SS/4S,SR)-N-(6-phenylhexyl)-(4-(4-methoxyphenyl)sulfinyl)-2-oxoazetidin-1-yl)acetamide;
(4R,SS/4S,SR)-N-(6-phenylhexyl)-(4-(3,4-dimethoxyphenylsulfinyl)-2-oxoazetidin-1-yl)acetamide;
(4R,SR/4S,SS) N-(6-phenylhexyl)-(4-(3,4-dimethoxyphenylsulfinyl)-2-oxoazetidin-1-yl)acetamide;
(4R,SS/4S,SR)-4-(Phenylsulphinyl)-N-(4-phenyl-2-oxobutyl)azetidin-2-one;
(4R,SS)-4-(Phenylsulphinyl)-N-(4-phenyl-2-oxobutyl) azetidin-2-one;
(4R,SS/4S,SR)-4-(3,4-dimethoxyphenylsulphinyl)-N-(4-phenyl-2-oxobutyl)azetidin-2-one;
(4R,SS/4S,SR)-4-(3-methoxyphenylsulphinyl)-N-(4-phenyl-2-oxobutyl)azetidin-2-one;
(4R,SS/4S,SR)-4-(4-methoxyphenylsulphinyl)-N-(4-phenyl-2-oxobutyl)azetidin-2-one;
(R,S/S,R)-N-[6-(4-chlororophenyl)hexyl]-4-(4-methylphenyl)sulfinyl-2-oxo-azetidinyl-1-yl acetamide;
(R,S/S,R)-N-[6-(4-Chlorophenyl)hexyl]-4-phenylsulfinyl-2-oxoazetidin-1-ylacetamide;
(+)-(R,S or S,R)-N-[6-(4-Chlorophenyl)hexyl]-4-phenylsulfinyl-2-oxoazetidin-1-ylacetamide;
(−)-(R,R or S,S)-N-[6-(4-Chlorophenyl)hexyl]-4-phenylsulfinyl-2-oxoazetidin-1-ylacetamide;
(R,S/S,R)-N-[6-(4-Chlorophenyl)hexyl]-4-(4-methoxyphenylsulfinyl)-2-oxoazetidin-1-ylacetamide;
N-(6-{4-Fluorophenyl}hexyl)-4-(4-allyloxycarbonylbenzylsulphinyl-2-oxoazetidin-1-yl(acetamide (Diastereoisomer 2);
N-(6-{4-Fluorophenyl}hexyl)-4-(4-carboxybenzylsulphinyl-2-oxoazetidin-1-yl)acetamide (Diastereoisomer 2);
N-(6-{4-Fluorophenyl}hexyl)-4-(4-isopropyloxycarbonylbenzylsulphinyl-2-oxoazetidin-1-yl)acetamide (Diastereoisomer 2);
N-(6-{4-Fluorophenyl}hexyl)-4-(4-propyloxycarbonylbenzylsulphinyl-2-oxoazetidin-1-yl)acetamide (Diastereoisomer 2);
N-[6-(4-Fluorophenyl)hexyl]-[4-(4-ethyloxycarbonylbenzyl)sulphinyl]-2-oxo-azetidin-1-yl]-acetamide (Diastereoisomer 2);N-(6-[4-Fluorophenyl] hex-1-yl)-4-carboxybenzylthio)-2-oxoazetidin-1-yl acetamide;
N-[6-(4-Fluorophenyl)hexyl]-[4-(4-methyloxycarbonylbenzyl)sulphinyl-2-oxo-azetidin-1-yl]-acetamide (Diastereoisomer 2);
N-(6-{4-Chlorophenyl}hexyl)-4-(4-isopropyloxycarbonylbenzylsulphinyl-2-oxoazetidin-1-yl)acetamide (Diastereoisomer 2);
N-(6-{4-Chlorophenyl}hexyl)-4-(4-propyloxycarbonylbenzylsulphinyl-2-oxoazetidin-1-yl) acetamide (Diastereoisomer 2);
N-(6-{4-Chlorophenyl}hexyl)-4-(4-ethyloxycarbonylbenzylsulphinyl-2-oxoazetidin-1-yl) acetamide (Diastereoisomer 2);
N-[6-(4-Fluorophenyl)hexyl]-[4-(4-allyloxycarbonylmethyl)benzyl)sulphinyl-2-oxo-azetidin-1-yl]-acetamide (Diastereomer 2);
N-[6-(4-Fluorophenyl)hexyl]-[4-(4-(carboxymethyl)benzyl)sulphinyl-2-oxo-azetidin-1-yl]-acetamide (Diastereomer 2);
(4R,SS/4S,SR) 4-(Benzylsulphinyl)-1-(4-phenyl-2-oxobutyl)azetidin-2-one;
(4R,SS/4S,SR) 4-(Benzylsulphinyl)-1-(9-phenyl-2-oxononyl)azetidin-2-one;
(4R,SS/4S,SR) N-(6-phenylhexyl)-(4-benzylsulphinyl-2-oxoazetidin-1-yl)acetamide;
(4R,SS/4S,SR) N-benzyl-(4-benzylsulphinyl-2-oxoazetidin-1-yl)acetamide;
(4R,SS/4S,SR) N-(9-Phenylnonyl)-(4-benzylsulphinyl-2-oxoazetidin-1-yl)acetamide;
(4R,SS/4S,SR) N-[6-(3,5-Di-tert-butyl-4-hydroxyphenyl) hexyl]-(4-benzylsulphinyl-2-oxoazetidin-1-yl)acetamide;
(4R,SR/4S,SS) N-6-(4-methoxyphenyl)hexyl-(4-benzylsulphinyl-2-oxoazetidin-1-yl)acetamide;
(4R,SS/4S,SR) N-6-(4-methoxyphenyl)hexyl-(4-benzylsulphinyl-2-oxoazetidin-1-yl)acetamide;
(4R,SS/4S,SR) N-(6-(4-chlorophenyl)hexyl)-(4-benzylsulphinyl-2-oxoazetidin-1-yl)acetamide;
(4R,SS) N-(6-(4-chlorophenyl)hexyl)-(4-benzylsulphinyl-2-oxoazetidin-1-yl)acetamide;
4R,SS/4S,SR) N-(6-(3,5-dichlorophenyl)hexyl)-(4-benzylsulphinyl-2-oxoazetidin-1-yl)acetamide;
(4R,SS/4S,SR) N-(6-(3-chlorophenyl)hexyl)-(4-benzylsulphinyl-2-oxoazetidin-1-yl)acetamide;
(4R,SS/4S,SR) N-(6-Phenylhexyl)-(4-(4-ethoxycarbonyl) benzylsulphinyl-2-oxoazetidin-1-yl)acetamide;

N-(6-(3,5-dichlorophenyl)hexyl)-(4-benzylsulphonyl-2-oxoazetidin-1-yl)acetamide;

(4R,SS/4S,SR) 4-Benzylsulphinyl-1-(2-phenethyl)azetidin-2-one;

(3S,4R,SR)-N-(6-phenylhexyl)-4-benzylsulphinyl-3-bromo-2-oxoazetidin-1-yl acetamide;

(3S,4R,SR)-N-(6-phenylhexyl)-4-benzylsulphinyl-3-bromo-2-oxoazetidin-1-yl acetamide;

N-(6-[4-chlorophenyl]hex-1-yl)-(4-carboxylbenzylsulphinyl)-2-oxoazetidin-1-yl acetamide (Diastereoisomer 2);

N-(6-[4-chlorophenyl]hex-1-yl)-(4-methoxycarbonylbenzylsulphinyl)-2-oxoazetidin-1-yl acetamide (Diastereoisomer 2);

N-(6-[4-chlorophenyl]hex-1-yl)-(4-allyloxycarbonyl-benzylsulphinyl)-2-oxoazetidin-1-yl acetamide (Diastereoisomer 2).

Since the compounds of the present invention, in particular compounds of formula (I), are intended for use in pharmaceutical compositions, it will be understood that they are each provided in substantially pure form, for example at least 50% pure, more suitably at least 75% pure and preferably at least 95% pure (% are on a wt/wt basis). Impure preparations of the compounds of formula (I) may be used for preparing the more pure forms used in the pharmaceutical compositions. Although the purity of intermediate compounds of the present invention is less critical, it will be readily understood that the substantially pure form is preferred as for the compounds of formula (I). Preferably, whenever possible, the compounds of the present invention are obtained in crystalline form.

When some of the compounds of this invention are allowed to crystallise or are recrystallised from organic solvents, solvent of crystallization may be present in the crystalline product. This invention includes within its scope such solvates. Similarly, some of the compounds of this invention may be crystallised or recrystallised from solvents containing water. In such cases water of hydration may be formed. This invention includes within its scope stoichiometric hydrates as well as compounds containing variable amounts of water that may be produced by processes such as lyophilisation. In addition, different crystallisation conditions may lead to the formation of different polymorphic forms of crystalline products. This invention includes within its scope all polymorphic forms of the compounds of formula (I).

Compounds of the present invention are inhibitors of the enzyme lipoprotein associated phospholipase $A_2$ (Lp-PLA$_2$) and as such are expected to be of use in therapy, in particular in the treatment of atherosclerosis. In a further aspect therefore the present invention provides a compound of formula (I) for use in therapy. The compounds of formula (I) are inhibitors of lysophosphatidylcholine production by Lp-LA$_2$ and may therefore also have a general application in any disorder that involves endothelial dysfunction, for example atherosclerosis, diabetes, hypertension, angina pectoris and after ischaemia and reperfusion. In addition, compounds of formula (I) may have a general application in any disorder that involves lipid peroxidation in conjunction with enzyme activity, for example in addition to conditions such as atherosclerosis and diabetes, other conditions such as rheumatoid arthritis, stroke, inflammatory conditions of the brain such as Alzheimer's Disease, myocardial infarction, reperfusion injury, sepsis, and acute and chronic inflammation. Further such conditions include various neuropsychiatric disorders such as schizophrenia (see Psychopharmacology Bulletin, 31, 159–165, 1995).

Further applications include any disorder that involves activated monocytes, macrophages or lymphocytes, as all of these cell types express Lp-PLA$_2$. Examples of such disorders include psoriasis.

Accordingly, in a further aspect, the present invention provides for a method of treating a disease state associated with activity of the enzyme Lp-PLA$_2$ which method involves treating a patient in need thereof with a therapeutically effective amount of an inhibitor of the enzyme. The disease state may be associated with the increased involvement of monocytes, macrophages or lymphocytes; with the formation of lysophosphatidylcholine and oxidised free fatty acids; with lipid peroxidation in conjunction with Lp PLA2 activity; or with endothelial dysfunction.

Compounds of the present invention may also be of use in treating the above mentioned disease states in combination with anti-hyperlipidaemic or anti-atherosclerotic or anti-diabetic or anti-anginal or anti-inflammatory or anti-hypertension agents. Examples of the above include cholesterol synthesis inhibitors such as stains, anti-oxidants such as probucol, insulin sensitisers, calcium channel antagonists, and anti-inflammatory drugs such as NSAIDs.

In therapeutic use, the compounds of the present invention are usually administered in a standard pharmaceutical composition. The present invention therefore provides, in a further aspect, a pharmaceutical composition comprising a compound of formula (I) and a pharmaceutically acceptable carrier.

Suitable pharmaceutical compositions include those which are adapted for oral or parenteral administration or as a suppository.

The compounds of formula (I) which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound of formula (I) in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

A typical suppository formulation comprises a compound of formula (I) which is active when administered in this way, with a binding and/or lubricating agent such as polymeric glycols, gelatins or cocoa butter or other low melting vegetable or synthetic waxes or fats.

Preferably the composition is in unit dose form such as a tablet or capsule.

Each dosage unit for oral administration contains preferably from 1 to 500 mg (and for parenteral administration contains preferably from 0.1 to 25 mg) of a compound of the formula (I).

The daily dosage regimen for an adult patient may be, for example, an oral dose of between 1 mg and 1000 mg, preferably between 1 mg and 500 mg, or an intravenous, subcutaneous, or intramuscular dose of between 0.1 mg and 100 mg, preferably between 0.1 mg and 25 mg, of the compound of the formula (I), the compound being administered 1 to 4 times per day. Suitably the compounds will be administered for a period of continuous therapy, for example for a week or more.

Compounds of formula (I) may be prepared from convenient starting materials by adapting synthetic procedures well known in the art. A suitable process comprises treating an azetidone of formula (II):

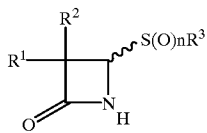

(II)

in which:

n, $R^1$, $R^2$ and $R^3$ are as hereinbefore defined; with an alkylating agent of the formula (III):

$$ZCH_2XY \qquad (III)$$

in which Z is a suitable leaving group such as halogen; and X and Y are as hereinbefore defined; under alkylating conditions.

Suitable alkylating conditions are well known to those skilled in the art and include the use of a suitable base such as sodium hydride or potassium hydroxide, in a suitable alkylating solvent such as tetrahydrofuran (THF), and at a temperature in the range −10 to 0° C. Suitably, alkylation is conveniently effected on compounds of formula (II) in which n is 0.

Compounds of formula (I) in which n is 1 or 2 can be readily prepared from compounds of formula (I) in which n is 0 by treatment thereof with a suitable oxidising agent such as m-chloroperbenzoic acid. Use of chiral oxidising agents such as (+)- or (−)-1,1'-bi-2-naphthol/titanium isopropoxide (N Komatsu et al, J Org Chem, 1993, 58, 7624–7626) can give diastereoisomeric selectivity, if not chirally pure compounds.

Compounds of formula (II) in which n is 0 may be obtained by treating 4-acetoxyazetidinone, 4-benzoyloxyazetidinone or 4-phenylsulfonylazetidinone with a thiol $R^3SH$ in the presence of a base such as sodium ethoxide, in a suitable solvent such as ethanol at a temperature in the range 0 to 5° C. When this displacement is conducted in the presence of a chiral base, such as chinchonidine or cinchonine, enantiomercially enriched compounds (II) can be obtained (Shibaski et al, JCS Chem. Commum. 1883, 1324).

Compounds of formula (III) may be readily prepared by adapting known synthetic procedures, according to the specific value of X. A convenient starting material is an appropriately substituted aryl compound which may then be elaborated to introduce the side chain $ZCH_xX$-.

Compounds of formula (I) in which X denotes a group $CONR_5(CH_2)_m$ (amide) or $CONHO(CH_2)_m$ (hydroxamate) may be conveniently prepared by treating an acid of the formula (IV):

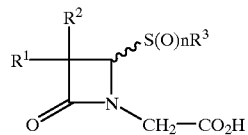

(IV)

in which:

n, $R^1$, $R^2$ and $R^3$ are as hereinbefore defined; with an amine of the formula (V):

$$NHR^5(CH_2)_mY \qquad (V)$$

or a hydroxylamine of the formula (VI):

$$NH_2O(CH_2)_mY \qquad (VI)$$

in which $R^5$, Y and m are as hereinbefore defined, under suitable amide or hydroxamate bond forming conditions (respectively).

Suitable such conditions are well known to those skilled in the art and include the use of an activating agent such as ethyl chloroformate or dicyclohexylcarbodiimide (DCC), in a suitable solvent such as chloroform or dimethyl formamide, at a temperature in the range −10 to 20° C.

An acid of formula (IV) may be obtained by treating a compound of formula (II) with a 2-bromoacetate ester, under alkylating conditions, as hereinbefore described; followed by the hydrolysis of the thus formed intermediate ester using standard conditions.

Compounds of formula (I) in which X denotes a group $COO(CH_2)_m$ (ester) may be conveniently prepared by transesterifying an ester of formula (VII):

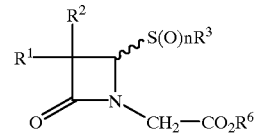

(VII)

in which: p1 $R^6$ is $(C_{1-6})$alkyl;

n, $R^1$, $R^2$ and $R^3$ are as hereinbefore defined; using transesterifying conditions.

Suitable such conditions are well known in the art and include, for instance, heating in toluene in the presence of a catalytic amount of sodium methoxide and an alcohol. Suitably, the compound of formula (VII) is a methyl ester in which $R^6$ is methyl.

A compound of formula (VII) may be obtained by treating a compound of formula (II) with an-alkyl 2-bromoacetate, under alkylating conditions, as hereinbefore described.

Compounds of formula (VII) are novel compounds which are useful as intermediates to compounds of formula (I).

Accordingly, in a further aspect, the present invention provides for compounds of formula (VII) as hereinbefore defined.

The compounds of formula (VII) are also inhibitors of the enzyme Lp-PLA$_2$ and therefore of use in the various diseases hereinbefore described for compounds of formula (I).

Alternatively, a compound of formula (I) in which X denotes a group $COO(CH_2)_m$ (ester) may be prepared by treating a compound of formula (IV) with an alcohol Y(CH$_2$)$_m$OH or an activated derivative thereof, for instance a tosylate.

In addition, compounds of formula (I) in which n is 0 may be prepared by a process which comprises treating a compound of formula (VIII):

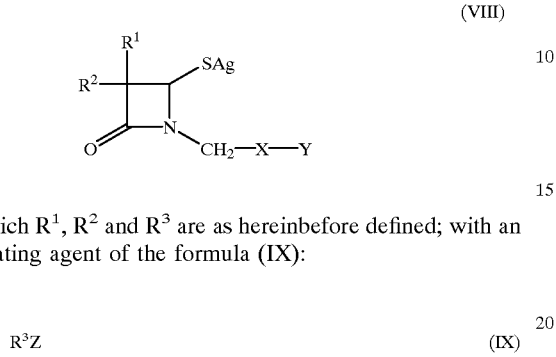

(VIII)

in which R$^1$, R$^2$ and R$^3$ are as hereinbefore defined; with an alkylating agent of the formula (IX):

R$^3$Z    (IX)

in which R$^3$ and Z are as hereinbefore defined; under suitable alkylating conditions, for instance, in a solvent such as acetonitrile, at a temperature in the region 25° C.

Compounds of formula (VIII) may be obtained from the corresponding 4-acetylthioazetidinone by treatment with silver nitrate and a base in a suitable solvent such as methanol.

Mixtures of diastereoisomeric compounds of formula (I) may be resolved, if so desired, according to procedures well known in the art. For instance sulphoxides (n=1) may be separated by chromatography and/or crystallisation. Chirally pure compounds may be prepared by chiral chromatography, from chirally pure intermediates or by chiral synthesis using chiral reagents or catalysis. Suitable chiral intermediates may be obtained by resolution or chiral induction or by using chiral reagents, in particular natural chiral molecules, according to methods well known to those skilled in the art. For chiral synthesis, a convenient chiral starting material is a penicillin derivative which has the preferred configuration at C-4 of the β-lactam ring. This is illustrated in the following scheme:

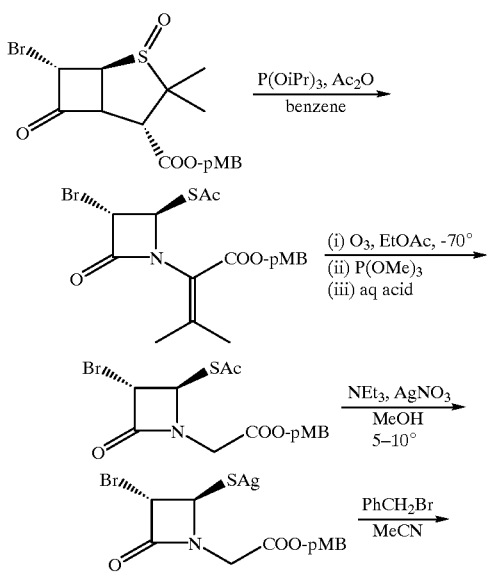

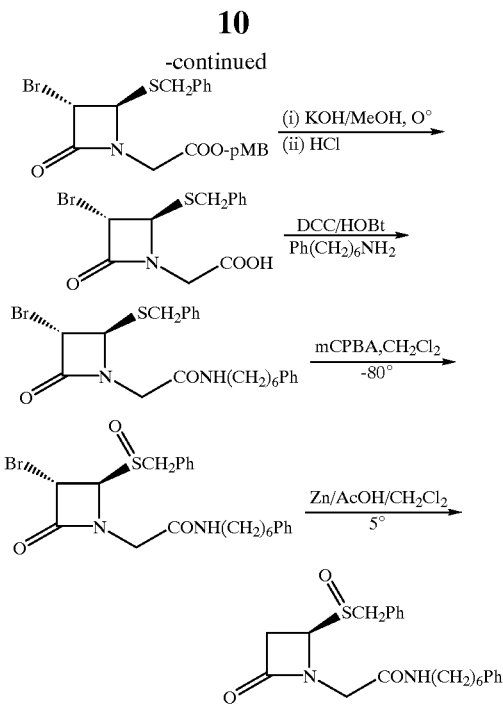

The preparation of the starting material (4-methoxybenzyl-6-bromopenicillinate-1-oxide) is described in J. Chem. Soc., Perkin Trans., 1, 1994, 179–188.

The present invention will not be illustrated by the following examples. In these examples diastereoisomers of sulfoxide compounds are referred to as having R,R/S,S or R,S/S,R configurations. Such configurations were obtained initially by x-ray analysis of a limited number of compounds and then extrapolated to the remaining compounds on the basis of their $^1$H NMR spectra. Unless otherwise specified, all compounds are racemic. Chiral compounds are described as 4R or S,SR or S where the 4 describes the centre at the C4 position in the azetidinone and the S describes the sulfoxide centre. Where mixtures of sulfoxides were obtained the spectral data is given for both (50:50 mixtures) or for the major isomer (e.g. 90:10 mixtures). All compounds are characterised by NMR and most by microanalysis and mass spec.

PREPARATIONS

Preparation 1

6-(4-Methoxyphenyl)hexylamine a. 6-Bromo-1-(4-methoxyphenyl)hexane

A solution of 6-bromohexanoyl chloride (50 g, 0.2 mol) in dry dichloromethane (40 ml) was added dropwise over 5 minutes to a suspension of aluminium chloride (31 g, 0.2 mol) in dry dichloromethane (100 ml), keeping the temperature between 20–23° C. The mixture was stirred for 30 minutes at room temperature to give a yellow solution. Anisole (23 g, 0.2 mol) in dry dichloromethane (30 ml) was added and stirred for 20 hours at room temperature. Triethylsilane (59.9 g, 0.515 mol) was added over 10 minutes, maintaining the temperature between 25° C.–35° C. The solution was stirred for 60 minutes at room temperature and poured onto ice/water (200 g). The organic layer was washed with brine and water until the pH of the solution was neutral. Drying (MgSO$_4$) and evaporation under reduced pressure gave a yellow oil which was distilled under reduced pressure at 90–110° C./0.5 mbar. Produce containing fractions were combined and purified by flash chromatography on silica gel using hexane as eluant to give a colourless oil (18.33 g, 33%).

b. N-(4-Methoxybenzyl)-6-hexyl phthalimide

6-Bromo-1-(4-methoxyphenyl)hexane (26.5 g, 0.1 mol) was dissolved in DMF (140 ml), potassium phthalimide (36.2 g, 0.2 mol) was added and the mixture stirred at 100° C. for 18 hours. The mixture was evaporated, the residue taken up in ether and excess potassium phthalimide filtered off. The filtrate was washed with water, dried (MgSO$_4$) and evaporated to a yellow solid which was recrystallised from ether/petroleum ether to give a pale yellow solid (20.0 g, 61%) mp 63°–65° C.

c. 6-(4-Methoxyphenyl)hexylamine

N-(4-methoxybenzyl)-1-hexyl phthalimide (19.9 g, 60 mmol) was dissolved in ethanol (300 ml) and hydrazine monohydrate (8.9 g, 0.11 mol) was added. The mixture was refluxed for 3 hours, filtered, the residue washed with ethanol and the filtrate evaporated. The residue was taken up in diethyl ether, filtered and the residue washed well with ether. Evaporation of the filtrate gave a yellow oil which was purified by distillation to give a clear oil bp 108–110° C., 0.02 mbar.

Preparation 2

6-(3,5-di$^t$butyl-4-hydroxyphenyl)hexylamine

This was prepared from 3,5-di$^t$butyl-4-hydroxy phenol according to the general procedure of Preparation 1.

Preparation 3

6-(3-chlorophenyl)hexylamine a. 6-(3-chlorophenyl)hexyn-1-ol

A stirred mixture of 3-chloroiodobenzene (14.3 g, 60 mmol), tetrakis(triphenylphosphine) palladium (2.1 g, 1.8 mmol) and 5-hexyn-1-ol (5.9 g, 60 mmol) in triethylamine (120 ml) was stirred at 25° C. for 3 h and partitioned between water and ether. The ether layer was separated and the aqueous extracted with ether. The combined either extracts were washed with 1N HCl and dried (Na$_2$SO$_4$). The ether was evaporated and the residue purified by flash chromatography on silica using dichloromethane as eluant. Evaporation of the appropriate fractions gave the product as an oil (11.5 g 92%)

b. 1-(Phthalimido)-6-(3-chlorophenyl)hex-1-yne

A solution of 6-(3-chlorophenyl)hexyn-1-ol (11.5 g, 55 mmol), triphenylphosphine (14.5 g, 55 mol) and phthalimide (8.1 g, 55 mol) in dry THF (110 ml) was treated with a solution of DEAD (9.6 g, 55 mmol) in THF (20 ml) over several minutes. After 16 h, volatiles were removed in vacuo and the residue treated with ether. The precipitated solid was removed, the filtrate evaporated and the residue purified by flash chromatography on silica using dichloromethane as eluant. Evaporation of the appropriate fractions gave the product as a solid (16.5 g, 89%)

c. 6-(3-chlorophenyl)hexylamine

A suspension of 1-(phthalimido)-6-(3-chlorophenyl)hex-1-yne (10 g, 30 mmol) in methanol (100 ml) was treated with platinum oxide (250 mg) and the mixture hydrogenated at 50 psi for 72 h. Further quantities of catalyst were added at intervals and when the theoretical uptake of hydrogen was complete, the mixture was filtered and the filtrate evaporated to a brown oil (9.5 g, 96%). This was dissolved in IMS 99 (100 ml) and treated with hydrazine hydrate (2.8 g, 56 mmol) under reflux for 16 h. The mixture was cooled to 5° C. and the precipitated solid removed by filtration. Evaporation of the filtrate gave an oil which was taken up in ether, washed with water, dried (Na$_2$SO$_4$) and evaporated to a brown oil (5.8 g, 98%)

Preparation 4

6-(3,5-dichlorophenyl)hexylamine

This was prepared using the general procedure of Preparation 3 and obtained as an oil.

Preparation 5-4-(4-(Allyloxycarbonyl)benzylthio) azetidin-2-one a. Allyl 4-(bromomethyl)benzoate 4-(Bromomethyl)benzoic acid (103 g, 0.48 moles) was suspended in thionyl chloride (200 ml) and dimethylformamide (1 ml) was added. The mixture was heated under reflux until clear, evaporated and azeotroped with toluene (2×150 ml). The resulting oil was dissolved in dichloromethane and added dropwise to a cooled solution of pyridine (42 ml) and allyl alcohol (40 ml) in dichloromethane. The mixture was stirred at room temperature for 1 hour, then washed with water, 2M hydrochloric acid, sodium hydrogen carbonate solution and brine. The organic solution was dried and evaporated to give allyl 4-(bromomethyl)benzoate as a clear oil (98 g, 84% yield). $^1$H NMR δ (CDCl$_3$) 4.61 (2H, s, CH$_2$), 4.82 (2H, m, CH$_2$O), 5.34 (2H, m, CH$_2$CH—), 6.05 (1H, m, CHCH$_2$), 7.45 (2H, d, Ph-H), 8.03 (2H, d, Ph-H).

b. Allyl 4-(acetylthiomethyl)benzoate

Allyl 4-(bromomethyl)benzoate (98 g, 0.4 moles) in dry dimethylformamide (100 ml) was added dropwise to a cooled suspension of potassium thioacetate (46 g, 0.4 moles) in dry dimethylformamide (200 ml). The cooling bath was removed and the mixture was stirred overnight. The reaction was poured into water and extracted with ethyl acetate (×3). The combined extracts were washed with water and brine. The mixture was dried and evaporated to give allyl 4-(acetylthiomethyl)benzoate as an orange oil (100 g, 100% yield). $^1$H NMR δ (CDCl$_3$) 2.36 (3H, s, COCH$_3$), 4.13 (2H, s, CH2), 4.82 (2H, m, CH$_2$O), 5.32 (2H, m, CH$_2$CH—), 6.05 (1H, m, CHCH$_2$), 7.35 (2H, d, Ph-H), 7.98 (2H, d, Ph-H).

c. 4-(4-(Allyloxycarbonyl)benzylthio)azetidin-2-one

Allyl alcohol (27 ml) in dry tetrahydrofuran (50 ml) was added dropwise to a solution of potassium tert-butoxide (4.93 g, 0.044 moles) in dry tetrahydrofuran (100 ml). After stirring for 5 minutes a solution of allyl 4-(acetylthiomethyl) benzoate (10.1 g, 0.04 moles) in dry tetrahydrofuran (100 ml) was added dropwise. After stirring for 15 minutes a solution of 4-acetoxyazetidin-2-one (5.16 g, 0.04 moles) was added dropwise. The mixture was stirred for 1 hour and evaporated. The residue was partitioned between ethyl acetate and water and the aqueous was extracted with ethyl acetate. The combined extracts were washed with brine, dried and evaporated. Flash chromatography (silica gel, ethyl acetate-petrol) gave 4-(4-Allyloxycarbonylbenzylthio) azetidin-2-one as an oil (9.1 g, 82% yield. $^1$H NMR δ (CDCl$_3$) 2.84 (1H, dd, H3a), 4.31 (1H, dd, H3b), 3.88 (2H, s, S—CH2), 4.68 (1H, dd, H4), 4.78 (2H, m, CH$_2$O), 5.35 (2H, m, CH$_2$CH—), 6.05 (1H, m, CHCH$_2$), 6.07 (1H, br. singlet, N—H), 7.40 (2H, d, Ph-H), 8.03 (2H, d, Ph-H).

Preparation 6-4-(4-(Allyloxycarbonylmethyl) benzylthio)azetidin-2-one.

a. Allyl 4-(bromomethyl)phenylacetate

Colourless oil, 95% yield. $^1$H NMR δ (CDCl$_3$) 3.7(2H, s), 4.5 (2H, s), 4.6(2H, m), 5.25(2H, m), 5.9(1H, m), 7.15–7.4 (4H, dd)

b. Allyl 4-(acetylthiomethyl)phenyl acetate

Colourless oil, 96% yield. $^1$H NMR δ (CDCl$_3$) 2.36(3H, s), 3.6(2H, s), 4.1(2H, s), 4.65(2H, m), 5.25(2H, m), 5.9(1H, m), 7.23(4H, dd)

c. 4-(4-Allyloxycarbonylmethyl)benzylthio)azetidin-2-one

Yellow oil, 69% yield. $^1$H NMR δ (CDCl$_3$) 2.81–2.88(1H, dd), 3.26–3.35(1H, dd), 3.65(2H, s), 3.83(2H, s), 4.6(2H, m), 4.68(1H, dd), 5.20–5.32(2H, m), 5.60(1H, broad) 5.8–6.0(1H, m), 7.21–7.31(4H, dd)

Literature references for other amines:

6-phenylhexylamine
Morse M. A. et al., Cancer Research, 1991, 1846

6-(4-Chlorophenyl)hexylamine
Lamattine J. L. EP 138464 A2 850424 (CA 103:142000)

6-(4-hydroxyphenyl)hexylamine
Goodwin B. L. et al., Xenobiotica, 1994, 24(2), 129

4-Acetoxyzetidin-2-one
Clauss K et al., Annalen, 1974, 539

EXAMPLES

Example 1

4-(Benzylthio)-1-(4-phenyl-2-oxobutyl)azetidin-2-one a. 4-(Benzylthio)azetidin-2-one Sodium (8.1 g, 0.35 mol) was dissolved in ethanol (250 ml) and benzyl mercaptan (45.2 g, 0.37 mol) added dropwise over 20 minutes keeping the temperature between 20° C.–25° C. whilst bubbling nitrogen through the mixture. After 15 minutes, the reaction was cooled to 5° C. and a solution of 4-acetoxyazetidin-2-one (45.0 g, 0.35 mol) in ethanol (50 ml) was added dropwise over 15 minutes whist maintaining the temperature at 5° C. The mixture was stirred at room temperature for 60 minutes and evaporated to dryness under reduced pressure. Water (500 ml) was added, the mixture extracted with dichloromethane (2×300 ml), the extracts dried (MgSO$_4$) and evaporated under reduced pressure to an oil. The oil was cooled to –20° C. and titurated with ether (400 ml) to give a white solid which was isolated by filtration (50.2 g, 79%), mp 50–51.0° C.

$^1$NMR δ (CDCl$_3$) 2.86(1H, m, H$_{3a}$), 3.30(1H, m, H$_{3b}$), 3.85 (2H, s, SCH$_2$), 4.68 (1H, m, H$_4$), 7.31 (5H, m, Ph-H).

b. 4-(Benzylthio)-1-(4-phenyl-2-oxobutyl)azetidin-2-one

To a cooled (cold water bath) solution of 4-(benzylthio)azetidin-2-one (5.5 g, 28.5 mmol), tetra-n-butylammonium bromide (0.9 g, 2.85 mmol) and 1-bromo-4-phenylbutan-2-one (7.1 g, 31.3 mmol) in dry THF (100 ml) was added freshly powdered potassium hydroxide (1.8 g, 31.3 mmol), and the mixture stirred vigorously for 2 hr at ambient temperature. Water was added and the product extracted into ethyl acetate, dried (MgSO$_4$) and evaporated to an oil. Treatment with ether gave the product as a white crystalline solid (3.12 g, 32%) mp 79–81° C.

$^1$H NMR δ (CDCl$_3$), 2.58 (2H, m, CH$_2$CO), 2.86 (2H, t, J=7.5 Hz, CH$_2$Ph), 2.96 (1H, dd, J=2.2, 15.2 Hz, H$_{3a}$), 3.17, 3.98 (each 1H, d, J=18.5 Hz, NCH$_2$), 3.43 (1H, dd, J=5.1, 15.2 Hz, H$_{3b}$), 3.70 (2H, s, SCH$_2$), 4.89 (1H, dd, J=2.4, 5.1 Hz, H$_4$), 7.15–7.33 (10 H, m, Ph-H).

Found: C, 70.9; H, 6.3; N, 4.3%; C$_{20}$H$_{21}$NO$_2$S requires: C, 70.8; H, 6.2; N, 4.1%

EXAMPLE 2

(4R,SR/4S,SS) 4-(Benzylsulphinyl)-1-(4-phenyl-2-oxobutyl)azetidin-2-one

A solution of 4-(benzylthio)-1-(4-phenyl-2-oxobutyl) azetidin-2-one (3.1 g, 9.2 mmol) in dichloromethane (100 ml) was cooled to –50 to –60° C. and a solution of m-chloroperbenzoic acid (1.9 g, 11 mmol) in dichloromethane (80 ml) added dropwise with stirring over 30 min. After a further 30 min at –50 to –60° C. the reaction mixture was shaken with a mixture of saturated aqueous sodium sulphite and saturated sodium hydrogen carbonate and the organic layer separated, dried (MgSO$_4$) and evaporated to a solid. Two recrystallisations from ethyl acetate gave (4R,SR/4S,SS) 4-(benzylsulphinyl)-1-(4-phenyl-2-oxobutyl)azetidin-2-one (0.8 g, 27%), mp 147–9° C.

$^1$H NMR δ (CDCl$_3$), 2.71 (2H, m, CH$_2$CO), 2.89 (2H, m, CH$_2$Ph), 2.93 (1H, dd, J=4.7, 14.8 Hz, H$_{3a}$), 3.36 (1H, dd, J=1.8, 14.8 Hz, H$_{3b}$), 3.72, 4.37 (each 1H, d, J=18.9 Hz, NCH$_2$), 3.9 (2H, s, CH$_2$SO), 4.70 (1H, dd, J=2.2, 4.7 Hz, H$_4$), 7.12–7.40 (10H, m, Ph-H).

Found: C, 67.5; H, 6.0; N, 4.0%; C$_{20}$H$_{21}$NO$_3$S requires: C, 67.6; H, 6.0; N, 3.9%

EXAMPLE 3

(4R,SS/4S,SR) 4-(Benzylsulphinyl)-1-(4-phenyl-2-oxobutyl)azetidin-2-one

The combined filtrates from the above crystallisations were evaporated and the residue recrystallised twice from ethanol to give a predominantly (4R,SS/4S,SR) 4-(benzylsulphinyl)-1-(4-phenyl-2-oxobutyl)azetidin-2-one (1.2 g, 37%), mp 110–11° C.

1H NMR δ (CDCl$_3$), 2.45 (1H, dd, J=2.3, 15.4 Hz, H$_{3a}$), 2.71 (2H, m, CH$_2$CO), 2.89 (2H, m, CH$_2$Ph), 3.03 (1H, dd, J=5.1, 15.3 Hz, H$_{3b}$), 3.94, 4.12 (each 1H,d, J=13.0 Hz, CH$_2$SO), 4.19, 4.37 (each 1H, d, J=19.2 Hz, NCH$_2$), 4.65 (1H, dd, J=2.4, 5.1 Hz, H$_4$), 7.12–7.40 (10H, m, Ph-H).

Found: C, 67.5; H, 6.1; N, 4.1%, C$_{20}$H$_{21}$NO$_3$S requires: C, 67.6; H, 6.0; N, 3.9%

EXAMPLE 4

4-(Benzylsulphonyl)-N-(4-phenyl-2-oxobutyl)azetidin-2-one

To a cooled (ice bath) solution of 4-(benzylthio)-N-(4-phenyl-2-oxobutyl)azetidinone (0.6 g, 1.76 mmol) in dichloromethane (25 ml) was added dropwise with stirring a solution of m-chloroperoxybenzoic acid (0.92 g, 5.3 mmol) in dichloromethane (25 ml). The ice bath was removed, and after 1.5 hr. the solution was washed with a mixture of saturated aq. sodium hydrogen carbonate and saturated aq. sodium sulphite. The aq. layer was back extracted with dichloromethane and the combined organic layers dried (MgSO$_4$) and evaporated to an oil which was crystallised from ether (0.56 g, 86%) mp 131–3° C.

1H NMR δ (CDCl$_3$), 2.69 (2H, t, J=6.9 Hz, CH$_2$CO), 2.9 (2H, m, CH$_2$Ph), 2.94 (1H, dd, J=2.1, 10.8 Hz, H$_{3a}$), 3.14 (1H, dd, J=5.1, 15.4 Hz, H$_{3b}$), 3.82, 4.35 (each 1H, d, J=18.8 Hz, NCH$_2$), 4.28 (2H, s, SO$_2$CH$_2$), 4.89 (1H, dd, J=2.3, 5.1 Hz, H$_4$), 7.14–7.43 (10H, m, Ph-H).

Found: C, 64.5; H, 5.8; N, 3.8%; $C_{20}H_{21}NO_4S$ requires: C, 64.7; H, 5.7; N, 3.8%

The following compounds (Examples 5 to 25) were prepared using the general procedures of Examples 1–4. Where shown, ratios indicate the relative diastereomeric proportion (4R,SR/4S,SS:4R,SS/4S,SR) as determined by $^1$H NMR.

EXAMPLE 5

4-(Benzythio)-1-(2-phenyl-2-oxoethyl)azetidin-2-one

Colourless oil, 48% yield.

1H NMR δ (CDCl$_3$) 3.02 (1H, dd, J=15.25, 2.00 Hz, $\underline{H}_{3a}$), 3.27 (1H, dd, J=15.25, 5.15 Hz, H$_{3b}$), 3.72 (1H, d, J=21.76, COC$\underline{H}_2$), 3.75 (2H, s, SC$\underline{H}_2$), 4.70 (1H, d, J=18.3, COC$\underline{H}_2$), 5.08 (1H, dd, J=5.13, 2.39, H$_4$), 7.08–7.29 (5H, m, Ph-H), 7.44–7.50 (2H, m, Ph-H), 7.57–7.64 (1H, m, Ph-H), 7.76–7.80 (2H, m, Ph-H).

EXAMPLE 6

(4R,SR/4S,SS) 4-(Benzylsulphinyl)-1-(2-phenyl-2-oxoethyl)azetidin-2-one

White solid, 11.5% yield, mp 130–31° C.

Found: C, 65.8; H, 5.2; N, 4.4%; $C_{18}H_{17}NO_3S$ requires: C, 66.0; H,5.2; N, 4.3%

EXAMPLE 7

(4R,SS/4S,SR) 4-(Benzylsulphinyl)-1-(2-phenyl-2-oxoethyl)azetidin-2-one

White solid, dias. ratio 15:85, 15% yield, mp 92–93° C.

Found: C, 65.8; H, 5.3; N, 4.4%; $C_{18}H_{17}NO_3S$ requires: C, 66.0; H, 5.2; N, 4.3%

EXAMPLE 8

4-(Benzylthio)-1-(9-phenyl-2-oxononyl)azetidin-2-one a. 1-bromo-9-phenylnonan-2-one A solution of 6-bromohexanoyl chloride (49.7 g, 0.233 mol) in dry dichloromethane (40 ml) was added dropwise over 5 minutes to a suspension of aluminium chloride (31.0 g, 0.233 mol) in dry dichloromethane (100 ml), keeping the temperature between 20° C.–23° C. The mixture was stirred for 30 minutes at room temperature to give a yellow solution. Benzene (18.2 g, 0.233 mol) in dry dichloromethane (30 ml) was added and stirred for 20 hours at room temperature. Triethylsilane (59.9 g, 0.515 mol) was added over 10 minutes, maintaining the temperature between 25° C.–35° C. The solution was stirred for 60 minutes at room temperature. This was then poured onto ice/water (200 g). A partial separation was achieved and the organic layer was washed with brine and water several times until the pH of the solution was neutral. The organic solution was dried (MgSO$_4$) and evaporated under reduced pressure to a yellow oil. This was distilled under reduced pressure at 90° C.–110° C./0.5 mbar to give colourless oils. The relevant fractions were combined and purified by flash chromatography on silica gel using hexane to give 6-bromo-1-phenylhexane as a colourless oil (18.33 g, 33%).

6-Bromo-1-phenylhexane (18.02 g, 0.075 mol) was dissolved in acetone (300 ml), NaI (44.85 g, 0.299 mol) was added, and the mixture heated at reflux temperature for 18 hours. This was filtered and the acetone evaporated under reduced pressure to give a residual mass which was extracted with n-pentane (150 ml). The insoluble solid was filtered off and the filtrate evaporated to give 6-iodo-1-phenylhexane as a colourless liquid (21.22 g, 99%).

6-Iodo-1-phenylhexane (17.43 g, 0.061 mol), acetyl acetone (6.66 g, 0.067) and potassium carbonate (8.41 g, 0.061 mol) were dissolved in dry absolute ethanol (75 ml) and the solution was refluxed for 18 hours. After cooling to room temperature the solution was filtered and evaporated under reduced pressure to an oil. This was partitioned between ethyl acetate (80 ml) and water (80 ml), and the organic layer was washed with brine, dried and evaporated to an orange oil (15.27 g). This was purified by flash chromatography on silica gel using petroleum ether/ethyl acetate to give 9-phenylnonan-2-one as a colourless oil (7.12 g, 54%).

Bromine (5.21 g, 0.033 mol) was added to a solution of 9-phenylnonan-2-one (7.12 g, 0.033 mol) in dry methanol (75 ml) and stirred for 2 hours at room temperature. Water (50 ml) was added and stirring continued for 18 hours at room temperature. Ether (175 ml) and water (100 ml) were added, the organic layer washed with dil. NaHCO$_3$, water (×2), dried (MgSO$_4$) and evaporated under reduced pressure to an oil (5.39 g). Petroleum ether (40° C.–60°C., 50 ml) was added and the mixture cooled to –10° C. and filtered. The solid obtained was re-dissolved in ether (40 ml) and evaporated under reduced pressure to an oil (4.06 g) which was was further purified by flash chromatography on silica gel using hexane/ethyl acetate to give 1-bromo-9-phenylnonan-2-one a pale yellow solid (3.80 g, 39%).

b. 4-(Benzylthio)-1-(9-phenyl-2-oxononyl)azetidinone

Colourless oil, 66% yield, $^1$H NMR δ (CDCl$_3$), 1.3 (6H, m, (C$\underline{H}_2$)$_3$), 1.55 (4H, m, C$\underline{H}_2$CH$_2$Ph, C$\underline{H}_2$CH$_2$CO), 2.24, (2H, m, C$\underline{H}_2$CO), 2.60 (2H, t, J=7.5 Hz, C$\underline{H}_2$Ph), 2.97 (1H, dd, J=2.2 , 15.2 Hz, H$_{3a}$), 3.21, 4.01 (each 1H, d, J=18.6 Hz, NC$\underline{H}_2$), 3.43 (1H, dd, J=5.1, 15.2 Hz, $\underline{H}_{3b}$), 3.73 (2H, s, SC$\underline{H}_2$), 4.93 (1H, dd, J=2.4, 5.1 Hz, H$_4$), 7.14–7.35 (10H, m, Ph-H).

EXAMPLE 9

(4R,SR/4S,SS) 4-(Benzylsulphinyl)-1-(9-phenyl-2oxononyl)azetidin-2-one

Colourless solid, 25% yield, mp 133–5° C., 1H NMR δ (CDCl$_3$), 1.30 (m, 6H, (C$\underline{H}_2$)$_3$), 1.58 (4H, m, C$\underline{H}_2$CH$_2$Ph, C$\underline{H}_2$CH$_2$CO), 2.37 (2H, t, J=7.5 Hz, C$\underline{H}_2$CO), 2.59 (2H, t, J=7.9 Hz, C$\underline{H}_2$Ph), 2.94 (1H, dd, J=4.7, 14.8 Hz, $\underline{H}_{3a}$), 3.36 (1H, dd, J=1.7, 14.9 Hz, $\underline{H}_{3b}$), 3.79, 4.42 (each 1H, d, J=18.9 Hz, NC$\underline{H}_2$), 3.91 (2H, s, SOC$\underline{H}_2$), 4.77 (1H, dd, J=2.2, 4.7 Hz, H$_4$), 7.15–7.4 (10H, m, Ph-$\underline{H}$). Found: C, 70.3; H, 7.2; N, 3.4%; $C_{25}H_{31}NO_3S$ requires: C, 70.6; H, 7.3; N, 3.3%.

EXAMPLE 10

(4R,SS/4S,SR) 4-(Benzylsulphinyl)-1-(9-phenyl-2-oxononyl-azetidin-2-one

Dias. Ratio 1:0, Colourless solid, 30% yield, mp 75–6° C., 1H NMR δ (CDCl$_3$), 1.3 (m, 6H, (C$\underline{H}_2$)$_3$), 1.58 (4H, m, C$\underline{H}_2$CH$_2$Ph, C$\underline{H}_2$CH$_2$CO), 2.34 (2H, t, J=7.6 Hz, C$\underline{H}_2$CO), 2.43 (1H, dd, J=2.3, 15.2 Hz, $\underline{H}_{3a}$), 2.59 ()2H, t, J=7.4 Hz, C$\underline{H}_2$Ph), 3.02 (1H, dd, J=5.1 15.3 Hz, $\underline{H}_{3b}$), 3.94, 4.13 (each 1H, d, J=13.0 Hz, SOC$\underline{H}_2$), 4.19, 4.38 (each 1H, d, J=18.7 Hz, NC$\underline{H}_2$), 4.65 (1H, dd, J=2.4, 5.1 Hz. H$_4$), 7.14–7.43 (10H, m, Ph-$\underline{H}$). Found: C, 70.4; H, 7.3; N, 3.4%; $C_{25}H_{31}NO_3S$ requires: C, 70.6; H, 7.3; N, 3.3%.

EXAMPLE 11

4-(2-Methoxybenzylthio)-N-(4-phenyl-2-oxobutyl)azetidin-2-one

Colourless oil, 62% yield, 1H NMR δ (CDCl$_3$), 2.60 (2H, m, C$\underline{H}_2$CO), 2.87 (2H, t, J=7.5 Hz, C$\underline{H}_2$Ph), 3.01 (1H, dd, J=2.2, 15.2 Hz, $\underline{H}_{3a}$), 3.23, 4.00 (each 1H, d, J=18.6 Hz, NC$\underline{H}_2$), 3.43 (1H, dd, J=5.1, 15.2 Hz, $\underline{H}_{3b}$), 3.72 (2H, d, J=2.4 Hz, SC$\underline{H}_2$), 3.83 (3H, s, OC$\underline{H}_3$), 4.95 (1H, dd, J=2.4, 5.1 Hz, $\underline{H}_4$) 6.81–6.92 (2H, m, 3,5-(2-CH$_3$OPh)-$\underline{H}$), 7.15–7.32 (7H, m, 4,6-(2-CH$_3$OPh)-$\underline{H}$, Ph-$\underline{H}$).

EXAMPLE 12

(4R,SR/4S,SS) 4-(2-Methoxybenzylsulphinyl)-N-(4-phenyl-2-oxobutyl)azetidin-2-one White crystalline solid, 8% yield, mp 90–2° C. 1H NMR δ (CDCl$_3$), 2.71 (12H, m, C$\underline{H}_2$CO), 2.88 (2H, m, C$\underline{H}_2$Ph), 3.00 (1H, dd, J=4.7, 14.8 Hz, $\underline{H}_{3a}$), 3.46 (1H, dd, J=1.9, 14.8 Hz, $\underline{H}_{3b}$), 3.70, 4.35 (each 1H, d, J=18.4 Hz, NC$\underline{H}_2$), 3.88 (3H, s, OC$\underline{H}_3$), 4.00(2H, s, SC$\underline{H}_2$), 4.75 (1H, dd, J=2.2, 4.7 Hz, $\underline{H}_4$), 6.90–7.38 (9H, m, Ph$\underline{H}$+CH$_3$OPh-$\underline{H}$). Found: C, 65.3; H, 6.0; N, 3.9%; C$_{21}$H$_{23}$NO$_4$S requires: C, 65.4; H, 6.0; N, 3.6%.

EXAMPLE 13

(4R,SS/4S,SR) 4-(2-Methoxybenzylsulphinyl)-N-(4-phenyl-2-oxobutyl)azetidin-2-one Colourless oil, dias. ratio 1:3, 25% yield 1H NMR δ (CDCl$_3$), 2.49 (1H, dd, J=2.2, 15.4 Hz, $\underline{H}_{3a}$), 2.71 (2H, m, C$\underline{H}_2$CO), 2.89 (2H, m, C$\underline{H}_2$Ph), 3.04 (1H, dd, J=5.1, 15.4 Hz, $\underline{H}_{3b}$), 3.87 (3H, s, OC$\underline{H}_3$), 4.09 (2H, s, SC$\underline{H}_2$), 4.19, 4.36 (each 1H, d, J=18.6 Hz, NC$\underline{H}_2$), 4.69 (1H, dd, J=2.3, 5.0 Hz, $\underline{H}_4$), 6.89–7.34 (9H, m, Ph-$\underline{H}$+CH$_3$OPh-$\underline{H}$). Found: C, 64.8; H, 6.1; N, 3.8%; C$_{21}$H$_{23}$NO$_4$S.0.17H$_2$O requires: C, 64.9; H, 6.1; N, 3.6%.

EXAMPLE 14

4-(4-Fluorobenzylthio)-N-(4-phenyl-2-oxobutyl)azetidin-2-one

Colourless oil, 41% yield, 1H NMR δ (CDCl$_3$), 2.64 (2H, m, C$\underline{H}_2$CO), 2.88 (2H, t, J=7.5 Hz, C$\underline{H}_2$Ph), 2.95 (1H, dd, J=2.3, 15.3 Hz, $\underline{H}_{3a}$), 3.3, 4.06 (each 1H, d, J=18.6 Hz, NC$\underline{H}_2$), 3.42 (1H, dd, J=5.1, 15.3 Hz, $\underline{H}_{3b}$), 3.67 (2H, s, SC$\underline{H}_2$), 4.88 (1H, dd, J=2.4, 5.1 Hz, H$_4$), 6.84–7.33 (9H, m, Ph-$\underline{H}$, 4-FPh-$\underline{H}$).

EXAMPLE 15

(4R,SR/4S,SS) 4-(4-Fluorobenzylsulphinyl)-N-(4-phenyl-2-oxobutyl)azetidin-2-one White crystalline solid, 16% yield, mp 152–4° C. 1H NMR δ (CDCl$_3$), 2.74 (2H, t, J=7.0 Hz, C$\underline{H}_2$CO), 2.90 (2H, t, J=6.8 Hz, C$\underline{H}_2$Ph), 2.95 (1H, dd, J=4.7, 14.8 Hz, $\underline{H}_{3a}$), 3.35 (1H, dd, J=1.8, 14.8 Hz, $\underline{H}_{3b}$), 3.76, 4.40 (each 1H, d, J=18.9 Hz, NC$\underline{H}_2$), 3.85 (2H, m, SC$\underline{H}_2$), 4.73 (1H, dd, J=2.2, 4.7 Hz, H$_4$), 7.04–7.32 (9H, m, Ph-$\underline{H}$, 4-FPh-$\underline{H}$). Found: C, 64.2; H, 5.4; N, 3.9%; C$_{20}$H$_{20}$FNO$_3$S requires: C, 64.3; H, 5.4; N, 3.8%.

EXAMPLE 16

(4R,SS/4S,SR) 4-(4-Fluorobenzylsulphinyl)-N-(4-phenyl-2-oxobutyl)azetidin-2-one White crystalline solid, 26% yield, mp 114–6° C. 1H NMR δ (CDCl$_3$), 2.60 (1H, dd, J=2.3, 15.2 Hz, $\underline{H}_{3a}$), 2.71 (2H, m, C$\underline{H}_2$CO), 2.91 (2H, m C$\underline{H}_2$Ph), 3.15 (1H, dd, J=5.1, 15.2 Hz, $\underline{H}_{3b}$), 3.96 (2H, m, SC$\underline{H}_2$), 4.19, 4.38 (each 1H, d, J=18.7 Hz, NC$\underline{H}_2$), 4.65 (1H, dd, J=2.4, 5.1 Hz, H$_4$), 7.05–7.33 (9H, m, Ph-$\underline{H}$, 4-FPh-$\underline{H}$). Found: C, 64.1; H, 5.5; N, 3.9%; C$_{20}$H$_{20}$FNO$_3$S requires: C, 64.3; H, 5.4; N, 3.8%.

EXAMPLE 17

4-(4-Methoxybenzylthio)-N-(4-phenyl-2-oxobutyl)azetidin-2-one

White crystals, 74% yield, mp 70–71° C. 1H NMR δ (CDCl$_3$) 2.60 (1H, t, J=7.13 Hz, C$\underline{H}_2$Ph), 2.86 (1H, t, J=7.59 Hz, COC$\underline{H}_2$), 2.96 (1H, dd, J=15.25, 2.20 Hz, H$_{3a}$), 3.24 (1H, d, J=18.53 Hz, NC$\underline{H}_2$), 3.42 (1H, dd, J=15.25, 5.11 Hz, H$_{3b}$), 3.66 (2H, s, SC$\underline{H}_2$), 3.76 (3H, s, OC$\underline{H}_3$), 4.02 (1H, d, J=18.53 Hz, NC$\underline{H}_2$), 4.88 (1H, dd, J=5.10, 2.39 Hz, H$_4$), 6.79–6.84 (2H, m, Ph-H), 7.16–7.32 (7H, m, Ph-H).

EXAMPLE 18

(4R,SR/4S,SS) 4-(4-Methoxybenzylsulphinyl)-N-(4-phenyl-2-oxobutyl)azetidin-2-one White crystalline solid, 20% yield, mp 155–157° C. Found: C, 64.5; H, 6.0; N, 3.5%; C$_{21}$H$_{23}$NO$_4$S 0.3 H$_2$O requires: C, 64.5; H, 6.1; N, 3.6%.

EXAMPLE 19

(4R, SS/4S,SR) 4-(4-Methoxybenzylsulphinyl)-N-(4-phenyl-2-oxobutyl)azetidin-2-one White crystalline solid, 80% above diast., mp 92–93° C., 31% yield, Found: C, 64.7; H, 6.0; N, 3.5%. C$_{21}$H$_{23}$NO$_4$S 0.2 H$_2$O requires: C, 64.8; H, 6.1; N, 3.6%.

EXAMPLE 20

4-(Phenethylthio)-N-(4-phenyl-2-oxobutyl)azetidin-2-one

Colourless oil, 80% yield, 1H NMR δ (CDCl$_3$) 2.65–2.97 (9H, m, S—C$\underline{H}_2$C$\underline{H}_2$, COC$\underline{H}_2$C$\underline{H}_2$, $\underline{H}_{3a}$), 3.39 (1H, dd, J=15.22, 5.00 Hz, H$_{3b}$), 3.50 and 4.17 (1H each, d, J=18.48 Hz, N—C$\underline{H}_2$), 4.83 (1H, dd, J=4.99, 2.34 Hz, H$_4$), 7.14–7.33 (10H, m, Ph-$\underline{H}$).

EXAMPLE 21

(4R, SR/4S,SS) 4-(Phenethylsulphinyl)-N-(4-phenyl-2-oxobutyl)azetidin-2-one

White crystalline solid, 8% yield, mp 163–165° C. Found: C, 68.0; H, 6.2; N, 4.0%; C$_{21}$H$_{23}$NO$_3$S requires: C, 68.3; H, 6.3; N, 3.8%.

EXAMPLE 22

4R,SS/4S,SR) 4-(Phenethylsulphinyl)-N-(4-phenyl-2-oxobutyl)azetidin-2-one

White crystalline solid, 14.5% yield, mp 91–92° C. Found: C, 68.08; H, 6.32; N, 3.86%; C$_{21}$H$_{23}$NO$_3$S requires: C, 68.3; H, 6.3; N, 3.8%.

EXAMPLE 23

4-(3-Phenylpropylthio)-N-(4-phenyl-2-oxobutyl)azetidin-2-one

Colourless oil, 67% yield, 1H NMR δ (CDCl$_3$), 1.87 (2H, m, SC$\underline{H}_2$C$\underline{H}_2$), 2.47 (2H, m, C$\underline{H}_2$CO), 2.72 (4H, m, 2xC H2Ph), 2.9 (2H, t, J=7.1 Hz, C$\underline{H}_2$S), 2.96 (1H, dd, J=2.2, 15.2 Hz, $\underline{H}_{3a}$), 3.48 (1H, dd, J=5.0, 15.2 Hz, $\underline{H}_{3b}$), 3.63, 4.23 (each 1H, d, J=18.5 Hz, NC$\underline{H}_2$), 4.86 (1H, dd, J=2.3, 5.0 Hz, $\underline{H}_4$), 7.14–7.32 (10H, m, Ph-$\underline{H}$).

EXAMPLE 24

(4R,SR/4S,SS) 4-(3-Phenylpropylsulphinyl)-N-(4-phenyl-2-oxobutyl)azetidin-2-one

White crystalline solid, 25% yield, mp 136–8° C. 1H NMR δ (CDCl$_3$), 2.11 (2H, m, SOCH$_2$C$\underline{H}_2$), 2.49 (2H, m, SOC$\underline{H}_2$), 2.78 (4H, m, 2xC$\underline{H}$2Ph), 2.91 (2H, m, C$\underline{H}_2$CO), 3.15 (1H, dd, J=4.8, 14.7 Hz, $\underline{H}_{3a}$), 3.55 (1H, dd, J=1.7, 14.7 Hz, $\underline{H}_{3b}$), 3.78, 4.44 (each 1H, d, J=18.9 Hz, NC$\underline{H}_2$), 4.66 (1H, dd, J=2.2, 4.8 Hz, $\underline{H}_4$), 7.14–7.35 (10H, m, Ph-$\underline{H}$). Found: C, 68.6; H, 6.4; N, 3.8%; C$_{22}$H$_{25}$NO$_3$S requires: C, 68.9; H, 6.6; N, 3.7%.

EXAMPLE 25

4R, SS/4S,SR) 4-(3-Phenylpropylsulphinyl)-N-(4-phenyl-2-oxobutyl)azetidin-2-one

White crystalline solid, 13% yield, mp 65–6° C. 1H NMR δ (CDCl$_3$), 2.12 (2H, m, SOCH$_2$C$\underline{H}_2$), 2.54 (2H, m, SOC$\underline{H}_2$), 2.55–2.94(7H, m, 2xC$\underline{H}$2Ph+C$\underline{H}_2$CO+$\underline{H}_{3a}$), 3.33 (1H, dd, J=5.2, 15.1 Hz, $\underline{H}_{3b}$), 4.20, 4.40 (each 1H, d, J=18.7 Hz, NC$\underline{H}_2$), 4.66 (1H, dd, J=2.2, 4.8 Hz, $\underline{H}_4$), 7.14–7.35 (10H, m, Ph-$\underline{H}$). Found: C, 68.6; H, 6.5; N, 3.9%; C$_{22}$H$_{25}$NO$_3$S requires: C, 68.9; H, 6.6; N, 3.7%.

EXAMPLE 26 trans 3-Methyl-4-(benzylthio)-1-(4-phenyl-2-oxobutyl)azetidin-2-one

A solution of trans-3-methyl-4-(benzylthio)azetidin-2-one (0.73 g, 3.5 mmol) in dry THF (5 ml) was added dropwise over 5 minutes to a suspension of sodium hydride (60% dispersion in oil, 0.15 g, 3.8 mmol) in dry THF (10 ml) under a nitrogen atmosphere at –10° C. The mixture was stirred for 10 minutes at –10° C. and 1-bromo-4-phenylbutan-2-one (0.79 g, 3.5 mmol) in dry THF (10 ml) was added over 5 minutes at –10° C. The mixture was stirred at room temperature for 30 minutes and poured into ice/water. The layers were separated and the aqueous was extracted with ethyl acetate. The combined organics were washed with brine, dried (MgSO$_4$) and evaporated to an oil. This was purified by flash chromatography on silica gel eluting with petroleum ether 40–60° C./ethyl acetate 3:1, 2:1 to give a colourless solid (0.34 g, 27%) mp 69–71° C.

$^1$H NMR δ (CDCl$_3$) 1.34 (3H, d, J=7 Hz, SC$\underline{H}_3$), 2.55 (2H, m, C$\underline{H}_2$Ph), 2.85 (2H, t, J=8 Hz, COC$\underline{H}_2$CH$_2$), 3.11, 3.97 (each 1H, d, J=18 HZ, NC$\underline{H}_2$), 3.15 (1H, m, $\underline{H}_3$), 3.70 (2H, m, SC$\underline{H}_2$), 4.50 (1H, d, J=2 Hz, $\underline{H}_4$), 7.1–7.4 (10H, m, 2xPh-$\underline{H}$).

EXAMPLE 27

(4R,SR/4S,SS) trans 3-Methyl-4-(benzylsulphinyl)-1-(4-phenyl-2-oxobutyl)azetidin-2-one Prepared from trans 3-methyl-4-(benzylthio)-1-(4-phenyl-2-oxobutyl)azetidin-2-one using the general procedure of Example 2 and obtained as a white solid, 40% yield, mp 87–94° C.

$^1$H NMR δ (CDCl$_3$) 1.23 (3H, d, J=7 Hz, C$\underline{H}_3$), 2.71 (2H, m, C$\underline{H}_2$Ph), 2.9 (3H, m, COC$\underline{H}_2$+$\underline{H}_3$), 3.91, 4.09 (each 1H, d, J=13 Hz, SOC$\underline{H}_2$), 4.17, 4.39 (each 1H, d, J=19 Hz, NC$\underline{H}_2$), 4.38 (1H, d, J=2 Hz, $\underline{H}_4$), 7.1–7.4 (10H, m, Ph-$\underline{H}$). Found: C, 68.1; H, 6.3; N, 4.0%; C$_{21}$H$_{23}$NO$_3$S requires: C, 68.3; H, 6.3; N, 3.8%.

EXAMPLE 28

(4R,SS/4S,SR) trans 3-Methyl-4-(benzylsulphinyl)-1-(4-phenyl-2-oxobutyl)azetidin-2-one Prepared from trans 3-methyl-4-benzylthio)-1-(4-phenyl-2-oxobutyl)azetidin-2-one using the general procedure of Examples 2 and 3 and obtained as a white solid, dias. ratio 1:4, 19% yield, mp 114–7° C.

$^1$H NMR δ (CDCl$_3$) 1.43 (3H, d, J=8 Hz, C$\underline{H}_3$), 2.7 (2H, m, C$\underline{H}_2$Ph), 2.9 (2H, m, COC$\underline{H}_2$), 3.65, 4.37 (each 1H, d, J=19 Hz, NC$\underline{H}_2$), 3.82 (1H, m, $\underline{H}_3$), 3.93 (2H, m, SOC$\underline{H}_2$), 4.44 (1H, d, J=2 Hz, $\underline{H}_4$), 7.1–7.4 (10H, m, Ph-$\underline{H}$), Found: C, 68.1; H, 6.3; N, 4.0%; C$_{21}$H$_{23}$NO$_3$S requires; C, 68.3; H, 6.3; H, 3.8%.

EXAMPLE 29

N-(6-phenylhexyl)-(4-benzylthio-2-oxoazetidin-1-yl)acetamide a. Methyl-(4-benzylthio-2-oxoazetidin-1-yl) Acetate To a solution of 4-benzylthio)azetidin-2-one (5.0 g, 25 mmol), methyl bromoacetate (4.6 g, 30 mmol) and tetrabutylammonium bromide (0.9 g, 0.28 mmol) in dry THF (150 ml) was added powdered potassium hydroxide (1.7 g, 30 mmol). The resulting mixture was stirred for two hours at room temperature before water (50 ml) was added. The solution was extracted with ethyl acetate (3×150 ml portions) and the combined extracts dried (MgSO$_4$) and evaporated. The residue was purified by flash chromatography on silica gel eluted with petroleum ether 60°–80°:ethyl acetate 4:1 to give methyl (4-benzylthio-2-oxoazetidin-1-yl) acetate as a yellow oil (5 g, 70%). $^1$H NMR δ (CDCl$_3$) 2.96(1H, dd, J=2.5, 16 Hz $\underline{H}_{3a}$), 3.24, 3.99 (each 1H, d, J=18.00 Hz, NC$\underline{H}_2$), 3.4 (1H, dd, J=5, 12.5 Hz $\underline{H}_{3b}$), 3.70 (3H, s, OC$\underline{H}_3$), 3.77 (2H, s, SC$\underline{H}_2$), 4.92 (1H, m, $\underline{H}_4$), 7.28 (5H, m, Ph-$\underline{H}$).

b. (4-Benzylthio-2-oxoazetidin-1-yl)acetic Acid

To a solution of methyl (4-benzylthio-2-oxo-azetidin-1-yl)acetate (2.5 g, 9.4 mmol) in methanol (80 ml) was added, dropwise at 0° C., a solution of 1 N sodium hydroxide (9.9 ml, 9.9 mmol). The reaction was stirred for 1 hr and evaporated to dryness. Water (50 ml) was added and the solution acidified to pH 3 with dilute hydrochloric acid and extracted with ethyl acetate (3×100 ml). The combined extracts were dried (MgSO$_4$), evaporated and the residue purified by recrystallisation (hexane/ether) to give (4-benzylthio-2-oxo-azetidin-1-yl)acetic acid as a white solid (1.3 g, 55%), mp 110–110° C. $^1$H NMR δ (CDCl$_3$) 2.99 (1H, dd, J=6.87, 17.5 Hz, $\underline{H}_{3a}$), 3.27, 4.06 (each 1H, d, J=18.40 Hz, NC$\underline{H}_2$), 3.39 (1H, dd, J=5, 15.4 Hz, $\underline{H}_{3b}$), 3.77 (2H, s, SC$\underline{H}_2$), 4.91 (1H, m, $\underline{H}_4$), 7.27 (5H, m, Ph-$\underline{H}$).

c. N-(6-phenylhexyl)-(4-benzylthio-2-oxoazetidin-1-yl) acetamide

A solution of 6-phenylhexylamine (Morse M. A. et al., Cancer Research, 1991, 1846), (7.0 g, 40 mmol) in DMF (20 ml) was added to DCC (8.2 g, 40 mmol), hydroxybenzotriazole (5.3 g, 39 mmol) and (4-benzylthio-2-oxoazetidin-1-yl)acetic acid (10 g, 39 mmol) and the mixture stirred for 2 hours at room temperature. Ethyl acetate (250 ml) was added, the precipitate filtered, the filtrate washed with dil NaHCO$_3$, water (×2), dried (MgSO$_4$) and evaporated to an oil which was purified by flash chromatography on silica gel using hexane/ethyl acetate (1:1). Evaporation of the appropriate fractions followed by treatment with hexane gave a white solid (11.2 g, 70%), mp 65–70° C.

EXAMPLE 30

(4R,SR/4S,SS) N-(6-phenylhexyl)-(4-benzylsulphinyl-2-oxoazetidin-1-yl)acetamide

A solution of N-(6-phenylhexyl)-4-benzylthio-2-oxoazetidin-1-yl acetamide (18.0 g, 43.8 mmol) in dichloromethane (500 ml) was cooled to −70° C. and a solution of m-chloroperbenzoic acid (6.7 g, 43.8 mmol) in dichloromethane (500 ml) added dropwise with stirring over 60 min. After a further 3 h at −60° C., the reaction mixture was shaken with a mixture of saturated aqueous sodium sulphite and saturated sodium hydrogen carbonate. The organic layer was separated, washed with brine, dried (MgSO$_4$) and evaporated to a solid which was titurated with ether and filtered. Two recrystallisations from ethyl acetate gave (4R, SR/4S,SS) N-(6phenylhexyl)-4-benzylsulphinyl-2-oxoazetidin-1-yl acetamide (3.8 g, 20%) mp 138–140° C.

Found: C, 64.4; H, 6.9; N, 6.8%; C$_{24}$H$_{30}$N$_2$O$_3$S requires: C, 67.6; H, 7.1; N, 6.6%.

EXAMPLE 31

(4R, SS/4S,SR) N-(6-phenylhexyl)-(4-benzylsulphinyl-2-oxoazetidin-1-yl)acetamide The above filtrate was diluted with hexane, filtered and upon standing deposited the title compound as a colourless crystalline solid (4.5 g, 24%), mp 107–108° C.

Found: C, 67.4; H, 7.1; N, 6.8%; C$_{24}$H$_{30}$N$_2$O$_3$S required: C, 67.6; H, 7.1;N, 6.6%.

The following compounds (Examples 32 to 57) were prepared using the general procedure of Examples 29–31. Where shown, ratios indicate the relative diastereomeric proportion (4R,SR/4S,SS:4R, SS/4S/SR) as determined by $^1$H NMR.

EXAMPLE 32

N-benzyl-(4-benzylthio-2-oxoazetidin-1-yl)acetamide

White solid, 49% yield, mp 89–90° C., $^1$H NMR δ (CDCl$_3$) 2.94 (1H, dd, J=2.5, 5.25 Hz, H$_{3a}$), 3.37 (1H, dd, J=2.5, 5 Hz, H$_{3b}$), 3.65, 3.76 (each 1H, d, J=15.0 Hz, NCH$_2$), 3.76 (2H, s, SCH$_2$), 4.4 (2H, m, NHCH$_2$), 4.81 (1H, m, H$_4$), 6.33 (1H, bs, NH), 7.20–7.37 (10H, m, Ph-H).

EXAMPLE 33

(4R,SR/4S,SS) N-benzyl-(4-benzylsulphinyl-2-oxoazetidin-1-yl)acetamide

White crystalline solid, 8% yield, mp 192–193° C., Found: C, 63.8; H, 5.7; N, 8.0%, C$_{19}$H$_{20}$N$_2$O$_3$S requires: C, 64.0; H, 5.7; N, 7.9%.

EXAMPLE 34

(4S, SS/4S,SR) B-benzyl-(4-benzylsulphinyl-2-oxoazetidin-1-yl)acetamide

White solid, dias. ratio 15:85, 36% yield, mp 181–182° C. Found: C, 63.4; H, 5.5; N, 7.7%; C$_{19}$H$_{20}$N$_2$O$_3$S 0.2 H$_2$O requires: C, 63.5; H, 5.7; N, 7.8%.

EXAMPLE 35

N-(4-Phenylbutyl)-(4-benzylthio-2-oxoazetidin-1-yl)acetamide

Colourless oil, 100% yield. $^1$H NMR δ (CDCl$_3$) 1.5–1.7 (4H, m, CH$_2$CH$_2$), 2.63 (2H, t, J=7 Hz, CHhd 2Ph), 2.93 (1H, dd, J=2, 15 Hz, H$_3$), 3.26 (2H, m, NCH$_2$), 3.36 (1-H, dd, J=5, 15 Hz, H$_3$), 3.53, 3.70 (each 1H, d, J=17 Hz, NCH$_2$), 3.79 (2H, s, SCH$_2$), 4.80 (1H, m, H$_4$), 6.07 (1H, br s, NH), 7.1–7.4 (1H, m, 2xPh-H).

EXAMPLE 36

(4R,SR/4S,SS) N-(4-
$^1$H NMR δ (CDCl$_3$) 1.5–1.7 (4H, m, CH$_2$CH$_2$) 2.62 (2H, t, J=7 Hz, CH$_2$Ph), 2.95 (1H, dd, J=5, 15 Hz, H$_3$), 3.26 (2H, m, NHCH$_2$), 3.4 5(1H, dd, J=2, 15 Hz, H$_3$), 3.71, 4.10 (each 1H, d, J=17 Hz, NCH$_2$), 3.88, 4.04 (each 1H, d, J=13 Hz, SOCH$_2$), 4.51 (1H, m, H$_4$), 6.65 (1H, br s, NH), 7.1–7.4 (1H, m, 2xPh-H), Found: C, 66.2; H, 6.5; N, 7.0%; C$_{22}$H$_{26}$N$_2$O$_3$S requires: C, 66.3; H, 6.6; N, 7.0%.

EXAMPLE 37

(4R, SS/4S,SR) N-(4-Phenylbutyl)-4-(benzylsulphinyl-2-oxoazetidin-1-yl)acetamide White solid, dias. ratio 5:95, 30% yield, mp 107–8° C. $^1$H NMR δ (CDCl$_3$) 1.5–1.7 (4H, m, CH$_2$CH$_2$), 2.63 (2H, t, J=7 Hz, CH$_2$Ph), 2.85 (1H, dd, J=2, 15 Hz, H), 3.15 (1H, dd, J=5, 15 Hz, Hhd 3), 3.3 (2H, m, NHCH$_2$), 3.90, 4.23 (each 1H, d, J=17 Hz, NCH$_2$), 3.97, 4.15 (each 1H, d, J=13 Hz, SOCH$_2$), 4.60 (1H, m, H$_4$), 7.1–7.4 (11H, m, 2xPh-H+NH), Found: C, 66.1; H, 6.5; N, 7.1%; C$_{22}$H$_{26}$N$_2$O$_3$ S requires: C, 66.3; H, 6.6; N, 7.0%.

EXAMPLE 38

N-(9-Phenylnonyl)-(4-benzylthio-2-oxoazetidin-1-yl)acetamide

Colourless oil, 84% yield. $^1$H nmr δ (CDCl$_3$) 1.28–1.48 (14H, m, 7xCH$_2$), 2.59 (2H, t, J=7.7 Hz, PhCH$_2$), 2.92, 2.98 (1H, dd, J=2.5, 15.4 Hz, H$_3$), 3.2 (2H, m, NHCH$_2$), 3.34, 3.40 (1H, dd, J=5.2, 15.4 Hz, H$_3$), 3.56, 3.72 (each 1H, d, J=16.8 Hz, NCH$_2$), 3.81 (2H, s, SCH$_2$), 4.81 (1H, m, H$_4$), 6.0 (1H, m, NH), 7.2 (10H, m, 2xPh-H).

EXAMPLE 39

(4R,SR/4S,SS) N-(9-Phenylnonyl)-(4-benzylsulphinyl-2-oxoazetidin-1-yl)acetamide

White solid, dias. ratio 4:1, 8% yield, mp 124–128° C. $^1$H nmr δ (CDCl$_3$) 1.2–1.7 (14H, m, 7xCH$_2$), 2.59 (2H, t, J=7.8 Hz, PhCH$_2$), 2.93, 2.97 (1H, dd, J=4.8, 14.8 Hz, H$_3$), 3.23 (2H, m, NHCH$_2$), 3.44, 3.48 (1H, dd, J=2.4, 14.8 Hz, H$_3$), 3.7, 4.1 (each 1H, d, J=17.2 Hz, NCH$_2$), 3.9, 4.13 (each 1H, d, J=12.8 Hz, SOCH$_2$), 4.5 (1H, m, H$_4$), 6.59 (1H, m, NH), 7.16–7.41 (10H, m, 2xPh-H), Found: C, 68.9; H, 7.5; N, 5.6%; C$_{27}$H$_{36}$N$_2$O$_3$S requires: C, 69.2; H, 7.7; N, 6.0%.

EXAMPLE 40

(4R,SS/4S,SR) N-(9-phenylnonyl)-(4-benzylsulphinyl-2-oxoazetidin-1-yl)acetamide

White solid, dias. ratio 4:6, 48% yield, mp 123–128° C., $^1$H nmr δ (CDCl$_3$) 1.2–1.7 (14H, m, 7xCH$_2$), 2.59 (2H, t, J=7.8 Hz, PhCH₂), 2.85–2.97 (1H, m H₃), 3.1–3.5 (3H, m, NHCH₂, H₃), 3.7–4.2 (4H, m, SOCH₂, NCH₂), 4.5–4.6 (1H, 2×m, H₄), 6.68 (m, NH'), 7.17–7.42 (1H, m, 2×Ph-H), Found: C 69.3; H, 7.8; N, 6.1%; C₂₇H₃₆N₂O₃S requires: C, 69.2; H, 7.7; N, 6.0%.

EXAMPLE 41

N-Methyl-N-(6-phenylhexyl)-(4-benzylthio-2-oxoazetidin-1-yl)acetamide

Yellow oil, 88% yield. ¹H nmr δ (DMSO-d₆ 350K) 1.24–1.57 (8H, m, 4×CH₂), 2.55 (2H, m, PhCH₂), 2.79–2.95 (4H, m, NCH₃, H₃), 3.1–3.3 (2H, m, NCH₂), 3.32, 3.35 (1H, dd, J=5.2, 14.8 Hz, H₃), 3.45, 4.09 (each 1H, d, J=16.8 Hz, NCH₂C=O), 3.84 (2H, s, SCH₂), 4.94 (1H, m, H₄), 7.14–7.32 (10H, m, 2×Ph-H).

EXAMPLE 42

(4R,SR/4S,SS) N-Methyl-N-(6-phenylhexyl)-(4-benzylsulphinyl-2-oxoazetidin-1-yl)acetamide Colourless oil, dias. ratio 55:45, 67% yield, ¹H NMR δ (DMSO-d₆ 350K) 1.2–1.6 (8H, m, 4×CH₂), 2.56 (2H, t, J=7.6 Hz, PhCH₂), 2.86(4H, m, NCH₃, H₃), 3.02–3.26 (m, NCH₂CH₂, H₃), 3.81–4.4 (4H, m, SOCH₂, NCH₂C=O), 4.81, 4.90 (1H, 2×m, H₄), 7.12–7.35 (10H, m, 2×Ph-H), Found: C, 65.4; H, 6.9; N, 6.3%; C₂₅H₃₂N₂O₃S requires: C, 68.1; H, 7.3: N, 6.4%.

EXAMPLE 43

(4R,SS/4S,SR) N-Methyl-N-(6phenylhexyl)-(4-benzylsulphinyl-2-oxoazetidin-1-yl)acetamide Colourless oil, 13% yield, ¹H nmr δ (DMSO-d₆ 350K) 1.2–1.6 (8H, m, 4×CH₂), 2.56 (2H, t, J=7.6 Hz, PhCH₂), 2.86 (4H, m, NCH₃, H₃), 3.1–3.3 (m, NCH₂, H₃), 4.01 (2H, m, SOCH, NCHC=O), 4.17 (1H, d, J=12.9 Hz, SOCH), 4.37 (2H, d, J=17.4 Hz, NCHC=O), 4.81 (1H, m, H₄), 7.13–7.35 (1H, m, 2×Ph-H), Found: C, 65.3; H, 6.8; N, 6.1%; C₂₅H₃₂N₂O₃S requires: C, 68.1; H, 7.3: N, 6.4%.

EXAMPLE 44

N-[6-(3,5-di-tert-butyl-4-hydroxyphenyl)hexyl]-(4-benzylthio-2-oxoazetidin-1-yl)acetamide Yellow oil, 83% yield, ¹H NMR δ (CDCl₃) 1.3–1.6 (26H, m, 4×CH₂+6×CH₃), 2.50 (2H, t, J=8 Hz, CH₂Ph), 2.95 (1H, dd, J=2, 15 Hz, H₃), 3.25 (2H, q, J=7 Hz, NHCH₂), 3.37 (1H, dd, J=5, 15 Hz, H₃), 3.55, 3.71 each 1H, d, J=17 Hz, NCH₂), 3.82 (2H, s, SCH₂), 4.80 (1H, m, H₄), 5.03 (1H, s, OH), 6.02 (1H, br s, NH), 6.96 (2H, s, HOPh-H), 7.3 (5H, m, Ph-H).

EXAMPLE 45

(4R,SS/4S,SR) N-[6-(3,5-Di-tert-butyl-4-hydroxyphenyl)hexyl]-(4-benzylsulphinyl-2-oxoazetidin-1-yl)acetamide Light brown glass, 33% yield, ¹H NMR δ (CDCl₃) 1.3–1.7 (26H, m 4×CH₂+6×CH₃), 2.50 (2H, t, J=8 Hz, CH₂Ph), 2.88 (1H, dd, J=2, 15 Hz, H₃), 3.17 (1H, dd, J=5, 15 Hz, H₃), 3.3 (2H, m, NHCH₂), 3.89, 4.25 (each 1H, d, J=17 Hz, NCH₂), 3.99, 4.19 (each 1H, d, J=13 Hz, SOCH₂), 4.61 (1H, m, H₄), 5.02 (1H, s, OH), 6.96 (2H, s, HOPh-H), 7.25 (1H, br s, NH), 7.3–7.5 (5H, m, Ph-H), Found: C, 68.9; H, 8.3; N, 5.0%; C₃₂H₄₆N₂O₄S requires: C, 69.3; H, 8.4; N, 5.0%.

EXAMPLE 46

N-6-(4-methoxyphenyl)hexyl-(4-benzylthio-2-oxoazetidin-1-yl)acetamide

Yellow oil, 77% yield, ¹H NMR δ (CDCl₃) 1.3–1.6 (8H, m, 4×CH₂), 2.54 (2H, t, J=15 Hz, CH₂PhOCH₃), 2.95 (1H, dd, J=2.15 Hz, H₃), 3.23 (2H, m, NHCH₂), 3.37 (1H, dd, J=5, 15 Hz, H₃), 3.55, 3.71 (each 1H, d, J=17 Hz, NCH₂), 3.78 (3H, s, OCH₃), 3.81 (2H, s, SCH₂), 4.80 (1H, m, H₄), 6.01 (1H, br s, NH), 6.82, 7.07 (each 2H, d, J=8.5 Hz, CH₃OPh-H), 7.3 (5H, m, Ph-H).

EXAMPLE 47

(4S,SR/4S,SS) N-6-(4-methoxyphenyl)hexyl-(4-benzylsulphinyl-2-oxoazetidin-1-yl)acetamide White solid, 10% yield, mp 129–133.5° C., ¹H NMR δ (CDCl₃) 1.25–1.56(8H, m, CH₂CH₂CH₂CH₂), 2.52(2H, t, J=7.25 Hz, CH₂Ph-OMe), 2.94 (1H, dd, J=14.75, 4.5 Hz, H₃ᵦ), 3.20(2H, m, NHCH₂), 3.45(1H, dd, J=14.75, 2.0 Hz, H₃ₐ), 3.71, 4.23(2H, dd, J=15.5, 15.5 Hz, SOCH₂Ph) 3.78 (3H, s, OCH₃), 3.88, 4.04(2H, dd, J=13.0, 12.75 Hz, N—CH₂), 4.53(1H, m, H₄), 6.66(1H, s, NH), 6.78–6.83, 7.06–7.09(2H,2H, m, CH₂-Ph-OMe), 7.22–7.26, 7.36–7.40 (3H,2H, m, SOCH₂Ph). Found: B, 64.9; H, 6.6; N, 6.1%; C₂₅H₃₂N₂O₄S requires: C, 65.8; H, 7.1; N, 6.1%.

EXAMPLE 48

(4R,SS/4S,SR) N-6-(4-methoxylphenyl)hexyl-(4-benzylsulphinyl-2-oxoazetidin-1-yl)acetamide Pale yellow solid, 29% yield, mp 85–88° C., 1H NMR δ (CDCl3) 1.23–1.63(8H, m, CH₂CH₂CH₂CH₂), 2.53(2H, t, J=7.25 Hz, CH₂Ph), 2.88(1H, dd, J=15.25, 2.5 Hz,H₃ₐ), 3.13–3.31(3H, m, NHCH₂,H₃ᵦ), 3.78(3H, s, OCH₃), 3.84–4.28 (4H, m NCH₂, SOCH₂Ph), 4.61(1H, m, H₄), 6.78–6.84, 7.05–7.10(2H,2H, m, CH₂-Ph-OMe), 7.18(1H, s, CONH), 7.23–7.27, 7.37–7.44(3H,2H, m, SOCH₂Ph). Found: C, 65.5; H, 6.8; N, 6.0%; C₂₅H₃₂N₂O₄S requires: C, 65.8; H, 7.1; N, 6.1%.

EXAMPLE 49

N-(6-(4-chlorophenyl)hexyl)-(4-benzylthio-2-oxoazetidin-1-yl)acetamide

Pale yellow solid, 89% yield, mp 60–62° C. ¹H NMR δ (CDCl₃) 1.3–1.6 (8H, m, 4×CH₂), 2.55 (2H, t, J=7.6 Hz, PhCH₂), 2.90, 2.97 (1H, dd, J=2.4, 15.4 Hz, H₃), 3.3 (2H, m, NHCH₂), 3.33, 3.40 (1H, dd, J=5.2, 15.4 Hz, H₃), 3.56, 3.71 (each 1H, d, J=16.8 Hz, NCH₂), 3.81 (2H, s, SCH₂), 4.81 (1H, m, H₄), 6.05 (1H, m, NH), 7.05–7.36 (1H, m, 2×Ph-H).

EXAMPLE 50

(4S,SR/4S,SS) N-(6-(4-chlorophenyl)hexyl)-(4-benzylsulphinyl-2-oxoazetidin-1-yl)acetamide Colourless solid 17% yield, mp 178–179° C. ¹H NMR δ (CDCl₃) 1.2–1.6 (8H, m, 4sCH₂), 2.55 (2H, t, J=7.6 Hz, PhCH₂), 2.93, 2.99 (1H, dd, J=4.7, 14.8 Hz, H₃), 3.22 (2H, m, NHCH₂), 3.44, 3.49 (1H, dd, J=2.2 14.8 Hz, H₃), 3.68, 4.13 (each 1H, d, J=17.4 Hz, NCH₂), 3.87, 4.05 (each 1H, d, J=13.2 Hz, SOCH₂), 4.50 (1H, m, H₄), 6.65 (1H, m, NH), 7.07–7.40 (9H, m, 2sPh-H), Found: C, 62.5; H, 6.3; N, 6.3%; C₂₄H₂₉ClN₂O₃S requires: C, 62.5; H, 6.3; N, 6.1%.

EXAMPLE 51

(4R, SS/4S,SR) N-(6-(4-chlorophenyl)hexyl-(4-benzylsulphinyl-2-oxoazetidin-1-yl)acetamide Colourless solid, dias. ratio 1:9, 39% yield, mp 103–104° C. ¹H NMR (CDCl₃) δ1.3–1.6 (8H, m, 4×CH₂), 2.56 (2H, t, J=7.6 Hz, PhC$\underline{H}_2$), 2.87, 2.90 (1H, dd, J=2.5, 15.3 Hz, $\underline{H}_3$), 3.16, 3.20 (each 1H, d, J=5.3 15.3 Hz, $\underline{H}_3$), 3.26 (2H, m, NHC$\underline{H}_2$), 3.87, 4.25 (each 1H, d, J=17.2 Hz, NC$\underline{H}_2$), 3.98, 4.19 (each 1H, d, J=13 Hz, SOC$\underline{H}_2$), 4.6 (1H, m, $\underline{H}_4$), 7.07–7.41 (10H, m, 2sPh-$\underline{H}$, N$\underline{H}$), Found: C, 62.5; H, 6.3; N, 6.2%; $C_{24}H_{29}ClN_2O_3S$ requires: C, 62.5; H, 6.3; N, 6.1%.

EXAMPLE 52

N-(6-(3,5-dichlorophenyl)hexyl)-(4-benzylthio-2-oxoazetidin-1-yl)acetamide

Pale yellow oil, 69% yield, $^1$H NMR δ (CDCl$_3$) 1.30–1.60 (m, 4sC$\underline{H}_2$), 2.57 (2H, t, J=7.63 Hz, ArC$\underline{H}_2$), 2.95 (1H, dd, J=2.4 15.4 Hz, $\underline{H}_{3a}$) 3.24 (1H, m, NHC$\underline{H}_2$), 3.38 (1H, dd, J=5.13, 15.4 Hz, $\underline{H}_{3b}$), 3.64 (2H, dd, J=16.8 Hz, COC$\underline{H}_2$N), 3.81 (2H, s, ArC$\underline{H}_2$S), 4.81 (1H, m, J=2.5 Hz, 5.0 Hz, $\underline{H}_4$) 6.0 (1H, m, N$\underline{H}$C=O), 7.0–6.36 (9H, m, 9xAr$\underline{H}$).

EXAMPLE 53

(4R,SR/4S,SS) N-(6-(3,5-dichlorophenyl)hexyl)-(4-benzylsulphinyl-2-oxoazetidin-1-yl)acetamide White solid, dias. ratio 36:1, yield 37%, mp 158–159° C. Found: C, 58.2; H, 5.7; N, 5.7%; $C_{24}H_{28}Cl_2N_2O_3S$ requires: C, 58.2; H, 5.7; N, 5.7%.

EXAMPLE 54

(4R,SS/4S,SR) N-(6-(3,5-dichlorophenyl)hexyl)-(4-benzylsulphinyl-2-oxoazetidin-1-yl)acetamide White solid, dias. ratio 1:9, yield 22%, mp 108–109° C. Found: C, 58.2; H, 5.6; N, 5.7%; $C_{24}H_{28}Cl_2N_2O_3S$ requires: C, 58.2; H, 5.7; N, 5.7%.

EXAMPLE 55

N-6-(3-chlorophenyl)hexyl)-(4-benzylthio-2-oxoazetidin-1-yl)-acetamide

Pale yellow oil, 75% yield $^1$NMR δ (CDCl$_3$) 1.30–1.60 (8H, m, 4×C$\underline{H}_2$), 2.55 (2H, t, J=7.63 Hz, ArC$\underline{H}_2$), 2.95(1H, dd, J=2.5, 15.5 Hz, $\underline{H}_{3a}$), 3.24 (2H, m, J=17.5 Hz, NHC$\underline{H}_2$), 3.38 (1H, dd, J=5.25, 15.25 Hz, $\underline{H}_{3b}$), 3.64 (2H, dd, J=16.87 Hz, COC$\underline{H}_2$N), 3.82 (2H, s, ArC$\underline{H}_2$S), 4.81 (1H, m, $\underline{H}_4$), 6.06 (1H, m, N$\underline{H}$), 7.0–7.36 (8H, m, 8×Ar$\underline{H}$)

EXAMPLE 56

(4R,SR/4S,SS) N-(6-(3-chorophenyl)hexyl)-4-benzylsulphinyl-2-oxoazetidin-1-yl)acetamide White solid, dias. ratio 36:1, yield 18%, mp 147–148° C. Found: C,62.3; H,6.1; N,6.2%; $C_{24}H_{29}ClN_2O_3S$ requires: C,62.5, H,6.3; N,6.1%

EXAMPLE 57

(4R,SS/4S,SR) N-(6-(3-chlorophenyl)hexyl)-4-(benzylsulphinyl-2-oxoazetidin-1-yl)acetamide White solid, dias. ratio 14:86, yield 49%, mp 74–75° C. Found C,62.4; H,6.2, N,6.1%; $C_{24}H_{29}ClN_2O_3S$ requires: C,62.5; H,6.3; N,6.1%

EXAMPLE 58

N-6-(4-hydroxyphenyl)hexyl-(4-benzylthio-2-oxoazetidin-1-yl)-acetamide

Yellow oil 23% yield $^1$H NMR δ (CDCl$_3$) 1.2–1.7 (8H, m, 4×C$\underline{H}_2$), 2.52 (2H, t, J=15 Hz, C$\underline{H}_2$PhOH), 2.95 (1H, dd, J=2, 15 Hz, $\underline{H}_3$), 3.21 (2H, m, NHC$\underline{H}_2$), 3.37 (1H, dd, J=5, 15 Hz, $\underline{H}_3$), 3.53, 3.72(each 1H, d, J=17 Hz, NC$\underline{H}_2$), 3.76 (2H, s, SC$\underline{H}_2$), 4.83 (1H, m, $\underline{H}_4$), 5.37 (1H, s, O$\underline{H}$), 5.97 (1H, br s, N$\underline{H}$), 6.75, 7.02 (each 2H, d, J=8.5 Hz, HOPh—$\underline{H}$), 7.3 (5H, m, Ph—$\underline{H}$)

EXAMPLE 59

(4R,SR/4S,SS) and (4R,SS/4S,SR) N-6-(4-hydroxyphenyl)hexyl-(4-benzylsulphinyl-2-oxoazetidin-1-yl)acetamide White glassy solid, dias. ratio b 1:2, 79% yield, mp 38–49° C. $^1$H NMR δ (CDCl$_3$) 1.25–1.58 (16H, m, 2×C$\underline{H}_2$C$\underline{H}_2$C$\underline{H}_2$), 2.52 (4H, t, J=7.0 Hz, 2×C$\underline{H}_2$Ph), 2.83 (1H, dd, J=15.0, 2.0 Hz, $\underline{H}_{3a}$), 2.90 (1H, dd, J=15.0, 5.0 Hz, $\underline{H}_{3b}$), 3.12–3.25 (5H, m, 2×NHC$\underline{H}_2$, $\underline{H}_{3b}$), 3.40 (1H, dd, J=15.0, 2.5 Hz, $\underline{H}_{3a}$), 3.72–4.21 (8H, m, 2×SOC$\underline{H}_2$Ph, 2×N—C$\underline{H}_2$), 4.56 (1H, m, $\underline{H}_4$), 4.64 (1H, m, $\underline{H}_4$), 6.08 (1H, s, O$\underline{H}$), 6.17 (1H, s, O$\underline{H}$) 6.63 (1H, m, N$\underline{H}$), 6.71–6.77, 6.97–7.04 (4H, 5H, m,2×C$\underline{H}_2$P$\underline{h}$—OH, N$\underline{H}$), 7.22–7.29,7.35–7.39 (4H, 6H, m, 2×SOC$\underline{H}_2$P$\underline{h}$). Found: C, 63.47; H,6.53; N,6.24%; $C_{24}H_{30}N_2O_4S$ requires: C,65.13; H,6.83; N,6.33%

EXAMPLE 60

N-(6-Phenylhexyl)-(4-(4-ethoxycarbonyl)benzylthio-2-oxoazetidin-1-yl)acetamide a. 4-(4(Ethoxycarbonyl)benzylthio)azetidin-2-one Yellow oil, 62% yield 1H NMR δ (CDCl$_3$) 1.40 (3H, t, J=7.13 Hz, O—CH$_2$CH$_3$), 2.85 (1H, dd, coupling indeterminate, H$_{3a}$), 3.31 (1H, dd, coupling indeterminate, H$_{3b}$) 3.88 (2H, s, S—C$\underline{H}_2$), 4.38 (2H, q, J=7.13 Hz, O—C$\underline{H}_2$CH$_3$), 6.10 (1H, br. singlet, N—$\underline{H}$), 7.40 (2H, d, J=8.36 Hz, Ph—$\underline{H}$), 8.01 (2H, d, J=8.34 Hz, Ph—$\underline{H}$)

b. N-(6-phenylhexyl)-(4-(4-ethoxycarbonyl)benzylthio-2-oxoazetidin-1-yl)acetamide Colourless oil, 59% yield 1H NMR δ (CDCl$_3$) 1.23–1.71 (13H, m, C$\underline{H}_2$C$\underline{H}_2$, OCH$_2$C$\underline{H}_3$), 2.56–2.62 (2H, m, Ph—C$\underline{H}_2$), 2.93 (1H, dd, coupling indeterminate, H$_{3a}$), 3.18–3.27 (2H, m, NH—C$\underline{H}_2$), 3.38 (1H, dd, J=15.37, 5.14 Hz, H$_{3b}$), 3.52 and 3.80 (1H each, d, J=16.64 Hz, N—C$\underline{H}_2$), 4.37 (2H, q, J=7.13 Hz, O—C$\underline{H}_2$CH$_3$), 4.85 (1H, dd, coupling indeterminate, H$_4$), 6.01 (1H, br. triplet, N—$\underline{H}$), 7.14–7.29 (5H, m, Ph—$\underline{H}$), 7.39 (2H, d, J=8.34 Hz, Ph—$\underline{H}$), 8.00 (2H, d, J=8.30 Hz, Ph—$\underline{H}$).

EXAMPLE 61

(4R,SS/4S,SR) N-(6-Phenylhexyl)-4-(4-ethoxycarbonyl)benzylsulphinyl-2-oxoazetidin-1-yl) acetamide White crystalline solid, 25% yield, mp 101–103° C. Found: C, 64.69; H, 6.64; N, 5.72% $C_{27}H_{34}N_2O_5S$ requires: C, 65.04; H, 6.87, N, 5.62%

EXAMPLE 62

N-(6-phenylhexyl)-4(4-chlorobenzylthio)-2-oxoazetidin-1-ylacetamide a. 4-(4-Chlorobenzylthio)azetidinone Crystalline solid, 72% yield, mp 73–74° C. 1H NMR δ (CDCl$_3$) 2.86 (1H, m, H$_{3a}$), 3.32 (1H, m, H$_{3b}$), 3.81 (2H, s, S—C$\underline{H}_2$), 4.68 (1H, dd, J=5.07, 2.46 Hz, H$_4$), 6.04 (1H, br. singlet, N—$\underline{H}$), 7.24–7.33 (4H, m, Ph—$\underline{H}$).

b. N-(6-phenylhex-1-yl)-4(4-chlorobenzylthio)-2-oxoazetidin-1-ylacetamide

Colourless oil, 41% yield 1H NMR δ (CDCl$_3$) 1.28–1.35 (4H, m, C$\underline{H}_2$C$\underline{H}_2$), 1.40–1.51 (2H, m, C$\underline{H}_2$), 1.53–1.60 (2H, m, C$\underline{H}_2$), 2.60 (2H, t, J=7.65 Hz, Ph=C$\underline{H}_2$), 2.92 (1H, dd, J=16.37, 2.40 Hz, H$_{3a}$), 3.23 (2H, dt, 4 lines, NH—C$\underline{H}_2$), 3.38 (1H, dd, J=15.36, 5.16 Hz, H$_{3b}$), 3.54 and 3.82 (1H each, d, J=16.65 Hz, N—C$\underline{H}_2$), 3.78 (2H, s, S—C$\underline{H}_2$), 4.83 (1H, dd, J=5.15, 2.43 Hz, H$_4$), 7.14–7.30 (9H, m, Ph—$\underline{H}$).

EXAMPLE 63

(4R,SR/4S,SS) N-(6-phenylhex-1-yl)-4-(4-chlorobenzylsulphinyl)-2-oxoazetidin-1-ylacetamide White crystalline solid, mp. 155–156° C., 10% yield Found: C, 62.2; H, 6.2; N, 6.1%; C$_{24}$H$_{29}$ClN$_2$O$_3$S requires: C, 62.5; H, 6.3; N, 6.1%

EXAMPLE 64

(4R,SS/4S,SR) N-(6-phenylhex-1-yl)-4-(4-chlorobenzylsulphinyl)-2-oxoazetidin-1-ylacetamide mp 92–93° C., 33% yield Found: C, 62.4; H, 6.3; N, 6.1%, C$_{24}$H$_{29}$ClN$_2$O$_3$S requires: C, 62.5; H, 6.3; N, 6.1%

EXAMPLE 65 trans N-(6-Phenylhexyl)-(4-benzylthio-3-methyl-2-oxoazetidin-1-yl)acetamide

Colourless oil, 65% yield 1H NMR δ (CDCl$_3$) 1.2–1.7 (11H, m, 4×C$\underline{H}_2$+C$\underline{H}_3$), 2.59 (2H, t, J=7 Hz, C$\underline{H}_2$Ph), 3.2 (3H, m, NHC$\underline{H}_2$+$\underline{H}_3$), 3.50, 3.70 (each 1H, d, J=17 Hz, NC$\underline{H}_2$), 3.80 (2H, s, SC$\underline{H}_2$), 4.42 (1H, d, J=2 Hz, $\underline{H}_4$), 6.04 (1H, br s, N$\underline{H}$), 7.1–7.4 (10H, m, 2×Ph—$\underline{H}$)

EXAMPLE 66 trans N-(6-Phenylhexyl)-(4-benzylsulphinyl-3-methyl-2-oxoazetidin-1-yl)acetamide White, semi-solid, dias. ratio 4:6, 85% yield 1H NMR δ (CDCl$_3$) 1.1–1.7 (11H, m, 4×C$\underline{H}_2$+C$\underline{H}_3$), 2.59 (2H, m, C$\underline{H}_2$Ph), 3.25 (2.6H, m, NHC$\underline{H}_2$+$\underline{H}_3$), 3.7–4.3(3.4H, m, SOC$\underline{H}_2$+$\underline{H}_4$+$\underline{H}_3$'), 6.65 (0.6H, br s, N$\underline{H}$), 7.1–7.4 (10.4 m, 2×Ph—$\underline{H}$+N$\underline{H}$'). Found: C, 67.2; H, 7.3; N, 6.0%; C$_{25}$H$_{32}$N$_2$O$_3$S requires: C, 68.2; H, 7.3; N, 6.4%

The following compounds (Examples 67 to 69) were prepared by oxidation of the corresponding sulfides described above using the general procedure of Example 4.

EXAMPLE 67

N-(6-phenylhexyl)-4-benzylsulphonyl-2-oxoazetidin-1-yl)acetamide

White solid, 65% yield, mp 104–105° C. Found: C, 64.7; H, 6.6; N, 6.3%, C$_{24}$H$_{30}$N$_2$O$_4$S requires: C, 65.1; H, 6.8; N, 6.3%

EXAMPLE 68

N-(6-(3,5-dichlorophenyl)hexyl)-(4-benzylsulphonyl-2-oxoazetidin-1yl)acetamide

White solid, 90% yield, mp 115–116° C. Found: C, 55.2; H, 5.4; N, 5.4%; C$_{24}$H$_{28}$Cl$_2$N$_2$O$_4$S.0.65H$_2$O requires: C,55.1; H, 5.6, N, 5.4%

EXAMPLE 69

N-(6-(3-chlorophenyl)hexyl)-(4-benzylsulphinyl-2-oxoazetidin-1-yl)acetamide

White solid, 3% yield, mp 95–98° C. Found: C, 61.0; H, 6.2; N, 6.0%; C$_{24}$H$_{29}$ClN$_2$O$_4$S.0.12C$_6$H$_{14}$ requires: C, 60.9; H, 6.3; N, 5.8%

EXAMPLE 70

4-(Benzylthio)-1-(3-phenylpropyl)azetidin-2-one

A solution of 4-(benzylthio)azetidin-2-one (1.1 g, 5.5 mmol) in dry THF (10 ml) was added dropwise over 10 minutes to a suspension of NaH (0.13 g, 5.6 mmol) in dry THF (5 ml) at −20° C. under a N$_2$ atmosphere. A solution of 3-phenyl-1-(trifluoromethanesulfonyloxy)propane (1.5 g, 5.6 mmol) in dry THF (10 ml) was added dropwise over 10 minutes at −55° C. After stirring for 1 hour, the mixture was poured into ice/water (50 g), filtered through hyflo, the THF evaporated under reduced pressure and the residue taken up in ethyl acetate. The solution was washed with brine (×2), dried (MgSO$_4$), evaporated under reduced pressure and purified by flash chromatography on silica gel eluted with 5:1 petroleum ethe:methyl acetate to give the title compound as a yellow oil (1.4 g, 81%). $^1$H NMR δ (CDCl$_3$) 2.58 (2H, m, C$\underline{H}_2$), 2.58 (2H, t, J=15 Hz, C$\underline{H}_2$Ph), 2.9, 3.2 (each 2H, m, $\underline{H}$-3 & NC$\underline{H}_2$), 3.73 (2H, s, SC$\underline{H}_2$), 4.51 (1H, m, $\underline{H}$-4), 7.2 (10H, m, 2×Ph—$\underline{H}$)

EXAMPLE 71

(4R,SR/4S,SS) 4-Benzylsulphinyl-1-(3-phenylpropyl)azetidin-2-one

Prepared from 4-(benzylthio)-1-(3-phenylpropyl) azetidin-2-one using the general procedure of Example 2. The product was obtained as a white solid, dias. ratio 97:3, 19% yield, mp 93–96° C. $^1$H NMR δ (CDCl$_3$) 1.83–1.94 (2H,m,CH$_2$C$\underline{H}_2$CH$_2$), 2.57–2.69(2H,m,C$\underline{H}_2$Ph), 2.76(1H, dd,J=14.5,4.5 Hz,H$_{3b}$), 3.22–3.39(3H,m,N—C$\underline{H}_2$H$_{3a}$), 3.83, 3.98 (2H, dd, J=13.0,13.0 Hz,SOC$\underline{H}_2$Ph), 4.22(1H,m,$\underline{H}_4$), 7.13–7.41(10H,m,C$\underline{H}_2$Ph,SOC$\underline{H}_2$Ph). Found: C,69.5; H,6.5; N,4.5%; C$_{19}$H$_{21}$NO$_2$S requires: C,69.7; H,6.5; N,4.3%

EXAMPLE 72

(4R,SS/4S,SR) 4-Benzylsulphinyl-1(3-phenylpropyl)azetidin-2-one

The mother liquors obtained from the above crystallisation were re-worked to give the title compound as a pale green oil, dias. ratio 80:20, 14% yield $^1$H NMR δ (CDCl$_3$) 1.90–2.04(2H, m, CH$_2$CH$_2$CH$_2$), 2.41(1H, dd, J=15.0, 2.4 Hz, H$_{3a}$), 2.59–2.64 (2H, m, CH$_2$Ph), 2.84 (1H, dd, J=15.0, 5.0 Hz, H$_{3b}$), 3.41–3.49 (2H, m, N—CH$_2$), 3.94–4.05 (2H, dd, J=13.0, 13.0 Hz, SOCH$_2$Ph), 4.23–4.26 (1H, m, H$_4$), 7.51–7.39 (10H, m, SOCH$_2$Ph, CH$_2$Ph). Found: C,66.0; H,6.4; N,3.3%; C$_{19}$H$_{21}$NO$_2$S requires: C,69.7; H,6.5; N,4.3%

The following compounds (Examples 73–75) was prepared using the general procedures of Examples 70–72.

EXAMPLE 73

4-Benzylthio-1-(2-phenethyl)azetidin-2-one

Light brown oil, 60% yield 1H NMR δ (CDCl$_3$) 2.8–2.9 (3H, m, C$\underline{H}_2$Ph+$\underline{H}_3$), 3.1, 3.5 (each 1H, m, NC$\underline{H}_2$), 3.18 (1H, dd, J=5, 15 Hz, $\underline{H}_3$), 3.66 (2H, dd, J=14 Hz, SC$\underline{H}_2$), 4.35 (1H, m, $\underline{H}_4$), 7.1–7.4 (10H, m, 2×Ph—$\underline{H}$)

EXAMPLE 74

(4R,SR/4S,SS) 4-Benzylsulphinyl-1-(2-phenethyl) azetidin-2-one

Colourless solid, 16% yield, mp 98–101° C. 1H NMR δ (CDCl$_3$) 2.71 (1H, dd, J=2, 15 Hz, $\underline{H}_3$), 2.88 (2H, t, J=7 Hz, CH₂Ph), 3.29 (1H, dd, J=2, 15 Hz, H₃), 3.3 (1H, m, NCH₂), 3.7–3.9 (3H, m, NCH₂+SOCH₂), 3.9 (1H, m, H₄), 7.1–7.4 (10H, m, Ph—H) Found: C, 68.7; H, 6.1; N, 4.5%; C₁₈H₁₉NO₂S requires: C, 69.0; H, 6.1; N, 4.5%

EXAMPLE 75

(4S,SS/4S,SR) 4-Benzylsulphinyl-1(2-phenethyl)azetidin-2-one

Colourless solid, 27% yield, mp 88–9° C. 1H NMR δ (CDCl₃) 2.40 (1H, dd, J=2, 15 Hz, H₃), 2.85 (1H, dd, 5, 15 Hz, H₃), 3.0 (2H, m, CH₂CH₂Ph), 3.62, 3.76 (each 1H, m, NCH₂), 3.92, 4.03 (each 1H, d, SOCH₂), 4.16 (1H, m, H₄), 7.2–7.4 (10H, m, Ph—H) Found: C, 68.8; H, 6.2; N, 4.7%, C₁₈H₁₉NO₂S requires: C, 69.0; H, 6.1; N, 4.5%

EXAMPLE 76

4-(Benzylthio)-1-(4-phenylbutyl)azetidin-2-one

A solution 4-(benzylthio)azetidin-2-one (1.1 g, 5.5 mmol) in dry THF (10 ml) was added dropwise over 10 minutes to a suspension of NaH (0.13 g, 5.6 mmol) in dry THF (5 ml) at −20° C. under a N₂ atmosphere. A solution of 1-iodo-4-phenylbutane (1.4 g, 5.5 mmol) in dry THF (10 ml) was added dropwise over 10 minutes at −55° C. After stirring for 18 hours, the mixture was poured onto ice/water (50 g), filtered through hyflo, the THF evaporated under reduced pressure and the residue taken up in ethyl acetate. The solution was washed with brine (×2), dried (MgSO₄), evaporated under reduced pressure to a yellow oil which was purified by flash chromatography on silica gel eluted with 5:1, 3:1 then 1:1 petroleun ether/ethyl acetate to give the product as a yellow oil (0.25 g, 14%). ¹H NMR δ (CDCl₃) 1.5 (4H, m, 2×CH₂), 2.6 (2H, m, CH₂Ph), 2.85, 3.2 (each 2H, m, H-3 & NCH₂), 3.73 (2H, s, SCH₂), 4.54 (1H, m, H-4), 7.2 (10H, m, 2×Ph—H)

EXAMPLE 77

(4R,SS/4S,SR) 4-Benzylsulphinyl-1-(4-phenylbutyl)azetidin-2-one

Prepared from 4-(benzylthio)-1(4-phenylbutyl)azetidin-2-one using the general procedure of Example 30. The product was obtained as a yellow oil following flash chromatography, 76% yield ¹H NMR δ (CDCl₃) 1.61–1.66 (8H,m,2×CH₂CH₂CH₂CH₂), 2.47(1H,dd,J=15.0, 1.50 Hz, H₃ₐ), 2.60(4H,m,2×CH₂Ph), 2.83(1H,dd,J=14.5,4.5 Hz, H₃ᵦ), 2.93(1H,dd, J=15.0,5.0 Hz,H₃ᵦ), 3.29–3.50(5H,m,2× N—CH₂,H₃ₐ), 3.98,4.06(2H,dd,J=13.25, 13.25 Hz,SOCH₂Ph), 3.83,3.93(2H,dd,J=6.25,6.25 Hz,SOCH₂Ph), 4.28 (1H,m,H₄), 4.31(1H,m,H₄), 7.12–7.39(20H,m,2×CH₂Ph,2×SOCH₂Ph). Found: C,59.2; H,6.9; N,4.5%; C₂₀H₂₃NO₂S requires: C,70.2; H,6.8; N,4.1%

EXAMPLE 78 p-Methoxybenzyl [(3S, 4R)-4-benzylthio-3-bromo-2-oxoazetidin-1-yl]acetate a. p-Methoxybenzyl [(3S, 4R)-4-acetylthio-3-bromo-2-oxoazetidin-1-yl]acetate Ozonised oxygen was bubbled through a solution of p-methoxybenzyl 2[(3S, 4R)-4-acetylthio-3-bromo-2-oxoazetidin-1-yl]-3-methylbut-2-enoate (Osborne N. F. et al., J. Chem. Soc. Perkin Trans. 1, 1994, 179) (20.16 g, 0.0456 mol) in ethyl acetate (400 ml) at −65° to −70° C. until a permanent blue solution was obtained. Excess ozone was removed by the passage of oxygen, then trimethyl phosphite (53.8 ml, 0.456 mol) was added dropwise. After 15 min. the solution was allowed to warm to room temperature, then stood for 16 hr. The solvents were evaporated and the residue reevaporated twice from toluene, then dissolved in ethyl acetate (300 ml) and stirred vigorously for 1.5 hr. with a solution of p-toluenesulphonic acid (2 g) in water (100 mol). After dilution with water the organic layer was separated and the aqueous layer further extracted with ethyl acetate. The combined extracts were washed successively with saturated aq. sodium hydrogen carbonate and brine, then dried ((MgSO₄) and evaporated. Purification by flash chromatography (silica, ethyl acetate-pet. ether) gave the product as a light brown oil, yield 10.6 g (58%).

b. Silver (3S,4R)-3-bromo-1-(p-methoxybenzyloxycarbonylmethyl)-2-oxoazetidine-4-thiolate A solution of p-methoxybenzyl [(3S, 4R)-4-acetylthio-3-bromo-2-oxoazetidin-1-yl]acetate (4.13 g, 0.01 mol) in methanol (90 ml) was added with stirring in subdued light to a solution of silver nitrate (2.27 g, 0.0133 mol) in methanol (90 ml). Triethylamine (1.87 ml, 0.0133 mol) was then added with ice cooling, and stirring continued for 1 hr. at 5–10° C. followed by 30 min. at room temperature. The mixture was re-cooled (ice bath) and the precipitated solid filtered and washed twice with ice cold methanol then hexane to give the title compound, yield, 4.6 g (96%).

c. p-Methoxybenzyl [(3S, 4R)-4-benzylthio-3-bromo-2-oxoazetidin-1-yl]acetate

A solution of silver (3S,4R)-3-bromo-1-(p-methoxybenzyloxycarbonylmethyl)-2-oxoazetidine-4-thiolate (4.6 g, 0.0099 mol) in acetonitrile (100 ml) was treated with benzyl bromide (1.76 ml, 0.015 mol) under nitrogen and the mixture stirred in subdued light for 48 hr. The solvent was evaporated, the residue treated with dichloromethane and the precipitated salts filtered off. The filtrate was evaporated and the residue purified by flash chromatography (silica, ethyl acetate-pet. ether) to give the title compound as an oil, yield 3.37 g (76%). 1H NMR δ (CDCl₃), 3.39, 4.02 (each 1H, d, J=18.1 Hz, NCH₂), 3.76 (2H, s, SCH₂), 3.81 (3H, s, OCH₃), 4.61, 4.91 (each 1H, d, J=1.6 Hz, H₃+H₄), 5.08 (2H, m, OCH₂), 6.89 (2H, m, 3.5-(4-CH₃OPh)-H), 7.22–7.33 (7H, m, Ph—H+2.6-(4-CH₃OPh)—H).

EXAMPLE 79

(3S,4R)-N-(6-phenylhexyl)-1-(4-benzylthio-3-bromo-2-oxoazetidin-1-yl)acetamide a) p-Methoxybenzyl 2[(3S, 4R)-4-benzylthio-3-bromo-2-oxoazetidin-1-yl]-3-methybut-2-enoate A solution of the silver salt of p-methoxybenzyl 2-[(3S, 4R)-4-mercapto-3-bromo-2-oxoazetidin-1-yl]-3-methylbut-2-enoate (10 g, 20 mmol) in dry acetonitrile (100 ml) was treated with benzyl bromide (4 g, 24 mmol) and the resulting mixture refluxed for 30 mins. the reaction was cooled to room temperature, filtered, evaporated to dryness and the residue purified by flash chromatography using 1:1 ether: pentane as the eluting solvent. Evaporation of the appropriate fractions gave the product as a white solid (5.8 g, 59%), mp 70–72° C. ¹H NMR δ (CDCl₃)1.93 (3H, s, CH₃), 2.23 (3H, s, CH₃), 3.66 (1H, dd, J=2.9, 17.5 Hz, SCH₂), 3.79 (3H, s, OCH₃), 4.52 (1H, d, J=1.8 Hz, H₃), 4.95 (1H, d, J=1.9 Hz, H₄), 5.08 (2H, q, J=12.0 Hz, CO₂CH₂), 6.84–6.90 (2H, m, 2.6Ph—H), 7.13–7.31 (7H, m, 3,5Ph—H,Ph—H).

b) (3S, 4R)-4-Benzylthio-3-bromoazetidin-2-one

Ozonised oxygen was bubbled through a solution of p-methoxybenzyl 2-[(3S, 4R)-4-benzylthio-3-bromo-2-oxoazetidin-1-yl]-3-methylbut-2-enoate (2 g, 4 mmol) in dichloromethane (40 ml) at −78° C. and the reaction monitored by infra-red spectroscopy. When the band at 1780 cm$^{-1}$ had disappeared, methanol (4 ml) together with a trace of sodium methoxide and dimethyl sulfide (1 ml) was added and stirring continued at room temperature for 16 h. The reaction was evaporated and the residue purified by flash chromatography using 1:1 ether:pentane as the eluting solvent. Evaporation of the appropriate fractions gave the product as a colourless oil (0.7 g, 64%). $^1$H NMR δ (CDCl$_3$) 3.87 (2H, s, SC$\underline{H}_2$), 4.52 (1H, m, $\underline{H}_4$), 4.69 (1H, d, $\underline{H}_3$) 5.85 (1H, bs, N$\underline{H}$), 7.18–7.39 (5H, m, Ph—$\underline{H}$).

c) N-(6-Phenylhexyl)[(3S, 4R)-4-benzylthio-3-bromo-2-oxoazetidin-1-yl]acetamide

A solution of (3S, 4R)-4-benzylthio-3-bromoazetidin-2-one (0.7 g, 2.6 mmol) in dry THF (25 ml) was treated with N-(6-phenylhexyl)bromoacetamide (0.8 g, 2.6 mmol), powdered potassium hydroxide (0.2 g 3 mmol) and tetrabutylammonium hydroxide (0.1 g, 0.3 mmol). The mixture was stirred at room temperature for 4 h and partitioned between ether and brine. The organic layer was separated, dried (MgSO$_4$) and evaporated. The residue was purified by flash chromatography using 3:1 ether:pentane as the eluting solvent. Evaporation of the appropriate fractions gave the title compound as an oil (0.63 g, 53%). $^1$H NMR δ (CDCl$_3$) 1.21–1.66 (8H, m, (C$\underline{H}_2$)$_4$), 2.59 (2H, t, J=7.4 Hz, C$\underline{H}_2$), 3.48,3.82 (each 1H, d, J=16 Hz, NC$\underline{H}_2$), 3.21 (2H, h, J=6.00 Hz, C$\underline{H}_2$), 3.37 (1H, dd, J=5.15 Hz, $\underline{H}_{3b}$), 3.83 (2H, s, SC $\underline{H}_2$), 4.59 (1H, d, J=1.6 Hz, $\underline{H}_4$), 4.89 (1H, d, J=1.6 Hz, $\underline{H}_3$), 6.04 (1H, bt, N$\underline{H}$), 7.14–7.36 (10H, m, Ph—$\underline{H}$).

Examples 80 and 81 were prepared from (3S,4R)-N-(6-phenylhexyl)-4-benzylthio-3-bromo-2-oxoazetidin-1-yl acetamide by the method described in Example 2 and 3

EXAMPLE 80

(3S,4R,SR)-N-(6-phenylhexyl)-4-benzylsulphinyl-3-bromo-2-oxoazetidin-1-yl acetamide White crystals m.p. 115–117° C., 17.5% yield Found: C, 57.9; H, 6.0; N, 6.0%; C$_{24}$H$_{29}$N$_2$O$_3$S requires: C, 57.0; H, 5.8; N, 5.5%

EXAMPLE 81

(3S,4R,SS)-N-(6-phenylhexyl)-4-benzylsulphinyl-3-bromo-2-oxoazetidin-1-ylacetamide Colourless solid, mp. 105–107° C., 15% yield Found: C, 57.5H, 6.0; N, 5.5%, C$_{24}$H$_{29}$N$_2$O$_3$S requires: C, 57.0; H, 5.8, N, 5.5%

EXAMPLE 82

(4R,SS/4R,SR)-N-(6-phenylhexyl)-4-benzylsulphinyl-2-oxoazetidin-1-yl acetamide

Treatment of (3S,4R,SS)-N-(6-phenylhexyl)-4-benzylsulphinyl-3-bromo-2-oxoazetidin-1-ylacetamide in either of the procedures below gave (4R,SS/4R,SR)-N-(6-phenylhexyl)-4-benzylsulphinyl-2-oxoazetidin-1-yl acetamide as a mixture whose NMR spectra were identical to a mixture of Examples 30 and 31.

a. To a stirring suspension of activated zinc powder (51.7 mg, 0.79 mmol) in dichloromethane (1.2 ml) and acetic acid (0.4 ml) at 5–10° C. was added N-(6-phenylhexyl)[(4R)-4-benzylsulphinyl-3-bromo-2-oxoazetidin-1-yl]acetamide (0.2 g, 0.4 mmol). After 1 hr, the mixture was diluted with dichloromethane-water, and the organic layer washed with saturated aq. NaHCO$_3$, dried (MgSO$_4$) and evaporated to an oil. Crystallisation from ethyl acetate gave the product as a mixture of diastereoisomers 4R,SS:4R,SR in the ratio 6:1, yield 48 mg (28%), m.p. 120–1° C. The filtrate was evaporated and the residue treated with ether to give a second crop as a 3:1 mixture of diastereoisomers, yield 50 mg (30%), m.p. 108–11° C.

b. A suspension of N-(6-phenylhexyl)[(4R)-4-benzylsulphinyl-3-bromo-2-oxoazetidin-1-yl]acetamide (0.3 g, 0.59 mmol) and 10% palladium on charcoal (50 mg) in ethanol was treated with a solution of sodium hydrogen carbonate (50 mg, 0.59 mmol) in a small amount of water and hydrogenated at 50 psi for 2 hr. The catalyst was filtered off through hyflo and the filtrate evaporated to an oil, which was treated with water and extracted three times with dichloromethane. The combined extracts were dried (MgSO$_4$) and evaporated to an oil which crystallised from either to give the product as a mixture of diastereoisomers 4R,SS:4R,SR in the ratio 3:1, yield 0.17 g (68%), m.p. 110–13° C.

EXAMPLE 83

(3S,4R)-N-(6-phenylhexyl)-1-(4-benzylthio-3-bromo-2-oxoazetidin-1-yl)acetamide a) ((3S, 4R)-4-Benzylthio-3-bromo-2-oxoazetidin-1-yl) acetic acid To a solution of p-methoxybenzyl [(3S, 4R)-4-benzylthio-3-bromo-2-oxoazetidin-1-yl]acetate (3.03 g, 0.0067 mol) in methanol (50 ml) at −5 to −10° C. a 1M solution of potassium hydroxide (7.4 ml) was added dropwise with stirring. After 2 h, the methanol was evaporated off and the residue diluted with water, extracted twice with ether, and the aq. layer acidified with ice cooling to pH 3 (2M HCl). The oil which precipitated soon crystallised and was filtered, washed and dried to give the title compound, yield 0.9 g (41%), m.p. 138–40° C.

b) (3S,4R)-N-(6-phenylhexyl)-1-(4-benzylthio-3-bromo-2-oxoazetidin-1-yl)-acetamide Treatment of the above acetic acid with 6-phenylhexylamine as described in Example 29 gave the title compound, with identical spectra to Example 79.

EXAMPLE 84

(4R,SS)-N-(6-(4-chlorophenyl)hexyl)-(4-benzylsulphinyl-2-oxoazetidin-1-yl)acetamide see examples 154 to 157

EXAMPLE 85

N-[6-(4-Fluorophenyl)hexyl]-4-(4-methoxybenzylthio)-2-oxoazetidin-1-ylacetamide a. N-[6-(4-Fluorophenyl)hexyl]-1-bromoacetamide A cooled solution of 6-(4-fluorophenyl)hexylamine (2.0 g) and Hunig's base (1.33 g) in dry dichloromethane (25 ml) was treated with bromoacetylbromide (2.07 g) in dichloromethane (10 ml) at 0–5° C. After workup and chromatography N-[6-(4-Fluorophenyl)hexyl]-1-bromoacetamide was obtained as a colourless solid, 2.71 g, m.p.50–51° C.

b.   N-[6-(4-Fluorophenyl)hexyl]-4-(4-methoxybenzylthio)-2-oxoazetidin-1-ylacetamide 4-(4-Methoxybenzylthio)-2-oxoazetidinone (2.65 g) was treated with the above bromoacetamide (4 g) in dry THF in the presence of potassium hydroxide (0.7 g) and tetra-n-butylammonium bromide (0.4 g) to give N-[6-(4-fluorophenyl)hexyl]-4-(4-methoxybenzylthio)-2-oxoazetidin-1-ylacetamide (3.8 g, 65% yield) as colourless crystals, m.p. 53–5° C., after chromatography. $^1$H NMR δ (CDCl$_3$) 1.33 (4H, m), 1.58 (4H, m), 2.56 (2H, t), 2.94 (1H, dd), 3.24 (2H, m), 3.37 (1H, dd), 3.61 (1H, d), 3.75 (1H, d), 3.77 (2H, s), 3.79 (3H, s), 4.79 (1H, dd), 6.09 (1H, m), 6.82–7.26 (8H, m).

EXAMPLE 86

N-(6-(2,4-Difluorophenyl)hexyl)-(4-benzylthio-2-oxoazetidin-1-yl)acetamide

Sequential treatment of (4-benzylthio-2-oxoazetidin-1-yl) acetic acid with 1-cyclohexyl-3-(2-morpholinethyl) carbodiimide metho-p-toluenesulfonate and 6-(2,4-difluorophenyl)hexylamine in dimethyl formamide by the method described for Example 29 gave the title compound as a colourless solid, m.p. 65–66° C., in 73% yield $^1$H NMR δ (CDCl$_3$) 1.3–1.36 (4H, m, 4×C$\underline{H}_2$), 1.50–1.60 (4H, m, 4×C$\underline{H}_2$), 2.58 (2H, t, J=7.6 Hz, PhC$\underline{H}_2$), 2.93, 2.97 (1H, dd, J=2.4, 15.6 Hz, $\underline{H}_3$), 3.23 (2H, m, NHC$\underline{H}_2$), 3.35, 3.39 (1H, dd, J=5.2, 15.2 Hz, $\underline{H}_3$), 3.57, 3.71 (each 1H, d, J=16.4 Hz, NC$\underline{H}_2$), 3.81 (2H, s, SOC$\underline{H}_2$), 4.80 (1H, m, $\underline{H}_4$), 6.02 (1H, m, H$\underline{H}$), 6.76–7.33 (8H, m, 2Ph—$\underline{H}$); $v_{c=o}$ 1774 cm$^{-1}$ Found: C, 64.5; H, 6.3; N, 6.5%, C$_{24}$H$_{28}$F$_2$N$_2$O$_2$S requires: C, 64.6; H, 6.3; N, 6.3%

The following amides, Examples 87–96 were prepared by one of the methods described in Examples 29, 85 or 86.

EXAMPLE 87

N-[6-(4-Chlorophenyl)hexyl]-4-(4-methoxybenzylthio)-2-oxoazetidin-1-ylacetamide White crystals, m.p.65–6° C., 89% yield; Found: C, 63.1; H, 6.5; N, 6.1%; C$_{25}$H$_{31}$ClN$_2$O$_3$S requires: C, 63.2; H, 6.6; N, 5.9%

EXAMPLE 88

N-(6-(3,4-Difluorophenyl)hexyl)-(4-benzylthio-2-oxoazetidin-1-yl)acetamide

Colourless solid, m.p. 53–54° C., 77% yield; $^1$H NMR δ (CDCl$_3$) 1.3–1.39 (4H, m, 4×C$\underline{H}_2$), 1.44–1.60 (4H, m, 4×C$\underline{H}_2$), 2.55 (2H, t, J=7.6 Hz, PhC$\underline{H}_2$), 2.91, 2.97 (1H, dd, J=2.4, 15.4 Hz, $\underline{H}_3$), 3.23 (2H, m, NHC$\underline{H}_2$), 3.34, 3.40 (1H, dd, J=5.2, 15.4 Hz, $\underline{H}_3$), 3.56, 3.71 (each 1H, d, J=16.8 Hz, NC$\underline{H}_2$), 3.81 (2H, s, SOC$\underline{H}_2$), 4.80 (1H, m, $\underline{H}_4$), 6.09 (1H, m, N$\underline{H}$), 6.82–7.33 (8H, m 2Ph—$\underline{H}$); $v_{c=o}$ 1776 cm$^{-1}$ Found: C, 64.2; H, 6.3; N, 6.2%; C$_{24}$H$_{28}$F$_2$N$_2$O$_2$S requires: C, 64.6H, 6.3; N, 6.3%

EXAMPLE 89

N-(7-phenylhept-1-yl)-4-benzylthio-2-oxoazetidin-1-yl acetamide

White crystalline solid, m.p. 63–65° C., 96% yield; $^1$H NMR δ (CDCl$_3$) 1.25–1.63 (10H, m), 2.59 (2H, t), 2.93 (1H, dd), 3.22 (2H, dt), 3.36 (1H, dd), 3.50, 3.71 (each 1H, d), 3.81 (2H, s), 4.81(1H, dd), 6.05 (1H, br. singlet), 7.13–7.36 (10H, m).

EXAMPLE 90

N-(6-[4-chlorophenyl]hex-1-yl)-(4-methooxycarbonylbenzylthio)-2-oxoazetidin-1-yl acetamide White crystals, m.p. 87–88° C., 88% yield; Found: C, 62.0; H, 6.2; N, 6.0%; C$_{26}$H$_{31}$ClN$_2$O$_4$S requires: C, 62.1; H, 6.2; N, 5.6%

EXAMPLE 91

N-(5-phenylpentyl)-4-benzylthio-2-oxo-azetidinyl-1-yl acetamide

Colourless oil, 70% yield; $^1$H NMR δ (CDCl$_3$)1.38–1.65 (6H, m,(CH$_2$)$_3$), 2.6 (2H, t, J=7.75 Hz), 2.89–2.96(1H, dd, J=2.5,15 Hz $\underline{H}_{3a}$), 3.32 (2H, q, J=6.68 Hz, NHC$\underline{H}_2$) 3.34 (1H, dd, J=5, 15 Hz, $\underline{H}_{3b}$), 3.59,3.70 (each 1H, d, J=17.00 Hz, NC$\underline{H}_2$), 3.8 (2H, s, SC$\underline{H}_2$), 4.80 (1H, m, $\underline{H}_4$), 6.07 (1H, bs, N$\underline{H}$),7.14–7.33 (10H, m, Ph—$\underline{H}$).

EXAMPLE 92

N-(6-(4-Bromophenyl)hexyl)-4-benzylthio-2-oxoazetidin-1-ylacetamide

Colourless solid, m.p. 73–5° C., 91% yield; $^1$H NMR δ (CDCl$_3$) 1.2–1.7 (8H, m, 4×C$\underline{H}_2$), 2.54 (2H, t, J=8 Hz, C$\underline{H}_2$Ar), 2.94 (1H, dd, J=2, 15 Hz, $\underline{H}_3$), 3.23 (2H, m, NC$\underline{H}_2$), 3.37 (1H, dd, J=5, 15 Hz, $\underline{H}_3$), 3.56, 3.71 (each 1H, d, J=17 Hz, NC$\underline{H}_2$), 3.81 (2H, s, SC$\underline{H}_2$), 4.80 (1H, m, $\underline{H}_4$), 6.06 (1H, br s, N$\underline{H}$), 7.0–7.4 (9H, m, Ph—$\underline{H}$+BrPh—$\underline{H}$)

EXAMPLE 93

N-(6-(4-Fluorophenyl)hexyl)-4-benzylthio-2-oxoazetidin-1-ylacetamide

Colourless oil, 97% yield; $^1$H NMR δ (CDCl$_3$) 1.2–1.7 (8H, m, 4×C$\underline{H}_2$), 2.56 (2H, t, J=8 Hz, C$\underline{H}_2$Ar), 2.94 (1H, dd, J=2, 15 Hz, $\underline{H}_3$), 3.23 (2H, m, NC$\underline{H}_2$), 3.37 (1H, dd, J=5, 15 Hz, $\underline{H}_3$), 3.56, 3.72 (each 1H, d, J=17 Hz, NC$\underline{H}_2$), 3.81 (2H, s, SC$\underline{H}_2$), 4.81 (1H, m, $\underline{H}_4$), 6.07 (1H, br s, N$\underline{H}$), 6.9–7.4 (9H, m, Ph—$\underline{H}$+FPh–$\underline{H}$)

EXAMPLE 94

N-[5-(4-chlorophenyl)pentyl]-4-benzylthio-2-oxo-azetidin-1-yl acetamide

Colourless oil, 63.4% yield $^1$H NMR δ (CDCl$_3$) 1.36–1.62 (6H, m, 3×C$\underline{H}_2$), 2.56 (2H, t, J=7.58 Hz, ArC$\underline{H}_2$), 2.94 (1H, dd, 2.44 Hz, 15.38 Hz, H3$_a$), 3.23(2H, m, NHC$\underline{H}_2$), 3.36 (1H, dd, J=5.17 Hz, 15.38 Hz, $\underline{H}_{3b}$), 3.62&3.55 (1H each, J=16.8 Hz, NC$\underline{H}_2$), 3.80 (2H, , SC$\underline{H}_2$Ph), 4.78 (1H, dd, J=2.46 Hz, 5.16 Hz, H$_4$), 6.05 (1H, m, N$\underline{H}$C=O), 7.06–7.33 (9H, m, 9×Ar$\underline{H}$)

EXAMPLE 95

N-[6-(2-Chlorophenyl)hexyl]-4-benzylthio-2-oxo-azetidin-1yl acetamide

Colourless oil, 84% yield, $^1$H NMR δ (CDCl$_3$) 1.34–1.67 (8H, m, 4×C$\underline{H}_2$), 2.71 (2H, t, J=7.7 Hz, ArCH$_2$), 2.94 (1H, dd, 2.5 Hz, 15.4 Hz, H$_{3a}$), 3.21 (2H, m, NHC$\underline{H}_2$), 3.37 (1H, dd, J=5.2 Hz, 15.4 Hz, $\underline{H}_{3b}$), 3.55, 3.72 (1H each, J=16.75 Hz, NC $_2$), 3.81 (2H, s, SC$\underline{H}_2$Ph), 4.82 (1H, dd, J=2.5 Hz, 5.2 Hz, H$_4$), 6.09 (1H, m, N$\underline{H}$C=O), 7.10–7.33 (9H, m, 9×Ar$\underline{H}$)

EXAMPLE 96

N-(6-[4-chlorophenyl]hex-1-yl)-(4-allyloxycarbonylbenzylthio)-2-oxoazetidin-1-yl-acetamide Pale orange oil, 36% yield 1H NMR δ (CDCl$_3$) 1.25–1.59 (10H, m), 2.55 (2H, m), 2.94 (1H, dd), 3.38 (1H, dd), 3.53 and 3.83 (1H each, d), 3.96 (2H, s), 4.83 (2H, m), 5.27–5.45

(2H, m), 5.92–5.09 (2H, m) 7.07 (1H, d), 7.22 (1H, d), 7.39 (1H, d), 8.02 (1H, d).

EXAMPLE 97

N-[6-(4-methylphenyl)-hexyl]-[4-benzylsulphinyl-2-oxo-azetidin-1-yl]-acetamide

Colourless solid, m.p. ⊖–4° C., 79% yield $^1$H NMR δ (CDCl$_3$) 1.30–1.60 (8H, m, 4×C$\underline{H}_2$), 2.31 (3H, s, ArC$\underline{H}_3$), 2.55 (2H, t, J=7.61 Hz, ArC$\underline{H}_2$), 2.94(1H, dd, J=2.5, 15.4 Hz, $\underline{H}_{3a}$), 3.23 (2H, m, J=13.75 Hz, NHC$\underline{H}_2$), 3.38(1H, dd, J=5.17, 15.37 Hz, $\underline{H}_{3b}$), 3.63 (2H, dd, J=16.75 Hz, COC$\underline{H}_2$N). 3.81 (2H, s, ArC$\underline{H}_2$S), 4.80 (1H, m, J=5.14, 2.47 Hz, $\underline{H}_4$), 6.00 (1H, m, N$\underline{H}$), 7.03–7.36 (9H, m, 9×Ar$\underline{H}$)

Examples 98 and 99 were prepared by the general procedure of Example 86 substituting the phenylhexanols for the amine.

EXAMPLE 98

6-Phenylhexyl (4-benzylthio-2-oxo-azetidin-1-yl) acetate

Colourless oil, 33% yield, $^1$H NMR δ (CDCl$_3$) 1.35–1.60 (8H, m, 4×C$\underline{H}_2$), 2.61 (2H, t, J=7.64 Hz, ArCH2), 3.01 (1H, dd, 2.12 Hz, 5.37 Hz, H$_{3a}$) 3.39 (1H, dd, J=5.1 Hz, 15.26 Hz, $\underline{H}_{3b}$), 3.25, 4.00 (1H each, J=18.09 Hz, NC$\underline{H}_2$), 3.77 (2H, s, SC$\underline{H}_2$Ph), 4.05 (2H, m, OC$\underline{H}_2$), 4.93 (1H, dd, J=2.37 Hz, 5.07 Hz, $\underline{H}_4$), 7.15–7.31 (10H, m, 10×Ar$\underline{H}$)

EXAMPLE 99

6-(4-Chlorophenyl)hexyl-[4-benzylthio-2-oxo-azetidin-1yl]acetate

Colourless oil, 27% yield, $^1$H NMR δ (CDCl$_3$) 1.31–1.68 (8H, m, 4×C$\underline{H}_2$), 2.57 (2h, t, J=7.61 Hz, ArC$\underline{H}_2$), 2.97 (1H, dd, 2.17 Hz, 15.17 Hz, H3a, 3.40 (1H, dd, J=5.1 Hz, 15.25 Hz, $\underline{H}_{3b}$), 3.25, 4.00 (1H each, J=18.10 Hz, NC$\underline{H}_2$), 3.77 (2H, s, SC$\underline{H}_2$Ph), 4.10 (2H, m, OC$\underline{H}_2$), 4.93 (1H, dd, J=2.37 Hz, 5.10 Hz, $\underline{H}_4$), 7.10–7.35 (9H, m, 9×Ar$\underline{H}$)

EXAMPLE 100

1-(9-Phenylnonyl)-4-benzylthio-2-oxoazetidine

Treatment of 4-benzylthio-2-oxo-azetidine (1.35 g) in THF with NaH (0.18 g) followed by 9-phenylnonyltriflate (2.8 g) gave the title compound as a colourless oil, 1.9 g, 68% yield. $^1$H NMR δ (CDCl$_3$) 1.2–1.7 (14H, m, 7×C$\underline{H}_2$), 2.60 (2H, t, J=8 Hz, C$\underline{H}_2$Ar), 2.8, 3.2 (each 2H, m, $\underline{H}_3$+NC$\underline{H}_2$), 3.76 (2H, s, SC$\underline{H}_2$), 4.59 (1H, m, $\underline{H}_4$), 7.15–7.35 (10H, m, Ph—$\underline{H}$)

The following sulfoxides (Examples 101–130) were prepared by treatment of the corresponding sulfides with mCPBA as described for Examples 2 and 3. When described as Diastereoisomer 1 the compounds are predominantly 4R,SR/4S,SS, whereas Diastereoisomer 2 is predominantly 4R,SS/4S,SR.

EXAMPLE 101

N-[6-(4-Fluorophenyl)hexyl]-4-(4-methoxybenzylsulphinyl)-2-oxoazetidin-1-ylacetamide (Diastereoisomer 1)

Colourless crystals, m.p. 147–9° C., 19% yield Found: C, 63.2; H, 6.5; N, 6.0%, C$_{25}$H$_{31}$FN$_2$O$_4$S requires: C, 63.3; H, 6.6; N, 5.9%

EXAMPLE 102

N-[6-(4-Fluorophenyl)hexyl]-4-(4-methoxybenzylsulphinyl)-2-oxoazetidin-1-ylacetamide (Diastereoisomer 2)

Colourless crystals, m.p. 97–9° C., 48% yield Found: C, 63.1; H, 6.4; N, 5.8%; C$_{25}$H$_{31}$FN$_2$O$_4$S requires: C, 63.3; H, 6.6; N, 5.9%

EXAMPLE 103

N-(6-(2,4-Difluorophenyl)hexyl)-(4-benzylsulphinyl-2-oxoazetidin-1-yl)acetamide (Diastereoisomer 1)

Colourless solid, m.p. 153° C., 19% yield; $^1$H NMR δ (CDCl$_3$) 1.3–1.36 (4H, m, 4×C$\underline{H}_2$), 1.50–1.60 (4H, m, 4×C$\underline{H}_2$), 2.57 (2H, t, J=7.6 Hz, PhC$\underline{H}_2$), 2.94, 2.98 (1H, dd, J=4.8, 14.8 Hz, $\underline{H}_3$), 3.23 (2H, m, NHC$\underline{H}_2$), 3.44, 3.48 (1H, dd, J=2.0, 14.8 Hz, $\underline{H}_3$), 3.70, 4.12 (each 1H, d, J=17.2 Hz, NC$\underline{H}_2$), 3.89, 4.05 (each 1H, d, J=13.2 Hz, SOC$\underline{H}_2$), 4.51 (1H, m, $\underline{H}_4$), 6.64 (1H, m, N$\underline{H}$), 6.72–7.41 (8H, m, 2Ph—$\underline{H}$); $v_{c=o}$ 1791 cm$^{-1}$ Found: C, 62.3; H, 6.1; N, 6.1%; C$_{24}$H$_{28}$F$_2$N$_2$O$_3$S requires: C, 62.3; H, 6.1; N, 6.1%

EXAMPLE 104

N-(6-(2,4-Difluorophenyl)hexyl)-(4-benzylsulphinyl-2-oxoazetidin-1-yl)acetamide

Colourless solid, m.p. 114–116° C., 46% yield $^1$H NMR δ (CDCl$_3$) 1.3–1.36 (4H, m, 4×C$\underline{H}_2$), 1.50–1.60 (4H, m, 4×C$\underline{H}_2$), 2.58 (2H, t, J=7.6 Hz, PhC$\underline{H}_2$), 2.87, 2.90 (1H, dd, J=2.4, 15.2 Hz, $\underline{H}_3$), 3.16, 3.19 (1H, dd, J=5.6, 15.2 Hz, $\underline{H}_3$), 3.27 (2H, m, NHC$\underline{H}_2$), 3.88, 4.25 (each 1H, d, J=17.2 Hz, NC$\underline{H}_2$), 3.99, 4.20 (each 1H, d, J=13.2 Hz, SOC$\underline{H}_2$), 4.60 (1H$_4$), 6.72–7.41 (9H, m, 2Ph—$\underline{H}$, N$\underline{H}$) $v_{c=o}$ 1793 cm$^{-1}$ Found: C, 62.3; H, 6.1; N, 6.2%; C$_{24}$H$_{28}$F$_2$N$_2$O$_3$S requires: C, 62.3; H, 6.1; N, 6.1%

EXAMPLE 105

N-[6-(4-Chlorophenyl)hexyl]-4-(4-methoxybenzylsulphinyl)-2-oxoazetidin-1-ylacetamide (Diastereoisomer 1)

Colourless crystals, m.p. 147–9° C., 32% yield Found: C, 61.0; H, 6.2; N, 6.0%; C$_{25}$H$_{31}$ClN$_2$O$_4$S requires: C, 61.2; H, 6.4; N, 5.7%

EXAMPLE 106

N-[6-(4-Chlorophenyl)hexyl]-4-(4-methoxybenzylsulphinyl)-2-oxoazetidin-1-ylacetamide (Diastereoisomer 2)

Colourless crystals, m.p. 102–3° C., 31% yield Found: C, 60.6; H, 6.2, N, 5.8%; C$_{25}$H$_{31}$ClN$_2$O$_4$S.0.3H$_2$O requires: C, 60.5H, 6.4; N, 5.6%

EXAMPLE 107

N-(6-(3,4-Difluorophenyl)hexyl)-(4-benzylsulphinyl-2-oxoazetidin-1-yl)acetamide (Diastereoisomer 1)

Colourless solid, m.p. 171° C., 20% yield $^1$H NMR δ (CDCl$_3$) 1.3–1.36 (4H, m, 4×C$\underline{H}_2$), 1.50–1.60 (4H, m, 4×C$\underline{H}_2$), 2.54 (2H, t, J=7.6 Hz, PhC$\underline{H}_2$), 2.93, 2.99 (1h, dd, J=4.7, 14.9 Hz, $\underline{H}_3$), 3.22 (2H, m, NHC$\underline{H}_2$), 3.43, 3.48 (1H, dd, J=2.2, 14.9 Hz, H$_3$), 3.70, 4.12 (each 1H, d, J=17.4 Hz, NCH$_2$), 3.89, 4.05 (each 1H, d, J=13.1 Hz, SOCH$_2$), 4.51 (1H, m, H$_4$), 6.72 (1H, m, NH), 6.87–7.41 (8H, m, 2Ph—H); $\nu_{c=o}$ 1791 cm$^{-1}$ Found: C, 62.3; H, 6.1; N, 6.2%; C$_{24}$H$_{28}$F$_2$N$_2$O$_3$S requires: C, 62.3; H, 6.1; N, 6.1%

EXAMPLE 108

N-(6-{3,4-Difluorophenyl}hexyl)-(4-benzylsulphinyl-2-oxoazetidin-1-yl)acetamide (Diastereoisomer 2)

Colourless solid, m.p. 115–116° C., 58% yield $^1$H NMR δ (CDCl$_3$) 1.3–1.36 (4H, m, 2×CH$_2$), 1.50–1.60 (4H, m, 2×CH$_2$), 2.54 (2H, t, J=7.6 Hz, PhCH$_2$), 2.87, 2.92 (1H, dd, J=2.5, 15.3 Hz, H$_3$), 3.16, 3.19 (1H, dd, J=5.4, 15.3 Hz, H$_3$), 3.27 (2H, m, NHCH$_2$), 3.88, 4.25 (each 1H, d, J=17.2 Hz, NCH$_2$), 3.98, 4.21 (each 1H, d, J=13.0 Hz, SOCH$_2$), 4.60 (1H, m, H$_4$), 6.85–7.41 (9H, m, 2Ph—H, NH) $\nu_{c=o}$ 1793 cm$^{-1}$ Found: C, 62.4; H, 6.1; N, 6.1%; C$_{24}$H$_{28}$F$_2$N$_2$O$_3$S requires: C, 62.3; H, 6.1; N, 6.1%

EXAMPLE 109

N-(7-phenylhept-1-yl)-4-benzylsulphinyl-2-oxoazetidin-1-yl acetamide (Diastereoisomer 1)

Colourless crystalline solid, m.p. 143–144° C., 27% yield Found: C, 67.7; H, 7.1; N, 6.3%; C$_{25}$H$_{32}$N$_2$O$_3$S 0.1H$_2$O requires: C, 67.9; H, 7.3; N, 6.3%

EXAMPLE 110

N-(7-phenylhept-1-yl)-4-benzylsulphinyl-2-oxoazetidin-1-yl acetamide (Diastereoisomer 2)

Colourless crystalline solid, m.p. 133–34° C., 40% yield Found: C, 67.8; H, 7.1; N, 6.3%; C$_{25}$H$_{32}$N$_2$O$_3$S requires: C, 68.2; H, 7.3; N, 6.4%

EXAMPLE 111

N-(6-[4-chlorophenyl]hex-1-yl)-4-methoxycarbonylbenzylsulphinyl)-2-oxoazetidin-1-yl acetamide (Diastereoisomer 1)

Form white crystals, m.p. 188–9° C., 17% yield Found: C, 60.1; H, 6.0; N, 5.5%; C$_{26}$H$_{31}$ClN$_2$O$_5$S requires: C, 60.2; H, 6.0; N, 5.4%

EXAMPLE 112

N-(6-[4-chlorophenyl]hex-1-yl)-(4-methoxycarbonylbenzylsulphinyl)-2-oxoazetidin-1-yl acetamide (Diastereoisomer 2)

Form white crystals, m.p. 140–41° C., 51% yield Found: C, 60.1; H, 6.0; N, 5.4%; C$_{26}$h$_{31}$ClN$_2$O$_5$S requires: C, 60.2; H, 6.0; N, 5.4%

EXAMPLE 113

N-(6-phenylhex-1-yl)-(4-ethoxycarbonylbenzylsulphinyl)-2-oxoazetidin-1-yl acetamide (Diastereoisomer 1)

Colourless crystals, m.p. 177–178° C., 8.4% yield Found: C, 64.3H, 6.7; N, 5.7%; C$_{27}$H$_{34}$N$_2$O$_5$S 0.3 H$_2$O requires: C, 64.3; H, 6.9; N, 5.6%

EXAMPLE 114

N-(6-[4-chlorophenyl]hex-1-yl)-(4-allyloxycarbonyl-benzylsulphinyl)-2-oxoazetidin-1-yl acetamide (Diastereoisomer 2)

White crystalline solid, m.p. 100–112° C., 30% yield Found: C, 61.7; H, 6.1; N, 5.1% C$_{28}$H$_{33}$ClN$_2$O$_5$S requires C, 61.7; H, 6.1; N, 5.1%

EXAMPLE 115

N-(5-phenylpentyl)-4-benzylsulphinyl-2-oxo-azetidinyl-1-yl acetamide

Colourless solid, m.p. 140–142° C., 6.5% yield $\nu_{c=o}$ 1790,1690 cm$^{-1}$ Found: C, 66.6; H, 6.7; N, 6.8%; C$_{23}$H$_{28}$N$_2$O$_3$ requires: C, 67.0; H, 6.8; N, 6.8%

EXAMPLE 116

N-(5-(4-Chlorophenyl)pentyl)-4-benzylsulphinyl-2-oxo-azetidin-1yl acetamide (Diastereoisomer 1)

Form, White crystals, m.p. 146–47° C., 31.5% yield Found: C, 61.94; H, 6.1; N, 6.8%; C$_{23}$H$_{27}$ClN$_2$O$_3$S requires: C, 61.8; H, 6.1; N, 6.3%

EXAMPLE 117

N-(5-(4-Chlorophenyl)pentyl)-4-benzylsulphinyl-2-oxo-azetidin-1yl acetamide (Diastereoisomer 2)

Colourless crystals, m.p. 117–19° C., 53.8% yield Found: C, 61.7; H, 5.9; N, 6.4%, C$_{23}$H$_{27}$ClN$_2$O$_3$S requires: C, 61.8; H, 6.1; N, 6.3%

EXAMPLE 118

N-[5-(2-Chlorophenyl)hexyl]-4-benzylsulphinyl-2-oxo-azetidin-1yl acetamide (Diastereoisomer 1)

Colourless crystals, m.p. 96–8° C., 35.2% yield Found: C, 61.82; H,6.18; N,6.14%; C$_{24}$H$_{29}$ClN$_2$O$_3$S.0.3H$_2$O requires: C,61.81; H,6.40; N,6.01%

EXAMPLE 119

N-[5-(2-Chlorophenyl)hexyl]-4-benzylsulphinyl-2-oxo-azetidin-1yl acetamide

Colourless crystals, m.p.86–8° C., 57% yield Found: C, 62.6; H, 6.2; N, 6.1%, C$_{24}$H$_{29}$ClN$_2$O$_3$S requires: C,62.5; H,6.3; N,6.1%

EXAMPLE 120

N-(6-(4-Bromophenyl)hexyl)-4-benzylsulphinyl-2-oxoazetidin-1-ylacetamide (Diastereoisomer 1)

Colourless solid, m.p. 177–9° C., 30% yield $^1$H NMR δ (CDCl$_3$) 1.2–1.7 (8H, m, 4×CH$_2$), 2.53 (2H, t, J=8 Hz, CH$_2$Ar), 2.95 (1H, dd, J=5, 15 Hz, H$_3$), 3.21 (2H, m, NCH$_2$), 3.44 (1H, dd, J=2, 15 Hz, H$_3$), 3.72, 4.10 (each 1H, d, J=17 Hz, NCH$_2$), 3.89, 4.04 (each 1H, d, J=13 Hz, SOCH$_2$), 4.54 (1H, m, H$_4$), 6.74 (1H, br s, NH), 7.0–7.4 (9H, m, Ph—H+BrPh—H); $\nu_{c=o}$ 1792 cm$^{-1}$ Found: C, 56.9; H, 5.7; N, 5.6%; C$_{24}$H$_{29}$BrN$_2$O$_3$S requires: C, 57.0; H, 5.8, N, 5.5%

EXAMPLE 121

N-(6-(4-Bromophenyl)hexyl)-4-benzylsulphinyl-2-oxoazetidin-1-ylacetamide (Diastereoisomer 2)

Colourless solid, m.p. 111–3° C., 45% yield $^1$H NMR δ (CDCl$_3$), 1.2–1.7 (8H, m, 4×CH$_2$), 2.54 (2H, t, J=8 Hz, CH$_2$Ar), 2.88 (1H, dd, J=2, 15 Hz, H$_3$), 3.18 (1H, dd, J=5, 15 Hz, H$_3$), 3.25 (2H, m, NCH$_2$), 3.89, 4.24(each 1H, d, J=17 Hz, NCH$_2$), 3.98, 4.19 (each 1H, d, J=13 Hz, SOCH$_2$), 4.62 (1H, m, H$_4$), 7.0–7.4 (10H, m, Ph—H+BrPh—H+NH); $\nu_{c=o}$ 1793 cm$^{-1}$ Found: C, 57.0; H, 5.7; N, 5.6%; C$_{24}$H$_{29}$BrN$_2$O$_3$S requires: C, 57.0; H, 5.8; N, 5.5%

EXAMPLE 122

N-(6-(4-Fluorophenyl)hexyl)-4-benzylsulphinyl-2-oxoazetidin-1-ylacetamide (Diastereoisomer 1)

Colourless solid, m.p. 163–4° C., 33% yield $^1$H NMR δ (CDCl$_3$) 1.2–1.7 (8H, m, 4×C$\underline{H}_2$), 2.55 (2H, t, J=8 Hz, C$\underline{H}_2$Ar), 2.96 (1H, dd, J=5, 15 Hz, $\underline{H}_3$), 3.22 (2H, m, NC$\underline{H}_2$), 3.46 (1H, dd, J=2, 15 Hz, $\underline{H}_3$), 3.71, 4.12 (each 1H, d, J=17 Hz, NC$\underline{H}_2$), 3.89, 4.06 (each 1H, d, J=13 Hz, SOC$\underline{H}_2$), 4.53 (1H, m, $\underline{H}_4$), 6.70 (1H, br s, N$\underline{H}$), 6.9, 7.1 (4H, 2×m, FPh—$\underline{H}$), 7.25, 7.35 (5H, 2×m, Ph—$\underline{H}$); ν$_{c=o}$ 1791 cm$^{-1}$ Found: C, 64.8; H, 6.5; N, 6.2%; C$_{24}$H$_{29}$FN$_2$O$_3$S requires: C, 64.8; H, 6.6; N, 6.3%

EXAMPLE 123

N-(6-(4-Fluorophenyl)hexyl)-4-benzylsulphinyl-2-oxoazetidin-1-ylacetamide (Diastereoisomer 2)

Colourless solid, m.p. 118–9° C., 35% yield $^1$H NMR δ (CDCl$_3$) 1.2–1.7 (8H, m, 4×C$\underline{H}_2$), 2.56 (2H, t, J=8 Hz, C$\underline{H}_2$Ar), 2.89 (1H, dd, J=2, 15 Hz, $\underline{H}_3$), 3.18 (1H, dd, J=5, 15 Hz, $\underline{H}_3$), 3.25 (2H, m, NC$\underline{H}_2$), 3.89, 4.24 (each 1h, d, J=17 Hz, NC$\underline{H}_2$), 3.99, 4.19 (each 1H, d, J=13 Hz, SOC$\underline{H}_2$), 4.60 (1H, m, $\underline{H}_4$), 6.93, 7.10 (4H, 2×m, FPh—$\underline{H}$), 7.2–7.5 (6H, m, Ph—$\underline{H}$+N$\underline{H}$); ν$_{c=o}$ 1793 cm$^{-1}$ Found: C, 64.8; H, 6.5; N, 6.2% C$_{24}$H$_{29}$FN$_2$O$_3$S requires: C, 64.8; H, 6.6; N, 6.3%

EXAMPLE 124

6-Phenylhexyl (4-benzylsulphinyl-2-oxo-azetidin-1-yl)acetate (2:1 Diast 2: Diast 1)

Colourless crystals, m.p. 64–7° C., 80% yield Found: C, 66.5; H,6.8; N,3.3%; C$_{24}$H$_{29}$NO$_4$S.0.8CH$_2$Cl$_2$ requires: C,66.6; H, 6.9; N, 3.1%

EXAMPLE 125

6-(4-Chlorophenyl)hexyl-(4-benzylsulphinyl-2-oxo-azetidin-1yl] acetate

Colourless oil, 25% yield Found: C, 61.3; H, 6.1; N, 3.1%; C$_{24}$H$_{28}$ClNO$_4$S 0.14CH$_2$Cl$_2$ requires: C, 61.2; H, 6.0; N, 3.0%

EXAMPLE 126

1-(9-Phenylnonyl)-4-benzylsulphinyl-2-oxoazetidine (Diastereoisomer 1)

Colourless solid, m.p. 87–8° C., 10% yield $^1$H NMR δ (CDCl$_3$) 1.2–1.7 (14H, m, 7×C$\underline{H}_2$), 2.59 (2H, t, J=8 Hz, C$\underline{H}_2$Ar), 2.85, (1H, dd, J=5, 15 Hz, $\underline{H}_3$), 3.25 (2H, m, NC$\underline{H}_2$), 3.40 (1H, dd, J=2, 15 Hz, $\underline{H}_3$), 3.86, 4.01 (each 1H, d, J=13 Hz, SOC$\underline{H}_2$), 4.33 (1H, m, $\underline{H}_4$), 7.15–7.45 (10H, m, Ph—$\underline{H}$) ν$_{c=o}$ 1777 cm$^{-1}$

EXAMPLE 127

1-(9-Phenylnonyl)-4-benzylsulphinyl-2-oxoazetidine (75% Diastereoisomer 2)

Colourless solid, m.p. 59–61° C., 34% yield $^1$H NMR δ (CDCl$_3$) Dia 2) 1.2–1.7 (14H, m, 7×C$\underline{H}_2$), 2.46 (1H, dd, J=2, 15 Hz, $\underline{H}_3$), 2.59 (2H, t, J=8 Hz, C$\underline{H}_2$Ar), 2.96, (1H, dd, J=5, 15 Hz, $\underline{H}_3$), 3.37 (2H, m, NC$\underline{H}_2$), 3.98, 4.07 (each 1H, d, J=13 Hz, SOC$\underline{H}_2$), 4.37 (1H, m, $\underline{H}_4$), 7.15–7.40 (10H, m, Ph—$\underline{H}$)

EXAMPLE 128

N-[6-(4-Methylphenyl)-hexyl]-[4-benzylsulphinyl-2-oxo-azetidin-1-yl]-acetamide

Colourless solid, m.p. 156–7° C., 29% yield Found: C, 67.9; H, 7.1; N, 6.3%; C$_{25}$H$_{32}$N$_2$O$_3$S requires: C, 68.2; H, 7.3; N, 6.4%

EXAMPLE 129

N-[6-(4-Methylphenyl)-hexyl]-[4-benzylsulphinyl-2-oxo-azetidin-1-yl]-acetamide

Colourless solid, m.p. 94–5° C., 59% yield Found: C, 68.0; H, 7.2; N, 6.3%; C$_{25}$H$_{32}$N$_2$O$_3$S requires: C, 68.2; H, 7.3; N, 6.4%

EXAMPLE 130

N-(6(4-chlorophenyl)hex-1-yl)-((4-carboxybenzylsulphinyl)-2-oxoazetidin-1-yl) acetamide (diastereoisomer 2)

A solution of N-(6-[4-chlorophenyl]hex-1-yl-(4-allyloxycarbonylbenzylsulphinyl)-2-oxoazetidin-1-yl acetamide (diastereoisomer 2) 1.25 g), tetrakis triphenylphosphine palladium(0) (80 mg), triphenylphosphine (635 mg) and pyrrolidine (171 mg) in dichloromethane (100 ml) was stirred at 25° C. for 16 h. The reaction mixture was then chromatographed (fine silica, dichloromethane-50% acetone in dichloromethane), without concentration, to give N-(6-(4-chlorophenyl)hex-1-yl)-((4-carboxybenzylsulphinyl)-2-oxoazetidin-1-yl)acetamide (diastereoisomer 2) as a white solid, m.p. 195–197° C., 62% yield Found: C, 59.0; H, 5.7; N, 5.5%; C$_{25}$H$_{29}$ClN$_2$O$_3$S 0.1H$_2$O requires: C, 59.2; H, 5.8; N, 5.5%

The following sulfones (Examples 131–144) were prepared by treatment of the corresponding sulfide or sulfoxide with an excess of m-CPBA as described in Example 4.

EXAMPLE 131

N-[6-(4-Fluorophenyl)hexyl]-4-(4-methoxybenzylsulphonyl)-2-oxoazetidin-1-ylacetamide Colourless crystals, m.p. 115–8° C., 37% yield Found: C, 61.0; H, 6.3; N, 5.7%; C$_{25}$H$_{31}$FN$_2$O$_5$S requires: C, 61.2; H, 6.4; N, 5.7%

EXAMPLE 132

N-(6-(2,4-Difluorophenyl)hexyl)-4-benzylsulphonyl-2-oxoazetidin-1-yl)acetamide

Colourless solid, m.p. 130–131° C., 68% yield $^1$H NMR δ (CDCl$_3$) 1.3–1.36 (4H, m, 4×C$\underline{H}_2$), 1.50–1.60 (4H, m, 4×C$\underline{H}_2$), 2.58 (2H, t, J=7.6 Hz, PhC$\underline{H}_2$), 2.97, 3.03 (1H, dd, J=2.6, 15.42 Hz, $\underline{H}_3$), 3.08, 3.14 (1H, dd, J=5.0, 15.4 Hz, $\underline{H}_3$), 3.24 (2H, m, NHC$\underline{H}_2$), 3.84, 3.94 (each 1H, d, J=16.9 Hz, NC$\underline{H}_2$), 4.31, 4.37 (each 1H, d, J=14.3 Hz, SO$_2$C$\underline{H}_2$), 4.81 (1H, m, $\underline{H}_4$), 6.0 (1H, m, N$\underline{H}$), 6.72–7.44 (9H, m, 2Ph—) ν$_{c=o}$ 1797 cm$^{-1}$ Found: C, 60.1; H, 5.9; N, 5.9%; C$_{24}$H$_{28}$F$_2$N$_2$O$_4$S requires: C, 60.2; H, 5.9; N, 5.9%

EXAMPLE 133

N-[6-(4-Chlorophenyl)hexyl]-4-(4-methoxybenzylsulphonyl)-2-oxoazetidin-1-ylacetamide Colourless crystals, m.p. 118–20° C., 94% yield Found: C, 59.0; H, 6.1; N, 5.5%; C$_{25}$H$_{31}$ClN$_2$O$_5$S requires: C, 59.2; H, 6.2; N, 5.5%

EXAMPLE 134

N-(6-(3,4-Difluorophenyl)hexyl)-(4-benzylsulphonyl-2-oxoazetidin-1-yl)acetamide

Colourless solid, m.p. 114–115° C., % yield $^1$H NMR δ (CDCl$_3$) 1.3–1.36 (4H, m, 4×C$\underline{H}_2$), 1.50–1.60 (4H, m, 4×C H$_2$), 2.55 (2H, t, J=7.6 Hz, PhCH$_2$), 2.97, 3.03 (1H, dd, J=2.5, 15.4 Hz, H$_3$), 3.08, 3.14 (1H, dd, J=5.0, 15.4 Hz, H$_3$), 3.24 (2H, m, NHCH$_2$), 3.84, 3.94 (each 1H, d, J=16.9 Hz, NCH$_2$), 4.31, 4.37 (each 1H, d, J=14.2 Hz, SO$_2$CH$_2$), 4.83 (1H, m, H$_4$), 6.04 (1H, m, NH), 6.82–7.44 (9H, m, 2Ph—H) $v_{c=o}$ 1797 cm$^{-1}$ Found: C, 60.1; H, 5.9; N, 5.9%; C$_{24}$H$_{28}$F$_2$N$_2$O$_4$S requires: C, 60.2; H, 5.9; N, 5.9%

EXAMPLE 136

N-(7-phenylhept-1-yl)-4-benzylsulphonyl-2-oxoazetidin-1-yl acetamide

Form white crystalline solid, m.p 114–115° C., 85% yield Found: C, 64.9; H, 6.9; N, 6.1%; C$_{25}$H$_{32}$N$_2$O$_4$S 0.3 H$_2$O requires: C, 65.0; H, 7.1; N, 6.1%

EXAMPLE 137

N-[6-(4-Chlorophenyl)hexyl]-(4-(4-carboxybenzylsulphonyl)-2-oxo-azetidin-1-yl) acetamide Colourless crystals, m.p. 137–4° C., 40% yield. Found: C, 56.9; H, 5.7; N, 5.1%; C$_{26}$H$_{31}$ClN$_2$O$_6$S 0.5H2O requires: C, 56.8; H, 6.0; N, 5.1%

EXAMPLE 138

N-[5-(4-Chlorophenyl)pentyl]-4-benzylsulphonyl-2-oxo-azetidin-1yl acetamide

Colourless crystals, m.p. 109–10° C., 81.7% yield Found: C, 59.6; H, 5.7; N, 6.0%; C$_{23}$H$_{27}$ClN$_2$O$_4$S requires: 59.7; H, 5.89; N, 6.1%

EXAMPLE 139

N-[5-(2-Chlorophenyl)hexyl]-4-benzylsulphonyl-2-oxo-azetidin-1yl acetamide

Colourless crystals, m.p. 81–3° C., 84% yield Found: C, 60.5; H,6.1; N,5.9%; C$_{24}$H$_{29}$ClN$_2$O$_4$S. requires: C,60.5; H,6.1; N,5.9%

EXAMPLE 140

N-(6-(4-Fluorophenyl)hexyl)-4-benzylsulphonyl-2-oxoazetidin-1-ylacetamide

Colourless solid, m.p. 132–3° C., 76% yield $^1$H NMR δ (CDCl$_3$) 1.2–1.6 (8H, m, 4×CH$_2$), 2.57 (2H, t, J=8 Hz, CH$_2$Ar), 3.02 (1H, dd, J=2, 15 Hz, H$_3$), 3.10 (1H, dd, J=5, 15 Hz, H$_3$), 3.25 (2H, m, NCH$_2$), 3.85, 3.94 (each 1H, d, J=17 Hz, NCH$_2$), 4.34 (2H, s, SO$_2$CH$_2$), 4.82 (1H, m, H$_4$), 6.0 (1H, br s, NH), 6.9, 7.15 (4H, 2×m, FPh—H), 7.4 (5H, m, Ph—H); $v_{c=o}$ 1797 cm$^{-1}$ Found: C, 62.5; H, 6.3; N, 6.2%; C$_{24}$H$_{29}$FN$_2$O$_4$S requires: C, 62.6; H, 6.4; N, 6.1%

EXAMPLE 141

6-Phenylhexyl-[4-benzylsulphonyl-2-oxo-azetidin-1-yl]acetate

Colourless oil, 2.3% yield $^1$H NMR δ (CDCl$_3$) 1.32–1.65 (8H, m, 4×CH$_2$), 2.60 (2H, t,J=7.64 Hz, ArCH$_2$), 2.95 (1H, dd, 2.35 Hz, 13.35 Hz, H3a), 3.11 (1H, dd, J=5.12 Hz, 15.39 Hz, H$_{3b}$), 3.72, 4.27 (1H each, J=18.3 Hz, NCH$_2$), 4.34 (2H, s, SCH$_2$Ph), 4.11 (2H, m, OCH$_2$), 4.91 (1H, dd, J=2.36 Hz, 5.08 Hz, H$_4$), 7.15–7.43 (10H, m, 10×ArH)

EXAMPLE 142

6-(4-Chlorophenyl)hexyl-(4-benzylsulphonyl-2-oxo-azetidin-1-yl]acetate

Colourless crystals, m.p. 77–9° C., 50% yield Found: C, 60.3; H, 5.9; N, 3.0%; C$_{24}$H$_{28}$ClNO$_5$S requires: C, 60.3; H, 5.9; N, 2.9%

EXAMPLE 143

1-(9-Phenylnonyl)-4-benzylsulphonyl-2-oxoazetidine

Colourless solid, m.p. 69–70° C., 59% yield $^1$H NMR δ (CDCl$_3$) 1.2–1.7 (14H, m, 7×CH$_2$), 2.59 (2H, t, J=8 Hz, CH$_2$Ph), 2.92 (1H, dd, J=2, 15 Hz, H$_3$) 3.1 (2H, m, H$_3$+NCH$_2$), 3.4 (1H, m, NCH$_2$), 4.28 (2H, s, SCH$_2$), 4.50 (1H, m, H$_4$), 7.1–7.5 (10H, m, Ph—H); $v_{c=o}$ 1782 cm$^{-1}$ Found: C, 70.0; H, 7.6; N, 3.4%; C$_{25}$H$_{33}$NO$_3$S requires: C, 70.2; H, 7.8; N, 3.3%

EXAMPLE 144

N-[6-(4-Methylphenyl)-hexyl]-[4-benzylsulphonyl-2-oxo-azetidin-1-yl]-acetamide

Colourless solid, m.p. 125–6° C., 67% yield Found: C, 65.3; H, 6.8; N, 6.0%; C$_{25}$H$_{32}$N$_2$O$_4$S requires: C, 65.8; H, 7.1; N, 6.1%

EXAMPLE 145

N-(6-Phenylhexanoyl)-(4-benzylthio-2-oxoazetidin-yl)acetamide a. 4-Benzylthio-2-oxoazetidin-1-yl)acetamide
Book No. 50516/061

A solution of (4-benzylthio-2-oxoazetidin-1-yl)acetic acid (1.0 g, 3.98 mmol) in dry tetrahydrofuran (25 ml), stirred at 10° C. under a nitrogen atmosphere, was treated with 1,1'-carbonyldidimidazole (0.71 g, 4.38 mmol) and stirred at room temperature for 2 h. Ammonia gas was bubbled through the reaction for 30 minutes. The reaction was stirred for a further 60 minutes, diluted with ethyl acetate (75 ml), washed with aq.sat NaHCO$_3$ solution, brine, dried (MgSO$_4$) and evaporated under reduced pressure. Purification by column chromatography eluted with 20:1 CH$_2$Cl$_2$:MeOH gave the product as a colourless solid, m.p. 127–128° C. (0.92 g, 92% yield). $^1$nmr δ (CDCl$_3$) 2.93,2.99 1H, dd, J=2.4, 15.4 Hz, H$_3$), 3.36,3.42 (1H, dd, J=6.2, 15.4 Hz, H$_3$), 3.47, 3.79 (each 1H, d, J=17 Hz, NCH$_2$), 3.82 (2H, s, SCH$_2$), 4.85 (1H, m, H$_4$), 5.62 (1H, bs, NH), 6.97 (1H, bs. NH), 7.23–7.38 (5H, m, Ph—H)

b. 6-Phenylhexanoyl chloride

6-Phenylhexanoic acid (2.5 g, 13 mmol) was treated with thionyl chloride (3.0 ml, 41.1 mmol) and stirred under reflux for 3 h. The mixture was evaporated under reduced pressure to remove thionyl chloride and then distilled at 92–95° C./0.1 mbar to give the product as a colourless oil (2.57 g, 94%).

c. N-(6-Phenylhexanoyl)-(4-benzylthio-2-oxoazetidin-yl) acetamide

A solution of (4-benzylthio-2-oxoazetidin-1-yl)acetamide (0.63 g, 2.52 mmol) in dry THF (15 ml) was added to a suspension of sodium hyride (60% in oil, 0.10 g, 2.5 mmol) in dry THF at –10° C. under a nitrogen atmosphere. The reaction was stirred at –10° C. for 10 minutes and was then treated with a solution of 6-phenylhexanoyl chloride (0.58 g, 2.75 mmol) in dry THF (5 ml) dropwise over 2 minutes maintaining the temperature at –10° C. The cooling bath was removed an after stirring for 60 minutes the reaction was treated with sodium hydride (50 mg, 1.25 mmol) and 6-phenylhexanoyl chloride (0.29 g, 1.38 mmol) in dry THF (2 ml). The reaction was stirred for 60 minutes, poured into ice/brine (100 ml), extracted with ethyl acetate (2×50 ml). The organic extracts were combined, washed with aq. sat.

NaHCO$_3$ solution, brine, dried (MgSO$_4$) and evaporated under reduced pressure to an orange oil. Purification by repeated column chromatography eluted with hexane:ethyl acetate (3:1 to 1:1) gave the product as a colourless oil (0.22 g, 21% yield, contains 10% 6-phenylhexanoic acid) $^1$H nmr δ (CDCl$_3$) 1.3–1.7 (6H, m, 3×CH$_2$), 2.44 (2H, t, J=7.4 Hz, NHCOCH$_2$), 2.62 (2H, t, J=7.6 Hz, PhCH$_2$), 2.96, 3.02 (1H, dd, J=2.4, 15.3 Hz, H$_3$), 3.39, 3.45 (1H, dd, J=5.1, 15.3 Hz, H$_3$), 3.61, 4.32 (each 1H, d, J=18.8 Hz, NCH$_2$CO), 3.76 (2H, m, SCH$_2$), 4.9 (1H, m, H$_4$), 7.1–7.3 (10H, m, 2×Ph—H), 8.17 (1H, m, NH)

EXAMPLE 146

N-(6-Phenylhexanoyl)-(4-benzylsulphinyl-2-oxoazetidin-yl)acetamide

Treatment of N-(6-Phenylhexanoyl)-(4-benzylthio-2-oxoazetidin-yl)acetamide with mCPBA as in Example 2 gave the title compound as an 50:50 mixture of diastereoisomers. Colourless solid, m.p. 153–156° C., 37% yield $^1$H nmr δ (CDCl$_3$) 1.36 (4H, m, 2×CH$_2$), 1.64 (8H, m, 4×CH$_2$), 3.39 (4H, m 2×PhCH$_2$), 2.48, 2.52 (1H, dd, J=2.4, 15.2 Hz, H$_3$), 2.60 (4H, m, 2×NCH$_2$), 2.96, 2.99 (1H, dd, J=4.8, 14.8 Hz, H$_3$'), 3.03, 3.07 (1H, dd, J=5.2, 15.2 Hz, H$_3$), 3.39, 3.43 (1H, J=2.0, 14.8 Hz, H$_3$'), 3.9–4.6 (8H, m, 2×NCH$_2$, 2×SOCH$_2$), 4.72 (1H, m, H$_4$'), 4.81 (1H, m, H$_4$), 7.16–7.40 (20H, m, 4×Ph—H), 8.49 (1H, s, NH), 9.01 (1H, s, NH); ν$_{c=o}$ 1787 cm$^{-1}$ Found: C, 65.3; H, 6.4; N, 6.4%; C$_{24}$H$_{28}$N$_2$O$_4$S requires: C, 65.4, H, 6.4; N, 6.4%

EXAMPLE 147

N-(5-Phenylpentyloxy)-(4-benzylthio-2-oxoazetidin-1-yl)acetamide

Treatment of (4-benzylthio-2-oxo)azetidin-1-ylacetic acid with N-(5-phenylpentyl)hydroxylamine by the method described for Examples 1 and 86 gave N-(5-phenylpentyloxy)-(4-benzylthio-2-oxoazetidin-1-yl) acetamide as a colourless oil in 55% yield. $^1$H NMR δ (DMSO 350K) 1.31–1.43 (2H, m, CH$_2$), 1.53–1.67 (4H, m, 2×CH$_2$), 2.58 (2H, t, J=7.6 Hz, PhCH$_2$), 2.85, 2.91 (1H, dd, J=2.4, 15.0 Hz, H$_3$), 3.41 (1H, d, J=18.2 Hz, 1 of NCH$_2$), 3.74–3.91 (5H, m, 1 of NCH$_2$, SCH$_2$, NHOCH$_2$), 4.87 (1H, m, H$_4$), 7.10–7.35 (10H, m, 2×Ph—H), 10.8 (1H, m, NH).

Treatment of N-(5-phenylpentyloxy)-(4-benzylthio-2-oxoazetidin-1-yl)acetamide with m-CPBA gave the following two compounds after work up as described for Examples 2 and 3.

EXAMPLE 148

N-(5-Phenylpentyloxy)-(4-benzylsulphinyl-2-oxoazetidin-1-yl)acatamide (Diastereoisomer 1)

Colourless solid, m.p. 178–179° C., 23% yield $^1$H NMR δ (DMSO 350K) 1.34–1.38 (2H, m, CH$_2$), 1.56–1.62 (4h, M, 2×CH$_2$), 2.58 (2H, t, j=7.6 Hz, PhCH$_2$), 3.0–3.17 (2H, m, H$_3$), 3.65, 3.40 (each 1H, m, SOCH$_2$), 3.75 (2H, t, J=6.5 Hz, NHOCH$_2$), 3.85, 4.10 (each 1H, d, J=18 Hz, NCH$_2$), 4.87 (1H, m, H$_4$), 7.14–7.35 (10H, m, 2×Ph—H), 10.9 (1, m, NH) ν$_{c=o}$ 1777 cm$^{-1}$ Found: C, 63.8; H, 6.5; N, 6.5%; C$_{23}$H$_{28}$N$_2$O$_4$S (+1.0% H$_2$O) requires: C, 63.8; H, 6.6; N, 6.5%

EXAMPLE 149

N-(5-Phenylpentyloxy)-(4-benzylsulphinyl-2-oxoazetidin-1-yl)acatamide (Diastereoisomer 2)

Colourless oil, 39% yield $^1$H NMR δ (DMSO 350K) 1.36 (2H, m, CH$_2$), 1.56–1.61 (4H, m, 2×CH$_2$), 2.58 (2H, t, J=7.6 Hz, PhCH$_2$), 2.9, 3.2 (2H, m, H$_3$), 3.75 (2H,t,J=6.6 Hz, NHOCH$_2$), 3.9, 4.05 (each 1H, m, SOCH$_2$), 4.04, 4.20 (each 1H, d, J=12.9 Hz, NCH$_2$), 4.79 (1H, m, H$_4$), 7.16–7.37 (10H, m, 2×Ph—H), 10.95 (1H,m, NH); ν$_{c=o}$ 1788 cm$^{-1}$ Found: C, 63.7; H, 6.6; N, 6.2%; C$_{23}$H$_{28}$N$_2$O$_4$S(+1.4% C$_4$H$_8$O$_2$, 1.0% H$_2$O) requires C, 63.7; H, 6.7; N, 6.4%

EXAMPLE 150

R—N-(6-(4-Chlorophenyl)hexyl)-(4-benzylthio-2-oxoazetidin-1-yl)acetamide

Treatment of R-(-)-(4-benzythio-2-oxoazetidin-1-yl) acetic acid [prepared from the corresponding racemic acid by recrystallisation of the salt formed with chinchonidine [α]$_D^{25}$=-43° (c=1, CHCl$_3$)] with dicyclohexylcarbidimide and 6-(4-chlorophenyl)hexylamine by the procedure described for Example 29 gave R—N-(6-{4-Chlorophenyl}hexyl)-(4-benzylthio-2-oxoazetidin-1-yl) acetamide as a colourless sold, m.p. 71° C., 83% yield. $^1$H nmr δ (CDCl$_3$) 1.33 (4H, m, 2×CH$_2$), 1.47–1.6 (4H, m, 2×CH$_2$), 2.56 (2H, t, J=7.6 Hz, PhCH$_2$), 2.92, 2.97 (1H, dd, J=2.4, 15.4 Hz, H$_3$), 3.22–3.24 (2H, m, NHCH$_2$), 3.33, 3.39 (1H, dd, J=5.2, 15.4 Hz, H$_3$), 3.54, 3.72 (each 1H, d, J=16.8 Hz, NCH$_2$), 3.81 (1H, s, SCH$_2$), 4.80 (1H, m, H$_4$), 6.11 (1H, m, NH), 7.07–7.33(9H, m, 2×Ph—H) ν$_{c=o}$ 1776 cm$^{-1}$; [α]$_D$=+36.0° (c=1.1% w/v in CHCl$_3$) at 25° C. Found: C, 64.8; H, 6.5; N, 6.4%; C$_{24}$H$_{29}$ClN$_2$O$_2$S requires: C, 64.8; H, 6.6; N, 6.3%

EXAMPLE 151

S—N-(6-{4-Chlorophenyl}hexyl)-(4-benzylthio-2-oxoazetidin-1-yl)acetamide 4S-(4-benzylthio-2-oxoazetidin-1-yl)acetic acid, [α]$_D^{25}$=+34° (c=1.1%, CHCl$_3$) was prepared from the corresponding racemic acid by recrystallisation of the salt formed with cinchonine or brucine. This chirally pure acid was treated with 4-chlorophenyl)hexylamine by the procedure of Example 29 to give the title compound as a colourless solid, m.p. 69–70° C., 73% yield. $^1$H nmr δ (CDCl$_3$) 1.33 (4H, m 2×CH$_2$), 1.47–1.6 (4H, m, 2×CH$_2$), 2.56 (2H, t, J=7.6 Hz, PhCH$_2$), 2.93, 2.97 (1H, dd, J=2.4, 15.2 Hz, H$_3$), 3.22–3.24 (2H, m, NHCH$_2$), 3.35, 3.39 (1H, dd, J=5.2, 15.2 Hz, H$_3$), 3.54, 3.72 (each 1H, d, J=16.8 Hz, NCH$_2$), 3.81 (1H, s, SCH$_2$), 4.80 (1H, m, H$_4$), 6.11 (1H, m, NH), 7.05–7.36 (9H, m, 2×Ph—H); ν$_{c=o}$ 1776 cm$^{-1}$; [α]$_D$=-36.3° (C=0.9% w/v in CHCl$_3$) at 25° C. Found: C, 64.5; H, 6.5; N, 6.3%; C$_{24}$H$_{29}$ClN$_2$O$_2$S requires: C, 64.8; H, 6.6; N, 6.3%

EXAMPLE 152

4R,SR-N-(6-(4-Chlorophenyl)hexyl)-(4-benzylsulphinyl-2-oxoazetidin-1yl-acetamide 4R-N-(6-(4-Chlorophenyl)hexyl)-(4-benzylsulphinyl-2-oxoazetidin-1-yl)acetamide (0.5 g) was treated with (+)-(8, 8-Dichlorocamphorylsulfonyl)oxaziridine (0.3 g) in dichlorometnane (70 ml) at 25° C. for 16 h to give the title compound after chromatography (silica/EtOAc) as a colourless solid, m.p. 159–160° C., (0.21 g, 41% yield). $^1$nmr δ (CDCl$_3$) 1.3–1.6 (8H, m, 4×CH$_2$), 2.55 (2H, t, J=7.6 Hz, PhCH$_2$), 2.93, 2.98 (1H, dd, J=4.8, 14.8 Hz, H$_3$), 3.22 (2H, m, NHCH$_2$), 3.44, 3.48 (1H, dd, J=2.2, 14.8 Hz, H$_3$), 3.68, 4.13 (each 1H, d, J=17.4 Hz, NCH$_2$), 3.88, 4.05 (each 1H, d, J=12.8 Hz, SOCH$_2$), 4.50 (1H, m, H$_4$), 6.65 (1H, m, NH), 7.07–7.40 (9H, m, 2×Ph—H); ν$_{c=o}$ 1791 cm$^{-1}$; [α]$_D$=-166.91° (c=1.08% w/v in CHCl$_3$) at 25° C. Found: C, 62.2; H, 6.3; N, 6.1%; C$_{24}$H$_{29}$ClN$_2$O$_3$ requires: C, 62.5; H, 6.3; N, 6.1%

EXAMPLE 153

4S,SS-N-(6-(4-Chlorophenyl)hexyl)-(4-benzylsulphinyl-2-oxoazetidin-1yl)acetamide 4S-N-(6-(4-Chlorophenyl)hexyl)-(4-benzylsulphinyl-2-oxoazetidin-1-yl)acetamide (1 g) was treated with (−)-(8,8-dichlorocamphorylsulfonyl)oxaziridine (0.67 g) in dichlorometnane (75 ml) at 25° C. for 16 h to give the title compound, after chromatography (silica/EtOAc), as a colourless solid, m.p. 159° C., (0.95 g, 83% yield); $^1$H nmr δ (CDCl$_3$) 1.2–1.6 (8H, m, 4×C$\underline{H}_2$), 2.55 (2H, t, J=7.6 Hz, PhC$\underline{H}_2$), 2.93, 2.99 (1H, dd, J=4.8, 14.8 Hz, $\underline{H}_3$), 3.22 (2H, m, NHC$\underline{H}_2$), 3.44, 3.49 (1H, dd, J=2.2, 14.8 Hz, $\underline{H}_3$), 3.68, 4.13 (each 1H, d, J=17.4 Hz, NC$\underline{H}_2$), 3.88, 4.05 (each 1H, d, J=13.1 Hz, SOC$\underline{H}_2$), 4.50 (1H, m, $\underline{H}_4$), 6.65 (1H, m, N$\underline{H}$), 7.07–7.40 (9H, m, 2×Ph—$\underline{H}$); $v_{c=o}$ 1791 cm$^{-1}$; [α]$_D$=+169.2° (c=1.0% w/v in CHCl$_3$) at 25° C. Found: C, 62.4; H, 6.3; N, 6.1%; C$_{24}$h$_{29}$ClN$_2$O$_3$ requires: C, 62.5; H, 6.3; N, 6.1%

EXAMPLE 154

4R,SS-N-(6-(4-Chlorophenyl)hexyl)-(4-benzylsulphinyl-2-oxoazetidin-1-yl)acetamide (diastereoisomer 2)

Treatment of 4R-N-(6-(4-chlorophenyl)hexyl)-(4-benzylthio-2-oxoazetidin-1-yl)acetamide (0.95 g) with mCPBA (0.355 g/65% pure) in dichloromethane (40 ml) by the procedure of Example 30 gave the title compound as a colourless solid, m.p. 139–140° C., 16% yield after repeated recrystallisation from butanone; $^1$H nmr δ (CDCl$_3$) 1.33 (4H, m, 2×C$\underline{H}_2$), 1.5–1.65 (4H, m, 2×C$\underline{H}_2$), 2.56 (2H, t, J=7.6 Hz, PhC$\underline{H}_2$), 2.87, 2.91 (1H, dd, J=2.4, 15.6 Hz, $\underline{H}_3$), 3.16, 3.20 (1H, dd, J=5.2,15.6 Hz, $\underline{H}_3$), 3.22–3.32 (2H, m, NHC$\underline{H}_2$), 3.87, 4.26 (each 1H, d, J=16.8 Hz, NC$\underline{H}_2$), 3.97, 4.18 (each 1H, d, J=13.2 Hz, SOC$\underline{H}_2$), 4.60 (1H, m, $\underline{H}_4$), 7.08–7.41 (10H, m, 2×Ph—$\underline{H}$, N$\underline{H}$); $v_{c=o}$ 1793 cm$^{-1}$; Found: C, 61.6; H, 6.1; N, 6.1%; C$_{24}$H$_{29}$ClN$_2$O$_3$S .0.26 H$_2$O requires: C, 61.9; H, 6.4; N, 6.0%

EXAMPLE 155

4R,SS-N-(6-(4-Chlorophenyl)hexyl)-(4-benzylsulphinyl-2-oxoazetidin-1yl)acetamide (diastereoisomer 2)

4R-N-(6-(4-chlorophenyl)hexyl)-(4-benzylthio-2-oxoazetidin-1-yl)acetamide (52.2 g) was treated with mCPBA (26.3 g/65% pure) in dichloromethane (1500 ml) at −70 to −74° C. for 120 min. After work-up with aqueous sodium sulfite and sodium bicarbonate the organic layer was dried and evaporated to give an approximately 65:35 mixture of sulfoxide diastereoisomers (2:1) (53.1 g). This was combined with other similar batches of material and separated by preparative HPLC on a Septech 800C instrument using a Merck 50 mm selfpacker column with Lichrosphere 10 um silica (220 g) as stationary phase and 60% ethanol/40% n-hexane as eluant to give the title compound as a colourless solid, m.p. 139–140° C., 35% overall yield. [α]$_D$=+126.4° (c=1.004% w/v in CHCl$_3$) at 25° C.; Found: C, 62.5; H, 6.2; N, 6.2% C$_{24}$H$_{29}$ClN$_2$O$_3$S requires: C, 62.5; H, 6.3; N, 6.1%; spectra same as for Example 154.

EXAMPLE 156

4R,SS-N-(6-(4-Chlorophenyl)hexyl)-(4-benzylsulphinyl-2-oxoazetidin-1-yl)acetamide (diastereoisomer 2)

R-(+)-1,1'-Binaphthol (0.256 g) was suspended in toluene (20 ml) at 25 C and Ti(OiPr)4 (0.134 ml) and water (0.168 ml) added. After 1 h 4R-N-(6-(4-chlorophenyl)hexyl)-(4-benzylthio-2-oxoazetidin-1-yl)acetamide (2.07 g) in toluene (12 ml) was added and the mixture stirred for 30 min. t-Butylhydroperoxide (1.36 ml) was added and the mixture stirred for 66 h. After chromatography a 6:1 mixture of sulfoxide diastereoisomers (4R,SS:4R,SR) was isolated (1.6 g, 75%). The 4R,SR isomer was removed by addition of 0.222 g of 4S,SS-N-(6-(4-chlorophenyl)hexyl)-(4-benzylsulphinyl-2-oxoazetidin-1-yl)acetamide to the mixture, crystallisation of the 4R,SR/4S,SS racemate from the mixture and crystallisation of 4R,SS-N-(6-(4-chlorophenyl)hexyl)-(4-benzylsulphinyl-2-oxoazetidin-1-yl)acetamide (1.19 g, 55%, colourless solid, m.p. 139–140° C.) from the mother liquor. Spectra and physical properties were the same as those of Example 154.

EXAMPLE 157

4R,SS-N-(6-(4-Chlorophenyl)hexyl)-(4-benzylsulphinyl-2-oxoazetidin-1-yl)acetamide (diastereoisomer 2)

a. R-(−) (4-Benzylsulfinyl-2-oxoazetidin-1-yl) acetic acid
9.11 g of R-(−)-(4-Benzylthio-2-oxoazetidin-1-yl)acetic acid was dissolved in 250 ml dry dichloromethane and cooled to −70° C. Ozone gas was then passed through the solution in pulses until all the starting material was consumed. The reaction mixture was then purged with oxygen and allowed to warm to room temperature. Triphenyl phosphine (~) 10 mg was added to the solution which was then evaporated to an oil/solid (10.7 g). The two component mixture was then triturated with chloroform (100 ml) at room temperature causing the oil to dissolve. The solid was filtered off and found to be predominantly diastereoisomer 1 (4R, SR) (4.55 g, 46%) (~90% dia 1), m.p. 142–144° C. The filtrate was the evaporated to dryness to yield a glass which was predominantly (94%) diastereoisomer 2 (4R, SS) by hplc. (4.6 g 47%) m.p. indeterminate. $^1$H nmr δ 2.95 (1H, dd, $H_3$), 3.29 (1H, dd, $H_3$), 3.78–4.24 (4H,m, NCH$_2$, SOCH$_2$), 4.81 (1H, m, $H_4$), 7.36 (5H, m, Ar-H)

b. 4-chlorophenylhexyl amine (1.31 g, 0.0074 mol) in dry dimethylformamide was added to a mixture of 1-hydroxybenzotriazole (0.96 g), N,N'-dicyclohexylcarbodiimide (1.52 g) and the predominantly 4R,SS-(−)-4-(benzylsulphinyl-2-oxoazetidin-1-yl)acetic acid (2 g), prepared in (a) above, in dry dimethylformamide (50 ml) at room temperature and allowed to stir for two hours. After aqueous work-up, evaporation of the organic solvnts and recrystallisation from ethyl acetate the title compound was isolated in a 94:6 mixture with the corresponding 4R,SR isomer (1.66 g, 55%) m.p. 133–134° C.

EXAMPLE 158

4S,SR-N-(6-(4-Chlorophenyl)hexyl)-(4-benzylsulphinyl-2-oxoazetidin-1-yl)acetamide (diastereoisomer 2)

The title compound was prepared from 4S-N-(6-(4-chlorophenyl)hexyl)-(4-benzylthio-2-oxoazetidin-1-yl) acetamide using the procedure described in Example 156 but substituting S-(−)-1,1'-binaphthol for R-(+)-1,1'-binaphthol and 4R,SR-N-(6-(4-chlorophenyl)hexyl)-(4-benzylsulphinyl-2-oxoazetidin-1yl)acetamide for 4S,SS-N-(6-(4-chlorophenyl)hexyl)-(4-benzylsulphinyl-2-oxoazetidin-1-yl)acetamide and was obtained as a colourless solid, m.p. 139–140° C., 44% yield; $^1$H nmr δ (CDCl$_3$) 1.33 (4H, m, 2xCH$_2$), 1.5–1.65 (4H, m 2xCH$_2$), 2.56 (2H, t, J=7.7

Hz, PhCH$_2$), 2.87, 2.91 (1H, dd, J=2.4, 15.3 Hz, H$_3$), 3.16, 3.20 (1H, dd, J=5.1,15.3 Hz, H$_3$), 3.22–3.32 (2H, m, NHCH$_2$), 3.87, 4.26 (each 1H, d, J=17.1 Hz, NCH$_2$), 3.97, 4.18 (each 1H, d, J=13 Hz, SOCH$_2$), 4.60 (1H, m, H$_4$), 7.08–7.41 (10H, m, 2xPh-H, NH); $\nu_{c=o}$ 1793 cm$^{-1}$; [$\alpha$]$_D$=−124.11° (c=1.1% w/v in CHCl$_3$) at 25° C.; Found: C, 62.4; H, 6.3; N, 6.1%; C$_{24}$H$_{29}$ClN$_2$O$_3$S requires: C, 62.5; H, 6.3; N, 6.1%

EXAMPLE 159

4R-N-(6-(4-Chlorophenyl)hexyl)-(4-benzysulphonyl-2-oxoazetidin-1-yl)acetamide

The title compound was isolated by chromatography of the reaction mixture produced in Example 156 and was obtained as a colourless solid, m.p. 145° C., 18% yield; $^1$H nmr (CDCl$_3$) δ 1.3–1.6 (8H, m, 4xCH$_2$), 2.56 (2H, t, J=7.6 Hz, PhCH$_2$), 2.96, 3.02 (1H, dd, J=2.5, 15.4 Hz, H$_3$), 3.09, 3.13 (each 1H, d, J=5.1, 15.4 Hz, H$_3$), 3.24 (2H, m, NHCH$_2$), 3.85, 3.94 (each 1H, d, J=16.9 Hz, NCH$_2$), 4.34 (2H, dd, J=14.2 Hz, SO$_2$CH$_2$), 4.83 (1H, m, H$_4$), 6.1 (1H, m, NH), 7.07–7.43 (9H, m, 2xPh-H); $\nu_{c=o}$ 1797 cm$^{-1}$; [$\alpha$]$_D$=−34.7° (c=1.0% w/v in CHCl$_3$) at 25° C.

Found: C, 60.3; H, 6.0; N, 5.9%; C$_{24}$H$_{29}$ClN$_2$O$_4$S requires: C, 60.4; H, 6.1; N, 5.9%

EXAMPLE 160

4S-N-(6-(4-Chlorophenyl)hexyl)-(4-benzysulphonyl-2-oxoazetidin-1-yl)acetamide

The title compound was produced by treatment of 4S-N-(6-(4-chlorophenyl)hexyl)-(4-benzythio-2-oxoazetidin-1-yl)acetamide with mCPBA as described in Example 4 and was obtained as a colourless solid, m.p. 147° C., 62% yield; $^1$H nmr (CDCl$_3$) δ 1.3–1.6 (8H, m, 4xCH$_2$), 2.56 (2H, t, J=7.6 Hz, PhCH$_2$), 2.96, 3.03 (1H, dd, J=2.5, 15.4 Hz, H$_3$), 3.09, 3.12 (each 1H, d, J=5.1, 15.4 Hz, H$_3$), 3.25 (2H, m, NHCH$_2$), 3.85, 3.94 (each 1H, d, J=16.8 Hz, NCH$_2$), 4.34 (2H, dd, J=14.2 Hz, SO$_2$CH$_2$), 4.83 (1H, m, H$_4$), 6.1 (1H, m, NH), 7.08–7.43 (9H, m, 2xPh-H; $\nu_{c=o}$ 1798 cm$^{-1}$; [$\alpha$]$_D$=+36.3° (c=1.1%w/v in CHCl$_3$) at 25° C.

Found: C, 60.3; H, 6.0; N, 5.9%; C$_{24}$H$_{29}$ClN$_2$O$_4$S requires: C, 60.4; H, 6.1; N, 5.9%

EXAMPLE 161

4R-(6-Phenylhexyl)-(4-benzylthio-2-oxoazetidin-1-yl)acetamide

Treatment of 4R-(4-benzylthio-2-oxo-azetidin-1-yl)acetic acid (Example 84) with dicyclohexylcarbodiimide and 6-phenylhexylamine by the method described in Example 29 to give the title compound as a colourless solid, m.p. 46–47° C., 49% yield; $^1$H nmr δ (CDCl$_3$) 1.33 (4H, m, 2xCH$_2$), 1.5–1.65 (4H, m, 2xCH$_2$), 2.59 (2H, t, J=7.6 Hz, PhCH$_2$), 2.92, 2.96 (1H, dd, J=2.4, 15.2 Hz, H$_3$), 3.22 (2H, m, NHCH$_2$), 3.35, 3.39(1H, dd, J=5.2, 15.2 Hz, H$_3$), 3.56, 3.71 (each 1H, d, J=16.8 Hz, NCH$_2$), 3.81 (2H, s, SCH$_2$), 4.80 (1H, m, H$_4$), 6.0 (1H, m, NH), 7.15–7.4 (10H, m, 2xPh-H); $\nu_{c=o}$ 1776 cm$^{-1}$; [$\alpha$]$_D$=+6.6° (c=1.1%w/v in ethanol) at 25° C.

Found: C, 70.0; H, 7.2; N, 6.9%; C$_{24}$H$_{30}$N$_2$O$_2$S requires: C, 70.2; H, 7.4; N, 6.8%

EXAMPLE 162

4R,SR-N-(6-Phenylhexyl)-(4-benzylsulphinyl-2-oxoazetidin-1-yl)acetamide

A mixture of (S)-(−)-1,1'-Bi-2-naphthol (28 mg, 0.98 mmol) in dry toluene (2 ml) was treated with titanium IV isopropoxide (14 mg, 0.0494 mmol) and water (25 mg, 1.34 mmol). The dark orange mixture was stirred for 60 minutes and treated with a solution of R-N-(6-phenylhexyl)-(4-benzylthio-2-oxoazetidin-1-yl)acetamide (200 mg, 0.487 mmol) in dry toluene (1 ml). The reaction was stirred for 30 minutes and then treated with tert-butylhydroperoxide (70% in water, 0.14 ml, 1.02 mmol) and stirring was continued for 3.5 h. Purification by column chromatography eluted with ethyl acetate to 15:1 ethyl acetate:ethanol and recrystallisation from ethyl acetate gave the product as a pale yellow solid, m.p. 145° C. (0.079 g, 38% yield). $^1$H nmr δ (CDCl$_3$) 1.33 (4H, m, 2xCH$_2$), 1.5–1.65 (4H, m, 2xCH$_2$), 2.59 (2H, t, J=7.8 Hz, PhCH$_2$), 2.93, 2.97 (1H, dd, J=4.8, 14.8 Hz, H$_3$), 3.22 (2H, m, NHCH$_2$), 3.45, 3.48 (1H, dd, J=2.4,14.8 Hz, H$_3$), 3.70, 4.12 (each 1H, d, J=17.2 Hz, NCH$_2$), 3.88, 4.06 (each 1H, d, J=12.8 Hz, SOCH$_2$), 4.50 (1H, m, H$_4$), 6.65 (1H, m, NH), 7.16–7.4 (10H, m, 2xPh-H); $\nu_{c=o}$ 1789 cm$^{-1}$ Found: C, 65.7; H, 6.7; N, 6.3%; C$_{24}$H$_{30}$N$_2$O$_3$S requires: C, 67.6; H, 7.1; N, 6.6%

EXAMPLE 163

N-(6-{4-Fluorophenyl}hexyl)-4-(4-allyloxycarbonylbenzylthio-2-oxoazetidin-1-yl)acetamide Treatment of 4-(4-allyloxycarbonylbenzylthio)azetidin-2-one with N-(6-(-4-fluorophenyl)hexyl)-1-bromoacetamide by the method described in Example 85a gave the title compound as a colourless oil, 43% yield. $^1$H NMR δ (CDCl$_3$) 1.30–160 (8H, m, 4xCH$_2$), 2.55 (2H, t, J=7.6 Hz, CH$_2$Ph), 2.90, 2.97 (1H, dd, J=2.4, 15.4 Hz, H$_3$), 3.23 (2H, m, NHCH$_2$), 3.35, 3.41 (1H, dd, J=5.1, 15.4 Hz, H$_3$), 3.53, 3.78 (each 1H, d, J=16.6 Hz, NCH$_2$), 3.86 (2H, s, SCH$_2$), 4.83 (3H, m, CO$_2$CH$_2$, H$_4$), 5.37 (2H, m, CH$_2$═CH), 6.0 (2H, m, NH, CH$_2$═CH), 6.94 (2H, m, 4-FPh-H), 7.10 (2H, m, 4-FPh-H), 7.39 (2H, d, J=8.3 Hz, 4-CO$_2$allylPh-H), 8.02 (2H, d, J=8.3 Hz, 4-CO$_2$allylPh-H)

Treatment of N-(6-(4-fluorophenyl)hexyl)-4-(4-allyloxycarbonylbenzylthio-2-oxoazetidin-1-yl)acetamide with mCPBA followed by recrystallisation as described for Example 2 and 3 gave the compounds described in Examples 164 and 165.

EXAMPLE 164

N-(6-{4-Fluorophenyl}hexyl)-4-(4-allyloxycarbonylbenzylsulphinyl-2-oxoazetidin-1-yl) acetamide (Diastereoisomer 1)

Colourless solid, m.p. 190–191° C., 24% yield. $^1$H NMR δ (CDCl$_3$) 1.30–1.60 (8H, m, 4xCH$_2$), 2.55 (2H, t, J=7.6 Hz, CH$_2$Ph), 2.95, 2.98 (1H, dd, J=4.8, 14.8 Hz, H$_3$), 3.24 (2H, m, NHCH$_2$), 3.42, 3.46 (1H, dd, J=2.4, 14.8 Hz, H$_3$), 3.76, 4.09 (each 1H, d, J=17.2 Hz, NCH$_2$), 3.95, 4.01 (each 1H, d, J=13.2 Hz, SOCH$_2$), 4.59 (1H, m, H$_4$), 4.84 (2H, m, CO$_2$CH$_2$), 5.37 (2H, m, CH$_2$═CH), 6.0 (1H, m, CH$_2$═CH), 6.47 (1H, m, NH), 6.95 (2H, m, 4-FPh-H), 7.10 (2H, m, 4-FPh-H), 7.36 (2H, d, J=8 Hz, 4-CO$_2$allylPh-H), 8.09 (2H, d, J=8 Hz, 4-CO$_2$allylPh-H). Found: C, 63.3; H, 6.2; N, 5.4%. C$_{28}$H$_{33}$FN$_2$O$_5$S requires: C, 63.6; H, 6.3; N, 5.3%

EXAMPLE 165

N-(6-{4-Fluorophenyl}hexyl)-4-(4-allyloxycarbonylbenzylsulphinyl-2-oxoazetidin-1-yl) acetamide (Diastereoisomer 2)

Colourless solid, m.p. 115–117° C., 53% yield. $^1$H NMR δ (CDCl$_3$) 1.30–1.60 (8H, m, 4xCH$_2$), 2.56 (2H, t, J=7.6 Hz, CH$_2$Ph), 2.91, 2.95 (1H, dd, J=2.4, 15.2 Hz, H$_3$), 3.27 (3H, m, NHCH$_2$, H$_3$), 3.94, 4.22 (each 1H, d, J=17.2 Hz, NCH$_2$), 4.04, 4.18 (each 1H, d, J=12.8 Hz, SOCH$_2$), 4.65 (1H, m, H$_4$), 4.84 (2H, m, CO$_2$CH$_2$), 5.37 (2H, m, CH$_2$=CH), 6.0 (1H, m, CH$_2$=CH), 6.95 (3H, m, 4-FPh-H, NH),), 7.10 (2H, m, 4-FPh-H), 7.36 (2H, m, 4-CO$_2$allylPh-H), 8.09 (2H, m, 4-CO$_2$allylPh-H), ν$_{c=o}$ 1795 cm$^{-1}$. Found: C, 63.5; H, 6.2; N, 5.4%. C$_{28}$H$_{33}$FN$_2$O$_5$S requires: C, 63.6; H, 6.3; N, 5.3%

EXAMPLE 166

N-(6-{-4-Fluorophenyl}hexyl)-4-(4-carboxybenzylsulphinyl-2-oxoazetidin-1-yl)acetamide (Diastereoisomer 2)

A solution of N-(6-{4-fluorophenyl}hexyl)-4-(4-allyloxycarbonylbenzylsulphinyl-2-oxoazetidin-1-yl)acetamide (diastereoisomer 2) (0.35 g, 0.662 mmoles), triphenylphosphine (0.18 g, 0.686 mmoles) and tetrakis(triphenylphospine)palladium(0) (22 mg) was treated with a solution of pyrollidine (0.048 g, 0.675 mmoles) in dry dichloromethane (1 ml). The reaction mixture was stirred for 22 h. Purification by column chromatography eluted with CH$_2$Cl$_2$, 1:1 CH$_2$Cl$_2$:acetone, 50:50:1 CH$_2$Cl$_2$:acetone:glacial acetic acid and washing with dichloromethane and ether gave the product as a colourless solid, m.p. 185–186° C. (67% yield). $^1$H NMR δ (DMSO) 1.26 (4H, m, 2xCH$_2$), 1.38 (2H, m, CH$_2$), 1.50 (2H, m, CH$_2$), 2.96, 2.99 (1H, dd, J=2, 15.2 Hz, H$_3$), 3.06 (2H, m, NHCH$_2$), 3.84, 4.09 (each 1H, d, J=17.2 Hz, NCH$_2$), 4.13, 4.31 (each 1H, d, J=12.8 Hz, SOCH$_2$), 4.84 (1H, m, H$_4$), 7.05 (2H, m, 4-FPh-H), 7.19 (2H, m, 4-FPh-H), 7.47 (2H, d, J=8 Hz, 4-CO$_2$allylPh-H), 7.93 (2H, d, J=8 Hz, 4-CO$_2$allylPh-H), 8.10 (1H, m, NH), 13 (1H, bs, CO$_2$H). Found: C, 60.9; H, 5.9; N, 5.7%. C$_{25}$H$_{29}$FN$_2$O$_5$S.0.136H$_2$O requires: C, 61.2; H, 6.0; N, 5.7%

EXAMPLE 167

N-(6-{4-Fluorophenyl}hexyl)-4-(4-isopropyloxycarbonylbenzylsulphinyl-2-oxoazetidin-1-yl)acetamide (Diastereoisomer 2)

To a solution of N-(6-{4-fluorophenyl}hexyl)-4-(4-carboxybenzylsulphinyl-2-oxoazetidin-1-yl)acetamide (0.3 g, 0.6 mmol) in N-methyl pyrrolidin-2-one (4 ml) was added anhydrous potassium carbonate (0.7 g, 5 mmol) and 2-iodopropane (0.9 g, 5 mmol). The mixture was stirred for 18 h at room temperature, treated with aqueous brine and extracted with ethyl acetate. The organic extract was washed with water, dried (MgSO$_4$) and evaporated. The residue was purified by flash chromatography using a) ethyl acetate and b) ethyl acetate:methanol (95:5) as the eluting solvents. Evaporation of the appropriate fractions gave the tiltle compound as a white powder (0.3 g, 75%), mp 119° C.

$^1$H NMR δ (CDCl$_3$) 1.33–1.41 (10H, m), 1.45–1.58 (4H, m), 2.56 (2H, t, J=7.5 Hz), 2.92 (1H, dd, J=2.5, 15.4 Hz), 3.15–3.40 (3H, m), 3.93 and 4.24 (each 1H, d, J=18 Hz), 4.30 and 4.22 (each 1H, d, J=15 Hz), 4.69 (1H, m), 5.25 (1H, m), 6.86–7.15 (5H, m), 7.35 (2H, m), 8.07 (2H, m). Found: C, 63.05; H, 6.46; N, 5.24. C$_{28}$H$_{35}$FN$_2$O$_5$S requires: C, 63.38; H, 6.65; N, 5.24%

The following compounds (Examples 168, 169) were prepared in an analogous manner:

EXAMPLE 168

N-(6-{4-Fluorophenyl}hexyl)-4-(4-propyloxycarbonylbenzylsulphinyl-2-oxoazetidin-1-yl)acetamide (Diastereoisomer 2)

Cream solid, m.p. 113° C., 68% yield. $^1$H NMR δ (CDCl$_3$) 1.03 (3H, t, J=7.4 Hz, CH$_3$), 1.30–1.60 (8H, m, 4xCH$_2$), 1.80 (2H, m, CH$_2$CH$_3$) 2.56 (2H, t, J=7.6 Hz, CH$_2$Ph), 2.90, 2.94 (1H, dd, J=2.4, 15.6 Hz, H$_3$), 3.22 (3H, m, NHCH$_2$, H$_3$), 3.94, 4.22 (each 1H, d, J=17.2 Hz, NCH$_2$), 4.04, 4.18 (each 1H, d, J=12.8 Hz, SOCH$_2$), 4.30 (2H, t, J=6.6 Hz, CO$_2$CH$_2$), 4.65 (1H, m, H$_4$), 6.95 (3H, m, 4-FPh-H, NH),), 7.10 (2H, m, 4-FPh-H), 7.36 (2H, m, 4-CO$_2$propylPh-H), 8.07 (2H, m, 4-CO$_2$propylPh-H). ν$_{c=o}$ 1795 cm $^{-1}$. Found: C, 62.4; H, 6.4; N, 5.3%. C$_{28}$H$_{35}$FN$_2$O$_5$S.1% H$_2$O requires: C, 62.7; H, 6.7; N, 5.2%

EXAMPLE 169

N-[6-(4-Fluorophenyl)hexyl]-[4-(4-ethyloxycarbonylbenzyl)sulphinyl-2-oxo-azetidin-1-yl]-acetamide (Diastereoisomer 2)

Off-white solid, 82% yield, m.p. 130–31° C. $^1$H NMR δ (CDCl$_3$) 1.3–1.6(11H, m), 2.55(2H, t), 2.91(1H, dd), 3.25 (1H, dd), 3.27(2H, m), 3.94 & 4.23(each 1H, d, J=20 Hz), 4.17 & 4.02(each 1H, d=12.5 Hz), 4.39(2H, q), 4.65(1H, dd), 7.01(5H, m), 7.35 & 8.07(each 2H, d, J=8.27 Hz).

Found: C, 62.6; H, 6.3; N, 5.4% C$_{29}$H$_{33}$FN$_2$O$_5$S requires: C, 62.8; H, 6.4; N, 5.4%

EXAMPLE 170

N-(6-[4-Fluorophenyl]hex-1-yl)-4-carboxybenzylthio)-2-oxoazetidin-1-yl acetamide Treatment of N-(6-[4-fluorophenyl]hex-1-yl)-4-allyloxycarbonylbenzylthio)-2-oxoazetidin-1-yl acetamide under the conditions described in Example 166 gave the title compound as a colourless oil, 62% yield. $^1$H NMR δ 1.24 (4H, bm), 1.41–1.51 (4H, bm), 2.50 (3H, t, J=7.4 Hz), 2.87–2.93 (1H, bdd), 3.09–3.47 (4H, m) 3.6–3.80 (3H, m), 4.86 (1H, bm), 6.75 (1H, bm), 6.86–6.96 (2H, m), 7.03–7.09 (2H, m), 7.26 (2H,m), 7.97 (2H,m)

EXAMPLE 171

N-(6-[4-Fluorophenyl]hex-1-yl)-(4-methoxycarbonylbenzylthio)-2-oxoazetidin-1-yl acetamide N-(6-[4-fluorophenyl]hex-1-yl)-4-carboxybenzylthio)-2-oxoazetidin-1-yl acetamide (1 g, 2.1 mmol) was dissolved in dry dichloromethane (5 ml) and the solution treated with a solution of trimethylsilyldiazomethane (6 ml of 2M hexane solution) over a period of 3 hours with stirring. Solvent was removed and the residue was chromatographed on silica using dichloromethane:methanol (9:1) as the eluting solvent. Evaporation of the appropriate fractions gave the title compound as an oil (0.27 g, 26% yield).

$^1$H NMR δ 1.32 (4H, bm), 1.4–1.7 (4H, bm), 2.56 (3H, t, J=7.4 Hz), 2.9 (1H, dd, J=2.5, 15.3 Hz), 3.15–3.35 (3H, m), 3.4–4.0 (7H, m), 4.86 (1H, m), 5.99 (1H, bm), 6.90–6.98 (2H, m), 7.07–7.13 (2H, m), 7.40 (2H, m), 7.97 (2H, m)

EXAMPLE 172

N-[6-(4-Fluorophenyl)hexyl]-[4-(4-methyloxycarbonylbenzyl)sulphinyl-2-oxo-azetidin-1-yl]-acetamide (Diastereoisomer 2)

Treatment of N-(6-[4-fluorophenyl]hex-1-yl)-(4-methoxycarbonylbenzylthio)-2-oxoazetidin-1-yl acetamide with mCPBA as described in Examples 2 and 3 gace the title compound as a waxy solid, 26% yield. $^1$H NMR δ 1.34 (3H, bm) 1.4–1.7 (4H, m), 155–1.70 (4H, m), 2.50 (3H, t), 2.95

(1H, dd), 3.15–3.3 (3H,m), 3.9–4.3 (7H, m), 4.6 (1H, m), 6.94 (2H, t), 7.12 (2H, t), 7.36 (2H, d). 8.06 (2H, d), 8.06 (2H, d). $\nu_{c=o}$1795 cm$^{-1}$. Found: C, 61.72; H, 6.17; N, 5.5%. $C_{26}H_{31}FN_2O_5S$ requires: C, 62.13; H, 6.22; N, 5.6%

EXAMPLE 173

N-(6-{4-Chlorophenyl}hexyl)-4-(4-isopropyloxycarbonylbenzylsulphinyl-2-oxoazetidin-1-yl)acetamide (Diastereoisomer 2).

Treatment of N-(6-{-4-chlorophenyl}hexyl)-4-(4-carboxybenzylsulphinyl-2-oxoazetidin-1-yl)acetamide (Diastereoisomer 2) (Example 130) with isopropyl iodide using the method described in Example 169 gave the title compound as white crystals, 78% yield, m.p. 114.5° C. Found: C, 61.45; H, 6.35; N, 5.26%. $C_{28}H_{35}ClN_2O_5S$ requires: C, 61.47; H, 6.45; N, 5.12%.

EXAMPLE 174

N-(6-{4-Chlorophenyl}hexyl)-4-(4-propyloxycarbonylbenzlsulphinyl-2-oxoazetidin-1-yl)acetamide (Diastereoisomer 2).

Treatment of N-(6-{4-chlorophenyl}hexyl)-4-(4-carboxybenzylsulphinyl-2-oxoazetidin-1-yl)acetamide (Diastereoisomer 2) (Example 130) with n-propyl iodide using the method described in Example 169 gave the title compound as a white powder, 69% yield, m.p. 104° C. $^1$H NMR δ (CDCl$_3$) 1.03 (3H, t, J=7.4 Hz), 1.36 (4H, m), 1.55 (4H, m), 1.81 (2H, m), 2.56 (2H, t, J=7.9 Hz), 2.89 (1H, dd, J=2.5, 15.3 Hz), 3.23 (3H, m), 3.90 and 4.16 (each 1H, d, J=17.1 Hz), 4.00 and 4.27 (each 1H, d, J=12.9 Hz), 4.32 (t, J=7.4 Hz), 4.63 (1H, m), 7.01 (1H, bm), 7.06 (2H, d, J=8.4 Hz), 7.20 (2H, d, J=8.4 Hz), 7.34 (2H, d, J=8.3 Hz), 8.05 (2H, d, J=8.3 Hz).

EXAMPLE 175

N-(6-{4-Chlorophenyl}hexyl)-4-(4-ethyloxycarbonylbenzylsulphinyl-2-oxoazetidin-1-yl)acetamide (Diastereoisomer 2).

Treatment of N-(6-{4-chlorophenyl}hexyl)-4-(4-carboxybenzylsulphinyl-2-oxoazetidin-1-yl)acetamide (Diastereoisomer 2) (Example 130) with ethyl iodide using the method described in Example 169 gave the title compound as a white powder, 70% yield, m.p. 124° C. 1.33 (4H, m), 1.40 (3H, t, J=7.1 Hz), 1.55 (4H, m), 2.56 (t, J=7.4 Hz), 2.88 (1H, dd, J=<2, 17.7 Hz), 3.19–3.27 (3H, m), 3.90 and 4.19 (each 1H, d, J=17.1 Hz), 4.01 and 4.16 (each 1H, d, J=12.9 Hz), 4.35 (2H, q, J=7.2 Hz, 7.01 (1H, bm), 7.06 (2H, d, J=8.4 Hz), 7.24 (2H, d, J=8.4 Hz), 7.34 (2H, d, J=8.3 Hz), 8.05 (2H, d, J=8.3 Hz).

EXAMPLE 176

N-[6-(4-Fluorophenyl)hexyl]-[4-(4-(allyloxycarbonylmethyl)benzyl)thio-2-oxo-azetidin-1-yl]-acetamide Treatment of 4-(4-(allyloxycarbonylmethyl)benzylthio) azetidin-2-one with N-(6-(-4-fluorophenyl)hexyl)-1-bromoacetamide by the method described in Example 85a gave the title compound as a olourless oil, 16% yield. $^1$H NMR δ (CDCl$_3$) 1.30–1.60(8H, m), 2.56(2H, t), 3.00–2.95 (1H, dd), 2.97&3.57(each 1H, dd), 3.23(1H, m), 3.42(1H, dd), 3.65(2H, s), 3.77(2H, q), 4.59(2H, m), 4.88 (1H, dd), 5.23–5.32(2H, m), 5.9(1H, m), 6.1 (1H, t), 6.9–7.30 (8H, m)

Treatment of N-(6-(4-fluorophenyl)hexyl)-4-(4-(allyloxycarbonylmethyl)benzylthio-2-oxoazetidin-1-yl) acetamide with mCPBA followed by recrystallisation as described for Example 2 and 3 gave the compounds described in Examples 178 and 179.

EXAMPLE 177

N-[6-(4-Fluorophenyl)hexyl]-[4-(4-(allyloxycarbonylmethyl) benzyl)sulphinyl-2-oxo-azetidin-1-yl]-acetamide (Diastereomer 1)

White crystalline solid, 16% yield, m.p.132–33° C.
Found: C, 63.3; H, 6.3; N, 5.0%. $C_{29}H_{35}FN_2O_5S0.5H_2O$ requires: C, 63.2; H, 6.6; N, 5.1%

EXAMPLE 178

N-[6-(4-Fluorophenyl)hexyl]-[4-(4-(allyloxycarbonylmethyl) benzyl)sulphinyl-2-oxo-azetidin-1-yl]-acetamide (Diastereomer 2)

White crystalline solid, 56% yield, m.p.106–9° C.
Found: C, 64.2; H, 6.4; N, 5.1%. $C_{29}H_{35}FN_2O_5S$ requires: C, 64.2; H, 6.4; N, 5.2%

EXAMPLE 179

N-[6-(4-Fluorophenyl)hexyl]-[4- (4-carboxymethyl) benzyl)thio-2-oxo-azetidin-1-yl]-acetamide Treatment of N-[6-(4-fluorophenyl)hexyl]-[4-(4-(allyloxycarbonylmethyl)-benzyl)thio-2-oxo-azetidin-1-yl]-acetamide under the conditions described for Example 166 gave the title compound as a white solid, 87% yield, m.p. $^1$H NMR δ (CDCl$_3$) 1.21 (4H, m), 1.45 (2H, m), 1.58 (4H, m), 2.56 (2H, t, J=7.6 Hz), 2.84 and 3.47 (each 1H, d, J=16.9 Hz), 2.90 (1H, dd, J=<2, 16.6 Hz), 3.14 (2H, m), 3.39 (1H, dd, J=5.3, 15.1 Hz), 3.64 (2H, s), 3.69 (2H, dd, J=7.7, 14.3 Hz), 4.86 (1H, m), 6.29 (1H, bm), 6.91–7.26 (8H, m).

EXAMPLE 180

N-[6-(4-Fluorophenyl)hexyl]-[4-(4-(carboxymethyl) benzyl sulphinyl-2-oxo-azetidin-1-yl]-acetamide (Diastereomer 1)

Ozonised oxygen was bubbled through a solution of N-[6-(4-fluorophenyl)hexyl]-[4-(4-(carboxymethyl)benzyl) thio-2-oxo-azetidin-1-yl]-acetamide (1.5 g, 3 mmol) in dichloromethane (100 ml) at −78° C. until a pale blue colour persisted. Nitrogen was purged through the reaction, the mixture allowed to reach room temperature and evaporated to dryness. The residue was crystallised from ethyl acetate to give the title compound (0.49 g, 33%) m.p. 160–61° C. $^1$H NMR δ (DMSO-d$_6$) 1.26 (4H, m), 1.38 (2H, m), 1.53 (2H, m), 2.54 (2H, t, J=7.6 Hz), 3.04 (3H, m), 3.14 (1H, dd, J=1.6,>12 Hz), 3.57 (2H, s), 3.57 and 4.00 (each 1H, d, J=21.6 Hz), 3.80 and 4.10 (each 1H, J=13.2 Hz), 4.89 (1H, m), 7.05–7.26 (8H, m), 7.98 (1H, bm), 12.3 (1H, bs).

EXAMPLE 181

N-[6-(4-Fluorophenyl)hexyl]-[4-(4-(carboxymethyl) benzyl)sulphinyl-2-oxo-azetidin-1-yl]-acetamide (Diastereomer 2)

Evaporation of the filtrate from the above crystallisation gave diastereomer 2 contaminated with diastereomer 1 (ratio 65:35) (0.31 g, 20%) m.p. 125–129° C. $^1$H NMR δ (DMSO- $d_6$) 1.26 (4H, m), 1.37 (2H, m), 1.51 (2H, m), 2.55 (2H, m), 2.91 (1H, dd, J=2.4, 15.2 Hz), 3.06 (2H, m), 3.29 (1H, m), 3.57 (2H, s), 3.99–4.21 (4H, m), 4.82 (1H, m), 7.05–7.29 (8H, m), 8.13 (1H, bm), 12.32 (1H, bs).

EXAMPLE 182

N-2,4-Dichlorobenzyl-(4-benzylthio-2-oxoazetidin-1-yl)acetamide

Treatment of (4-benzylthio-2-oxoazetidin-1-yl)acetic acid with 2,4-dichlorobenzylamine under the conditions described for Example 86 gave the title compound as a colourless solid, m.p. 132–133° C., 72% yield. $^1$H nmr δ (CDCl$_3$) 2.93, 2.97 (1H, dd, J=2.4, 15.4 Hz, H$_3$), 3.36, 3.39 (1H, dd, J=5.2, 15.4 Hz, H$_3$), 3.56, 3.70 (each 1H, d, J=16.9 Hz, NCH$_2$), 3.76 (2H, s, SCH$_2$), 4.47 (2H, m, NHCH$_2$), 4.80 (1H, m, H$_4$), 6.5 (1H, m, NH), 7.20–7.34 (7H, m, Ph-H, 2,4-diClPh-H), 7.38 (1H, d, J=2 Hz, 2,4-diClPh-H). ν$_{c=o}$ 1776 cm$^{-1}$. Found: C, 55.8; H, 4.5; N, 6.9%. $C_{19}H_{18}Cl_2N_2O_2S$ requires: C, 55.8; H, 4.4; N, 6.8%

Treatment of N-2,4-dichlorobenzyl-(4-benzylthio-2-oxoazetidin-1-yl)acetamide with mCPBA followed by recrystallisation as described in Examples 2 and 3 gave the compounds described in Examples 183 and 184. Treatment of N-2,4-dichlorobenzyl-(4-benzylsulfinyl-2-oxoazetidin-1-yl)acetamide with mCPBA gave Example 185.

EXAMPLE 183

N-2,4-Dichlorobenzyl-(4-benzylsulphinyl-2-oxoazetidin-1-yl)acetamide (Diastereomer 1)

Colourless solid, m.p. 224–226° C., 16% yield. $^1$H nmr δ (DMSO) 3.03, 3.07 (1H, dd, J=4.8, 14.8 Hz, H$_3$), 3.15, 3.18 (1H, dd, J=1.6, 14.8 Hz, H$_3$), 3.78, 4.16 (each 1H, d, J=16.8 Hz, NCH$_2$), 3.85, 4.14 (each 1H, d, J=12.8 Hz, SOCH$_2$), 4.33 (2H, d, J=5.6 Hz, NHCH$_2$), 4.93 (1H, m, H$_4$), 7.32–7.42 (7H, m, Ph-H, 2,4-diClPh-H), 7.61 (1H, d, J=2 Hz, 2,4-diClPh-H), 8.62 (1H, m, NH). Found: C, 51.7; H, 4.2; N,6.4%. $C_{19}H_{18}Cl_2N_2O_3S$ requires: C, 53.7; H, 4.3; N, 6.6%

EXAMPLE 184

N-2,4-Dichlorobenzyl-(4-benzylsulphinyl-2-oxoazetidin-1-yl)acetamide (Diastereomer 2

Colourless solid, m.p. 162–163° C., 45% yield. $^1$H nmr δ (DMSO) 2.91, 2.95 (1H, dd, J=2.2, 15.4 Hz, H$_3$), 3.30 (1H, m, H$_3$), 3.97, 4.21 (each 1H, d, J=17.2 Hz, NCH$_2$), 4.05, 4.20 (each 1H, d, J=12.8 Hz, SOCH$_2$), 4.34 (2H, d, J=5.8 Hz, NHCH$_2$), 4.83 (1H, m, H$_4$), 7.32–7.42 (7H, m, Ph-H, 2,4-diClPh-H), 7.60 (1H, d, J=2 Hz, 2,4-diClPh-H), 8.72 (1H, m, NH). ν$_{c=o}$ 1793 cm$^{-1}$. Found: C, 53.5; H, 4.4; N, 6.6%. $C_{19}H_{18}Cl_2N_2O_3S$ requires: C, 53.7; H, 4.3; N, 6.6%

EXAMPLE 185

N-2,4-Dichlorobenzyl-(4-benzylsulphonyl-2-oxoazetidin-1-yl)acetamide

Colourless solid, m.p. 163–164° C., 77% yield. $^1$H nmr δ (DMSO) 3.08 (1H, m, H$_3$), 3.30 (1H, m, H$_3$), 3.77, 4.19 (each 1H, d, J=17.2 Hz, NCH$_2$), 4.34 (2H, m, NHCH$_2$), 4.66, 4.77 (each 1H, d, J=13.4 Hz, SO$_2$CH$_2$), 5.09 (1H, m, H$_4$), 7.38 (7H, m, Ph-H, 2,4-diClPh-H), 7.62 (1H, m, 2,4-diClPh-H), 8.67 (1H, m, NH). ν$_{c=o}$ 1796 cm$^{-1}$. Found: C, 51.5; H, 4.1; N, 6.3%. $C_{19}H_{18}Cl_2N_2O_4S$ requires: C, 51.7; H, 4.1; N, 6.4%

EXAMPLE 186

N-3,4-Dichlorobenzyl-(4-benzylthio-2-oxoazetidin-1-yl)acetamide

Treatment of (4-benzylthio-2-oxoazetidin-1-yl)acetic acid with 3,4-dichlorobenzylamine under the conditions described for Example 86 gave the title compound as a colourless solid, m.p. 90–91° C., 68% yield. $^1$H nmr δ (CDCl$_3$) 2.94, 2.98 (1H, dd, J=2.4, 15.6 Hz, H$_3$), 3.36, 3.39 (1H, dd, J=5.2, 15.6 Hz, H$_3$), 3.62, 3.70 (each 1H, d, J=16.8 Hz, NCH$_2$), 3.79 (2H, s, SCH$_2$), 4.38 (2H, m, NHCH$_2$), 4.80 (1H, m, H$_4$), 6.5 (1H, m, NH), 7.12 (1H, m, 3,4-diClPh-H), 7.26–7.40 (7H, m, Ph-H, 3,4-diClPh-H). ν$_{c=o}$ 1778 cm$^{-1}$. Found: C, 55.8; H, 4.5; N, 6.9%. $C_{19}H_{18}Cl_2N_2O_2S$ requires: C, 55.8; H, 4.4; N, 6.8%

Treatment of N-3,4-dichlorobenzyl-(4-benzylthio-2-oxoazetidin-1-yl)acetamide with mCPBA followed by recrystallisation as described in Examples 2 and 3 gave the compounds described in Examples 187 and 188. Treatment of N-3,4-dichlorobenzyl-(4-benzylsulfinyl-2-oxoazetidin-1-yl)acetamide with mCPBA gave Example 189.

EXAMPLE 187

N-3,4-Dichlorobenzyl-(4-benzylsulphinyl-2-oxoazetidin-1-yl)acetamide (Diastereomer 1)

Colourless solid, m.p. 213–214° C., 14% yield. $^1$H nmr δ (DMSO) 3.03, 3.06 (1H, dd, J=4.4, 14.8 Hz, H$_3$), 3.15, 3.18 (1H, dd, J=2, 14.8 Hz, H$_3$), 3.78, 4.14 (each 1H, d, J=17.2 Hz, NCH$_2$), 3.85, 4.14 (each 1H, d, J=12.8 Hz, SOCH$_2$), 4.29 (2H, d, J=6 Hz, NHCH$_2$), 4.93 (1H, m, H$_4$), 7.25 (1H, m, 3,4-diClPh-H), 7.31–7.40 (5H, m, Ph-H), 7.52–7.56 (2H, m, 3,4-diClPh-H), 8.62 (1H, m, NH). Found: C, 53.0; H, 4.3; N, 6.5%. $C_{19}H_{18}Cl_2N_2O_3S$ requires: C, 53.7; H, 4.3; N, 6.6%

EXAMPLE 188

N-3,4-Dichlorobenzyl-(4-benzylsulphinyl-2-oxoazetidin-1-yl)acetamide (Diastereomer 2)

Colourless solid, m.p. 155–156° C., 33% yield. $^1$H nmr δ (DMSO) 2.91, 2.95 (1H, dd, J=2.2, 15.3 Hz, H$_3$), 3.30 (1H, m, H$_3$), 3.96, 4.18 (each 1H, d, J=17.2 Hz, NCH$_2$), 4.05, 4.20 (each 1H, d, J=12.8 Hz, SOCH$_2$), 4.31 (2H, d, J=5.9 Hz, NHCH$_2$), 4.83 (1H, m, H$_4$), 7.27 (1H, m, 3,4-diClPh-H), 7.31–7.37 (5H, m, Ph-H), 7.54–7.57 (2H, m, 3,4-diClPh-H), 8.72 (1H, m, NH). ν$_{c=o}$ 1795 cm$^{-1}$. Found: C, 53.7; H, 4.3; N, 6.5%. $C_{19}H_{18}Cl_2N_2O_3S$ requires: C, 53.7; H, 4.3; N, 6.6%

EXAMPLE 189

N-3,4-Dichlorobenzyl-(4-benzylsulphonyl-2-oxoazetidin-1-yl)acetamide

Colourless solid, m.p. 173–174° C., 86% yield. $^1$H nmr δ (DMSO) 3.08 (1H, m, H$_3$), 3.30 (1H, m, H$_3$), 3.76, 4.18 (each 1H, d, J=17.2 Hz, NCH$_2$), 4.31 (2H, d, J=5.9 Hz, NHCH$_2$), 4.66, 4.77 (each 1H, d, J=13.4 Hz, SO$_2$CH$_2$), 5.09 (1H, m, H$_4$), 7.27 (1H, m, 3,4-diClPh-H), 7.38 (5H, s, Ph-H), 7.53–7.59 (2H, m, 3,4-diClPh-H), 8.66 (1H, m, NH). Found: C, 51.6; H, 4.2; N, 6.4%. $C_{19}H_{18}Cl_2N_2O_4S$ requires: C, 51.7; H, 4.1; N, 6.4%

EXAMPLE 190

(3S,4R)-N-(6-{4-Fluorophenyl}hexyl)-(3-chloro-4-benzylthio-2-oxoazetidin-1-yl)acetamide a. (3S,4R)-(4-Benzylthio-3-chloro-2-oxoaxetidin-1-yl) acetic acid A suspension of methyl [(3S,4R)-4-benzylthio-3-chloro-2-oxoaxetidin-1-yl)acetate (2.87 g, 0.00957 mol) (Example 305) in methanol (50 ml) was cooled to 10° C. and 1N aq. sodium hydroxide (9.6 ml) was added over 40 minute. The cooling bath was removed and reaction was stirred for 30 min, evaporated to remove methanol, diluted with water and washed with ethyl acetate. The aqueous layer was acidified with dilute hydrochloric acid and extracted with ethyl acetate (x2). The organic extracts were combined and washed with brine, dried (MgSO$_4$), evaporated to an oil. Precipitation from ether-pet. ether gave the product as colourless solid, 1.15 g (42%, m.p. 132–134° C.).

b. (3S,4R)-N-(6-{4-Fluorophenyl}hexyl)-(3-chloro-4-benzylthio-2-oxoazetidin-1-yl)acetamide Treatment of (3S,4R)-(4-benzylthio-3-chloro-2-oxoazetidin-1-yl)acetic acid with 6-(4-fluorophenyl) hexylamine under the conditions described for Example 86 gave the title compound as a colourless oil, 85% yield. $^1$H NMR δ (CDCl$_3$) 1.3–1.6 (8H, m, 4xCH$_2$), 2.56 (2H, t, J=7.6 Hz, CH$_2$Ph), 3.22 (2H, m, NHCH$_2$), 3.51, 3.81 (each 1H, d, J=16.5 Hz, NCH$_2$), 3.83 (2H, s, SCH$_2$), 4.58 (1H, d, J=1.7 Hz, H$_4$), 4.79 (1H, d, J=1.7 Hz, H$_3$), 5.80 (1H, m, NH), 6.95 (2H, m, 4-FPh—H), (2H, m, 4-FPh—H), 7.30 (5H, m. Ph—H)

Treatment of (3S,4R)-N-(6-{4-fluorophenyl}hexyl)-(3-chloro-4-benzylthio-2-oxoazetidin-1-yl)acetamide with mCPBA under the conditions described for Examples 2 and 3 gave the compounds described in Examples 191 and 192.

EXAMPLE 191

(SR,3S,4R)-N-(6-{4-Fluorophenyl}hexyl)-3-chloro-4-benzylsulphinyl-2-oxoazetidin-1-yl)acetamide Colourless solid, m.p. 135–136° C., 18% yield. $^1$H NMR δ (CDCl$_3$) 1.3–1.6 (8H, m 4xCH$_2$), 2.56 (2H, t, J=7.8 Hz, CH$_2$Ph), 3.22 (2H, m, NHCH$_2$), 3.80 , 4.13 (each 1H, d, J=17.2 Hz, NCH$_2$), 4.08, 4.23 (each 1H, d, J=13.2 Hz, SOCH$_2$), 4.67 (1H, d, J=1.6 Hz, H$_4$), 5.38 (1H, d, J=1.6 Hz, H$_3$), 6.47 (1H, m, NH), 6.95 (2H, m, 4-FPh—H), 7.10 (2H, m, 4-FPh—H), 7.39 (5H, m. Ph—H). υ$_{C=O}$ 1808 cm$^{-1}$. [α]$_D$ at 25° C.=–117.4 (0.973% w/v CHCl$_3$). Found: C, 60.1; H, 5.8; N, 5.9%. C$_{24}$H$_{28}$ClFN$_2$O$_3$S requires: C, 60.2; H, 5.9; N, 5.9%

EXAMPLE 192

(SS,3S,4R)-N-(6-{4-Fluorophenyl}hexyl)-(3-chloro-4-benzylsulphinyl-2-oxoazetidin-1-yl)acetamide Colourless solid, m.p. 87–89° C., 52% yield. $^1$H NMR δ (CDCl$_3$) 1.3–1.6 (8H, m, 4xCH$_2$), 2.56 (2H, t, J=7.6 Hz, CH$_2$Ph), 3.26 (2H, m, NHCH$_2$), 3.92, 4.28 (each 1H, d, J=17.2 Hz, NCH$_2$), 4.10, 4.18 (each 1H, d, J=13.2 Hz, SOCH$_2$), 4.65 (1H, d, J=2 Hz, H$_4$), 4.72 (1H, d, J=2 Hz, H$_3$), 6.95 (2H, m, 4-FPh—H), 7.09 (1H, m, NH), 7.10 (2H, m, 4-FPh—H), 7.39 (5H, m. Ph—H). υ$_{C=O}$ 1809 cm$^{-1}$. [α]$_D$ at 25° C.=+75.3 (0.908% w/v CHCl$_3$). Found: C, 60.2; H, 5.9; N, 5.9%. C$_{24}$H$_{28}$ClFN$_2$O$_3$S requires: C, 60.2; H, 5.9; N, 5.9%

EXAMPLE 193

N-(6-(4-Fluorophenyl)hexyl)-(3S,4R)-4-benzylthio-3-((R)-hydroxyethyl)-2-oxoazetidin-1-ylacetamide (a) (3S,4R)-4-Benzylthio-3-((R)-(t-butyldimethylsilyloxy)ethyl)-2-azetidinone Treatment of (3R,4R)-4-acetoxy-3-((R)-(t-butyldimethylsilyloxy)ethyl)-2-azetidinone with sodium benzylthiolate as described in Example 1a gave the title compound as a waxy solid, m.p. 69–70° C., 95% yield. $^1$H NMR δ (CDCl$_3$) 0.01 (6H, 2xs, SiCH$_3$), 0.83 (9H, s, tBu—H), 1.13 (3H, d, J=6 Hz, CH$_3$), 3.14 (1H, m, H$_3$), 3.82 (2H, s, SCH$_2$), 4.15 (1H, m, CH$_3$CH), 4.75 (1H, d, J=2 Hz, H$_4$), 5.36 (1H, br s, NH), 7.28 (5H, m, Ph—H)

(b) N-(6-(4-Fluorophenyl)hexyl)-(3S,4R)-4-benzylthio-3-((R)-(t-butyldimethylsilyloxy)ethyl)-2-oxoazetidin-1-ylacetamide Treatment of (3S,4R)-4-benzylthio-3-((R)-(t-butyldimethylsilyloxy)ethyl)-2-azetidinone with N-(6-(4-fluorophenyl)hexyl)-1-bromo0acetamide as described in Example 85 gave the title compound as a colourless oil, 54% yield. $^1$H NMR δ (CDCl$_3$) 0.01 (6H, 2xs, SiCH$_3$), 0.82 (9H, s, tBu—H), 1.07 (3H, d, J=6 Hz, CH$_3$), 1.3–1.6 (8H, m, 4xCH$_2$) 2.56 (2H, t, J=8 Hz, CH$_2$Ar), 3.14 (1H, m, H$_3$), 3.25 (2H, m, NHCH$_2$), 3.54, 3.81 (2H, 2xd, J=17 Hz, NCH$_2$), 3.82 (2H, s, SCH$_2$), 4.20 (1H, m, CH$_3$CH), 4.75 (1H, d, J=2 Hz, H$_4$), 6.40 (1H, br t, NH), 6.95, 710 (4H, 2xm, FPh—H), 7.30 (5H, m, Ph—H)

(c) N-(6-(4-Fluorophenyl)hexyl)-(3S,4R)-4-benzylthio-3-((R)-hydroxyethyl)-2-oxoazetidin-1-ylacetamide N-(6-(4-Fluorophenyl)hexyl)-(3S,4R)-4-benzylthio-3-((R)-(t-butyldimethylsilyloxy)ethyl)-2-oxoazetidin-1-ylacetamide (2.68 g; 4.57 mmoles) and glacial acetic acid (0.4 ml) were dissolved in dry THF (50 ml) and a molar solution of tetrabutylammonium fluoride in THF (6.9 ml; 6.9 mmoles) added. The solution was refluxed for 24 hours, more TBAF (2 ml; 2 mmoles) added and refluxing continued for a further 24 hours. The solution was poured into water (50 ml) and ethyl acetate (50 ml), separated and the organics washed with water, brine, dried over magnesiunm sulphate and evaporated to a brown solid which was recrystallised from ethyl acetate/ether to give a cream solid (1.69 g) m.p. 102–4° C., 78% yield. $^1$H NMR δ (CDCl$_3$) 1.2–1.7 (11 H, m, 4xCH$_2$+CH$_3$), 2.34 (1H, br s, OH) 2.56 (2H, t, J=8 Hz, CH$_2$Ar), 3.20 (3H, m, NHCH$_2$+H$_3$), 3.31, 3.92 (2H, 2xd, J=17 Hz, NCH$_2$), 3.79 (2H, s, SCH$_2$), 4.34 (1H, m, CH$_3$CH), 4.76 (1H, m, H$_4$), 6.64 (1H, br t, NH), 6.95, 7.09 (4H, 2xm, FPh—H), 7.25 (5H, m, Ph—H)

EXAMPLE 194

N-(6-(4-Fluorophenyl)hexyl)-(3S,4R)-4-benzylsulphinyl-3-((R)-hydroxyethyl)-2-oxoazetidin-1-ylacetamide (Diastereomer 2).

Treatment of N-(6-(4-fluorophenyl)hexyl)-(3S,4R)-4-benzylthio-3-((R)-hydroxyethyl)-2-oxoazetidin-1-ylacetamide with mCPBA as described for Example 2 gave the title compound as a colourless solid, m.p. 164–7° C., 17% yield. $^1$H NMR δ (CDCl$_3$) 1.3–1.7 (11H, m, 4xCH$_2$+CH$_3$), 2.45 (1H, m, OH) 2.56 (2H, t, J=8 Hz, CH$_2$Ar), 3.25 (2H, m, NHCH$_2$), 3.40 (1H, m, H$_3$), 3.8–4.25 (4H, m, NCH$_2$+SOCH$_2$), 4.33 (1H, m, CH$_3$CH), 4.69 (1H, m, H$_4$), 6.95, 7.09 (4H, 2xm, FPh—H), 7.2–7.5 (6H, m, Ph—H+NH). υ$_{C=O}$ 1782 cm$^{-1}$. Found: C, 63.6; H, 6.7; N, 5.8%. C$_{26}$H$_{33}$FN$_2$O$_4$S requires: C, 63.9; H, 6.8; N, 5.7%

EXAMPLE 201

N-(6-phenylhexyl)-(4-(4-methoxyphenylthio)-2-oxoazetidin-1-yl)acetamide a. Methyl-(4-methoxyphenylthio-2-oxoazetidin-1-yl) acetate To a solution of 4-(4-methoxyphenylthio)azetidin-2-one (H. Gu et al., J. Org. Chem., 1990, 55, 5655) (11.6 g, 55 mmol), methyl bromoacetate (9.2 g, 60 mmol) and tetrabutylammonium bromide (1.8 g, 0.56 mmol) in dry THF (300 ml) was added powdered potassium hydroxide (3.4 g, 60 mmol). The resulting mixture was stirred for two hours at room temperature before water (100 ml) was added. The solution was extracted with ethyl acetate (3×150 ml portions) and the combined extracts dried (MgSO$_4$) and evaporated. The residue was purified by flash chromatography on silica gel eluted with ethylacetate/hexane (1:1→2:1) to give the product as a solid mp 101–103° C. 58% yield 1H NMR δ (CDCl$_3$) 2.80 (1H, dd, J=2.2, 15 Hz H$_{3a}$), 3.34 (1H, dd, J=5, 15 Hz, H$_{3b}$), 3.72 (3H, s, OCH$_3$), 3.77, 4.29 (each 1H, d, J=18.00 Hz, NCH$_2$), 3.80 (3H, s, SCH$_3$), 5.07 (1H, m, H$_4$), 6.87 (2H, d, J=10 Hz, 2.6 Ph—H), 7.35 (2H, d, J=10 Hz, 3, 5 Ph—H).

b. (4-(4-Methoxyphenylthio)-2-oxoazetidin-1-yl)acetic acid

To a solution of methyl-(4-methoxyphenylthio-2-oxoazetidin-1-yl)acetate (5.2 g, 18 mmol) in methanol (80 ml) was added, dropwise at 0° C., a solution of 1 N sodium hydroxide (20 ml, 20 mmol). The reaction was stirred for 1 hr and evaporated to dryness. Water (50 ml) was added and the solution acidified to pH 3 with dilute hydrochloric acid and extracted with ethyl acetate (3×100 ml). The combined extracts were dried (MgSO$_4$), evaporated and the residue purified by recrystallisation (hexane/ether) to give the product as a white solid, mp 78–79° C., 79% yield 1H NMR δ (CDCl$_3$) 2.80 (1H, dd, J=1.9, 15 Hz, H$_{3a}$), 3.34 (1H, dd, J=5, 15 Hz, H$_{3b}$), 3.80 (3H, s, OCH$_3$), 3.82, 4.30 (each 1H, d, J=18.00 Hz, NCH$_2$), 5.06 (1H, m, H$_4$), 6.40 (1H, bs, NH), 6.87 (2H, d, J=6.8 Hz, 2, 6 Ph—H), 7.35 (2H, d, J=6.8 Hz, 3, 5 Ph—H).

c. N-(6-phenylhexyl)-(4-(4-methoxyphenylthio)-2-oxoazetidin-1-yl)acetamide

A solution of 6-phenylhexylamine (Morse M. A. et al., Cancer Research, 1991, 1846), (1.4 g, 8 mmol) in DMF (50 ml) was added to DCC (1.6 g, 8 mmol), hydroxybenzotriazole (1.0 g, 8 mmol) and (4-(4-methoxyphenylthio)-2-oxoazetidin-1-yl)acetic acid (2.1 g, 8 mmol) and the mixture stirred for 2 hours at room temperature. Ethyl acetate (250 ml) was added, the precipitate filtered, the filtrate washed with dil NaHCO$_3$, water (x2), dried (MgSO$_4$) and evaporated to an oil which was purified by flash chromatography on silica gel using hexane/ethyl acetate (1:3). Evaporation of the appropriate fractions gave the product as a colourless oil, 77% yield. $^1$H NMR δ (CDCl$_3$) 1.34–1.47 (10H, m, (CH$_2$)$_5$), 2.59 (2H, t, J=7.7 Hz, CH$_2$), 2.83 (1H, dd, J=2.2, 15 Hz, H$_{3a}$), 3.18–3.36 (3H, m, CH$_2$H$_{3b}$), 3.78 (3H, s, OCH$_3$), 3.80, 3.99 (each 1H, d, J=15 Hz, NCH$_2$), 4.95 (1H, m, H$_4$), 6.23 (1H, bt, NH), 6.87 (2H, d, J=6.8 Hz, 2, 6 Ph—H), 7.14–7.39 (7H, m, 3, 5 Ph—H, Ph—H).

EXAMPLE 202

(4R,SR/4S,SS) N-(6-phenylhexyl)-(4-(4-methoxyphenyl)sulfinyl)-2-oxoazetidin-1-yl) acetamide A solution of N-(6-phenylhexyl)-(4-(4-methoxyphenylthio)-2-oxoazetidin-1-yl)acetamide (2.5 g, 5.8 mmol) in dichloromethane (100 ml) was cooled to –70° C. and a solution of m-chloroperbenzoic acid (1.0 g, 6.4 mmol) in dichloromethane (100 ml) added dropwise with stirring over 60 min. After a further 3 h at –60° C., the reaction mixture was shaken with a mixture of saturated aqueous sodium sulphite and saturated sodium hydrogen carbonate. The organic layer was separated, washed with brine, dried (MgSO$_4$) and evaporated to a solid which was titurated with ether and filtered. Two recrystallisations from ethyl acetate gave (R$^C$R$^S$/S$^C$S$^S$) N-(6-phenylhexyl)-(4-(4-methoxyphenyl)sulfinyl)-2-oxoazetidin-1-yl acetamide (0.4 g, 14%) m.p. 123–125° C. Found: C, 64.9; H, 6.6; N, 6.3%; C$_{24}$H$_{30}$N$_2$O$_4$S requires: C, 65.1; H, 6.8; N, 6.3%

EXAMPLE 203

(4R,SS/4S,SR)-N-(6-phenylhexyl)-(4-(4-methoxyphenyl)sulfinyl)-2-oxoazetidin-1-yl) acetamide Evaporation of the filtrate gave a waxy solid which was further purified by chromatography on silica to give a gummy solid as a 9:1 mixture of diastereisomers, in favour of the title compound. Found: C, 64.0; H, 6.8; N, 6.1%; C$_{24}$H$_{30}$N$_2$O$_4$S 0.4 EtOAc requires: C, 64.3; H, 7.0; N, 5.9%

EXAMPLE 204

A solution of N-(6-phenylhexyl)-(4-(4-methoxyphenylthio)-2-oxoazetidin-1-yl)acetamide (2.1 g, 5 mmol) in dichloromethane (100 ml) was cooled to –70° C. and a solution of m-chloroperbenzoic acid (2.0 g, 11 mmol) in dichloromethane (100 ml) added dropwise with stirring over 60 min. After a further 2 h at 20° C., the reaction mixture was shaken with a mixture of saturated aqueous sodium sulphite and saturated sodium hydrogen carbonate. The organic layer was separated, washed with brine, dried (MgSO$_4$) and evaporated to a solid which was recrystallised from ethyl acetate to a white solid, 1.2 g (53% yield, m.p. 93–95° C. Found: C, 62.7; H, 6.6; N, 6.2%; C$_{24}$H$_{30}$N$_2$O$_5$S requires: C, 62.9; H, 6.6; N, 6.1%

EXAMPLE 205

N-(6-phenylhexyl)-(4-(3,4-dimethoxyphenylthio)-2-oxoazetidin-1-yl)acetamide a. 4-(3,4-Dimethoxyphenylthio)azetidin-2-one Sodium (0.9 g, 39 mmol) was dissolved in ethanol (150 ml) and 3,4-dimethoxythiophenol (5.9 g, 35 mmol) added dropwise over 20 minutes keeping the temperature between 20° C.–25° C. whilst bubbling nitrogen through the mixture. After 15 minutes, the reaction was cooled to 5° C. and a solution of 4-acetoxyazetidin-2-one (4.3 g, 33 mmol) in ethanol (50 ml) was added dropwise over 15 minutes whilst maintaining the temperature at 5° C. The mixture was stirred at room temperature for 60 minutes and evaporated to dryness under reduced pressure. Water (400 ml) was added, the mixture extracted with dichloromethane (2×300 ml), the extracts dried (MgSO$_4$) and evaporated under reduced pressure to an oil. The oil was cooled to –20° C. and titurated with ether (400 ml) to give a white solid which was isolated by filtration (4.1 g, 52%) m.p. 145–6° C. $^1$H NMR δ (CDCl$_3$) 2.85 (1H, m, H$_{3a}$), 3.31 (1H, m, H$_{3b}$), 3.88 (3H, s, O—CH$_3$), 3.89 (3H, s, O—CH$_3$), 4.92 (1H, dd, J=4.92, 2.30 Hz, H$_4$), 6.30 (1H, br. singlet, N—H), 6.85 (1H, d, J=8.30 Hz, Ph—H), 7.00 (1H, d, J=2.04 Hz, Ph—H), 7.09 (1H, dd, J=8.25, 2.06 Hz, Ph—H).

b. Methyl-(4-(3,4-dimethoxyphenyl)thio-2-oxoazetidin-1-yl)acetate

Sodium hydride (0.5 g, 12 mmol) in dry DMF (10 ml) was cooled to –5° C. and a solution of 4-(3,4-dimethoxyphenylthio)azetidin-2-one (3 g, 12 mmol) in dry DMF (20 ml) was added dropwise over 15 mins under a nitrogen atmosphere at –5° C. After 15 mins methylbromoacetate (2 g, 12 mmol) was added in one portion, and the mixture stirred for 30 mins at room temperature. The reaction mixture was carefully poured into brine/ice water and ethyl acetate (100 ml) was added. The organic layer was washed with brine (x2), dried (MgSO$_4$) and evaporated to a yellow oil which was purified by flash column chromatography eluted with petroleum ether/ethyl acetate to give the product as a yellow oil (0.96 g, 25% yield).

c. (4-(3,4-Dimethoxyphenylthio)-2-oxoazetidin-1-yl) acetic acid

Prepared according to the general procedure of Example 201b and obtained as a yellow oil.

d. N-(6phenylhexyl)-(4-(3,4-dimethoxyphenylthio)-2-oxoazetidin-1-yl)acetamide

Prepared according to the general procedure of Example 201c and obtained as a colourless oil. $^1$H NMR δ (CDCl$_3$) 1.3–1.7 (8H, m, 4xCH$_2$), 2.59 (2H, t, J=7.6 Hz, CH$_2$Ph), 2.89 (1H, dd, J=2, 15 Hz, H$_3$), 3.23 (2H, m, NHCH$_2$), 3.37 (1H, dd, J=5, 15 Hz, H$_3$), 3.73, 3.96 (each 1H, d, J=17 Hz, NCH$_2$), 3.87 (6H, s, 2xOCH$_3$), 4.99 (1H, m, H$_4$), 6.16 (1H, br s, NH), 6.8–7.3 (8H, m, Ph—H+(CH$_3$O)$_2$Ph—H)

EXAMPLE 206

(4R,SS/4S,SR)-N-(6-phenylhexyl)-(4-3,4-dimethoxyphenylsulfinyl)-2-oxoazetidin-1-yl) acetamide Prepared according to the general procedure of Examples 202 & 3 and obtained as a yellow gum, 33% yield. $^1$H nmr δ (CDCl$_3$) 1.35–1.62 (8H, m, CH$_2$CH$_2$CH$_2$CH$_2$), 2.58 (2H, t, J=7.0 Hz, CH$_2$Ph), 3.15–3.45 (4H, m, H$_{3a}$, H$_{3b}$, NH—CH$_2$), 3.43, 3.82 (2H, dd, J=17.0, 17.0 Hz, N—CH$_2$), 3.90–3.92 (6H, s, 2xOCH$_3$), 4.67 (1H, m, H$_4$), 6.75 (1H, s, NH), 6.96–7.29 (8H, m, Ar—H, SO—Ph-(OMe)$_2$).

EXAMPLE 207

(4R,SR/4S,SS) N-(6-phenylhexyl)-(4-(3,4-dimethoxyphenylsulfinyl)-2-oxoazetidin-1-yl) acetamide Prepared according to the general procedure of Examples 202 & 3 and obtained as a white solid m.p. 126–128° C., 26% yield. $^1$H nmr δ (CDCl$_3$) 1.35–1.59 (8H, m, CH$_2$CH$_2$CH$_2$CH$_2$), 2.59 (2H, t, J=7.0 Hz, CH$_2$Ph), 2.78 (1H, dd, J=15.0, 5.0 Hz, H$_{3b}$), 3.28 (2H, m, NH—CH$_2$). 3.47 (1H, dd, J=15.0, 2.0 Hz, H$_{3a}$), 3.87, 4.20 (2H, dd, J=17.0, 17.0 Hz, N—CH$_2$), 3.93 (6H, s, 2xOCH$_3$), 4.51 (1H, m, H$_4$), 6.73 (1H, s, NH), 6.98–7.28 (8H, m, Ar—H, SO—Ph-(OMe)$_2$).

EXAMPLE 208

N-(6-phenylhexyl)-(4-(4-chlorophenylthio)-2-oxoazetidin-1-yl)acetamide

Prepared from 4-(4-chlorophenyl)azetidin-2-one (H. Gu et. al., J. Org. Chem., 1990, 55, 5655) according to the general procedure of Example 201. White crystalline solid, m.p. 52–4° C., 80% yield $^1$H NMR δ (CDCl$_3$), 1.33 (4H, m, NCH$_2$CH$_2$(CH$_2$)$_2$), 1.48 (2H, m, CH$_2$CH$_2$PhCl), 1.63 (2H, m, NCH$_2$CH$_2$), 2.60 (2H, t, J=7.4 Hz, CH$_2$PhCl), 2.88 (1H, dd J=2.3, 15.3 Hz, H$_{3a}$), 3.21 (2H, m, NHCH$_2$), 3.43 (1H, dd, J=5.0, 15.3 Hz, H$_{3b}$), 3.73, 4.00 (each 1H, d, J=16.6 Hz, NCH$_2$), 5.12 (1H, dd, J=2.3, 5.0 Hz, H$_4$), 7.15–7.39 (Ph—H+ClPh—H).

EXAMPLE 209

4-(Phenylthio)-N-(4-phenyl-2-oxobutyl)azetidin-2-one

To a cooled (cold water bath) solution of 4-phenylthioazetidin-2-one (Iwata-Reuyl et. al., J. Nat. Prod., 1993, 56(8), 1373) (1.9 g, 11 mmol), tetra-n-butylammonium bromide (0.4 g, 1.1 mmol) and 1-bromo-4-phenylbutan-2-one (Tetrahedron, 1970, 26, 5611) (2.7 g, 11.8 mmol) in dry tetrahydrofuran (75 ml) was added freshly powdered potassium hydroxide (1.8 g, 31 mmol), and the mixture stirred vigorously for 2 hr at ambient temperature. Water was added and the product extracted into ethyl acetate, dried (MgSO$_4$) and evaporated to an oil. Treatment with ether/pet. ether (b.p. 40–60) gave the product as a white crystalline solid (1.8 g, 51%), mp 62–4° C. 1H NMR δ (CDCl$_3$), 2.63 (4H, m, CH$_2$CO+CH$_2$Ph), 2.85 (3H, m, CH$_2$Ph+H$_{3a}$), 3.44 (1H, dd, J=5.0, 15.1 Hz, H$_{3b}$) 3.73, 4.27 (each 1H, d, J=18.5 Hz, NCH$_2$), 5.21 (1H, dd, J=2.3, 4.9 Hz, H$_4$), 6.97–7.40 (10H, m, Ph—H). Found: C, 70.0; H, 5.9; N, 4.4%; C$_{19}$H$_{19}$NO$_2$S requires: C, 70.1; H, 5.9; N, 4.3%

The following compounds (examples 210 to 215) were prepared according to the general procedure of Example 209. The (R)- and (S)-4-phenylthioazetidinones for Examples 210 and 211 were prepared by the method describe din A. Basak, Synth. Commun. 23, 1985, 1993

EXAMPLE 210

(S)-4-(Phenylthio)-N-(4-phenyl-2-oxobutyl)azetidin-2-one

Colourless oil, 54% yield $^1$H NMR δ (CDCl$_3$), 2.63 (4H, m, CH$_2$CO+CH$_2$Ph), 2.85 (3H, m, CH$_2$Ph+H$_{3a}$), 3.44 (1H, dd, J=5.0, 15.1 Hz, H$_{3b}$) 3.73, 4.27 (each 1H, d, J=18.5 Hz, NCH$_2$), 5.21 (1H, dd, J=2.3, 4.9 Hz, H$_4$), 6.97–7.40 (10H, m, Ph—H). Found: C, 69.9; H, 6.0; N, 4.4%; C$_{19}$H$_{19}$NO$_2$S requires: C, 70.1; H, 5.9; N, 4.3% [a]$_D$=+92.7° (c 0.49, chloroform, 25° C.)

EXAMPLE 211

(R)-4-(Phenylthio)-N-(4-phenyl-2-oxobutyl)azetidin-2-one

Colourless oil, 63% yield $^1$H NMR δ (CDCl$_3$), 2.63 (4H, m, CH$_2$CO+CH$_2$Ph), 2.85 (3H, m, CH$_2$Ph+H$_{3a}$), 3.44 (1H, dd, J=5.0, 15.1 Hz, H$_{3b}$) 3.73, 4.27 (each 1H, d, J=18.5 Hz, NCH$_2$), 5.21 (1H, dd, J=2.3, 4.9 Hz, H$_4$), 6.97–7.40 (10H, m, Ph—H). Found: C, 69.3; H, 5.9; N, 4.4%; C$_{19}$H$_{19}$NO$_2$S. 0.2 H$_2$O requires: C, 69.4; H, 5.9; N, 4.3%; [a]$_D$=–88.7° (c 0.47, chloroform, 25° C.)

EXAMPLE 212

4-(2-Methoxyphenylthio)-N-(4-phenyl-2-oxobutyl) azetidin-2-one a. 4-(2-Methoxyphenylthio)azetidin-2-one Prepared from 2-methoxythiophenol using the general procedure of example 205a and obtained as a white crystalline solid, m.p. 103–5° C., 81% yield $^1$H NMR δ (CDCl$_3$), 2.95 (1H, m, H$_{3a}$), 3.39, (1H, m, H$_{3b}$), 3.90 (1H, s, CH$_3$OPh), 4.98 (1H, dd, J=2.4, 5.0 Hz, H$_4$), 6.33 (1H, s, NH), 6.96 (2H, m, 3,5-(2-CH$_3$OPh)-H), 7.39 (2H, m, 4,6-(2-CH$_3$OPh)-H).

b. 4-(2-Methoxyphenythio)-N-(4-phenyl-2-oxobutyl) azetidin-2-one

Colourless oil, 76% yield $^1$H NMR δ (CDCl$_3$), 2.59 (2H, m, CH$_2$CO), 2.81 (2H, m, CH$_2$Ph), 2.93 (1H, dd, J=1.7, 14.9 Hz, H$_{3a}$), 3.36 (1H, dd, J=5.0, 151 Hz, H$_{3b}$), 3.77, 4.22 (each 1H, d, J=18.6 Hz, NCH$_2$), 3.86 (3H, s, OCH$_3$), 5.27 (1H, dd, J=2.3, 4.9 Hz, H$_4$), 6.90 (2H, m, 3,5-(2-CH$_3$OPh)-H), 7.12–7.39 (7H, m, 4,6-(2-CH$_3$OPh)-H+Ph—H). Found: C, 67.6; H, 6.0; N, 3.9%; C$_{20}$H$_{21}$NO$_3$S requires: C, 67.6; H, 6.0; N, 3.9%

EXAMPLE 213

4-(3,4-dimethoxyphenylthio)-N-(4-phenyl-2-oxobutyl)azetidin-2-one

Colourless oil, 77% yield $^1$H NMR δ (CDCl$_3$), 2.63–2.70 (2H, m, CH$_2$Ph), 2.77–2.90 (3H, m, COCH$_2$, H$_{3a}$), 3.38 (1H, dd, J=15.03, 4.96 Hz, H$_{3b}$), 3.77 and 4.26 (1H each, d, J=18.41 Hz, N—CH$_2$), 3.86 and 3.87 (3H each, s, OCH$_3$), 5.11 (1H, dd, J=4.94, 2.29, H$_4$), 6.79 (1H, d, J=8.26, Ph—H), 6.90–6.98 (2H, m, Ph—H), 7.12–7.32 (5H, m, Ph—H).

EXAMPLE 214

4-(3,-methoxyphenylthio)-N-(4-phenyl-2-oxobutyl)azetidin-2-one a. 4-(3-methoxyphenylthio)azetidin-2-one Prepared from 3-methoxythiophenol using the general procedure of example 205a and obtained as a white crystalline solid, mp 55–6° C., 86% yield 1H NMR δ (CDCl$_3$) 2.90 (1H, m, H$_{3a}$), 3.38 (1H, m, H$_{3b}$), 3.80 (3H, s, OCH$_3$), 5.02 (1H, dd, J=4.94, 2.33 Hz, H$_4$), 6.64 (1H, br. singlet, N—H), 6.85–6.90 (1H, m, Ph—H), 6.96–7.03 (2H, m, Ph—H), 7.23–7.30 (1H, m, Ph—H).

b. 4-(3-methoxyphenylthio)-N-(4-phenyl-2-oxobutyl)azetidin-2-one

Yellow oil, 86% yield 1H NMR δ (CDCl$_3$) 2.50–2.97 (5H, m, CH$_2$CH$_2$, H$_{3a}$), 3.45 (1H, dd, J=15.0, 4.97 Hz, H$_{3b}$), 3.73, 4.27 (1H each, d, J=18.55 Hz, N—CH$_2$), 3.78 (3H, s, OCH$_3$), 5.24 (1H, dd, J=4.97, 2.34 Hz, H$_4$), 6.84 (1H, m, Ph—H), 6.91–6.96 (2H, m, Ph—H), 7.12–7.31 (6H, m, Ph—H).

EXAMPLE 215

4-(4-methoxyphenylthio)-N-(4-phenyl-2-oxobutyl)azetidin-2-one

White crystalline solid, mp 57–58° C., 80% yield Found: C, 67.4; H, 6.0; N, 4.1%; C$_{20}$H$_{21}$NO$_3$S requires: C, 67.8; H, 6.0; N, 3.9%

EXAMPLE 216

(4R,SR/4S,SS) 4-(Phenylsulphinyl)-N-(4-phenyl-2-oxobutyl)azetidin-2-one

A solution of 4-phenylthio-N-(4-phenyl-2-oxobutyl)azetidin-2-one (2.3 g, 7 mmol) in dichloromethane (80 ml) was cooled to −50 to −60° C. and a solution of m-chloroperbenzoic acid (1.5 g, 9 mmol) in dichloromethane (60 ml) was added dropwise with stirring over 40 min. After a further 2 hr. at −50 to −60° C. another portion of m-chloroperbenzoic acid (61 mg, 0.35 mmol) was added and stirring continued for 30 min. The reaction mixture was then shaken with a mixture of saturated aqueous sodium sulphite and saturated sodium hydrogen carbonate and the organic layer collected, dried (MgSO$_4$) and evaporated. Crystallisation from ether then dichloromethane/ether gave the product as a white crystalline solid, mp 125–6° C., 27% yield 1H NMR δ (CDCl$_3$), 2.78 (2H, m, CH$_2$CO), 2.87 (1H, dd, J=4.7, 15.0 Hz, H$_{3a}$), 2.94 (2H, m, CH$_2$Ph), 3.42 (1H, dd, J=2.0, 15.0 Hz, H$_{3b}$), 3.85, 4.46 (each 1H, d, J=18.9 Hz, CH$_2$N), 4.73 (1H, dd, J=2.1, 4.7 Hz, H$_4$), 7.17–7.35 (5H, m, Ph—H), 7.55 (5H, s, SOPh—H). Found: C, 66.7; H, 5.7; N, 4.2%; C$_{19}$H$_{19}$NO$_3$S requires: C, 66.8; H, 5.6; N, 4.1%

EXAMPLE 217

(4R,SS/4S,SR)-4-(Phenylsulphinyl)-N-(4-phenyl-2-oxobutyl)azetidin-2-one

The combined filtrate from Example 216 was evaporated and the residue purified by flash chromatography (silica, ethyl acetate/pet. ether). the product crystallised from ether to give the product as a white crystalline solid, mp 111–3° C., 16% yield 1H NMR δ (CDCl$_3$), 2.38–2.62 (2H, m, CH$_2$CO), 2.81 (2H, m, CH$_2$Ph), 3.13–3.30 (2H, m, H$_{3a}$+H$_{3b}$), 3.73, 4.30 (each 1H, d, J=18.8 Hz, CH$_2$N), 4.80 (1H, dd, J=2.8, 4.8 Hz, H$_4$), 7.11–7.33 (5H, m, Ph—H), 7.50–7.65 ((5H, m, SOPh—H). Found: C, 66.4; H, 5.6; N, 4.3%; C$_{19}$H$_{19}$NO$_3$S requires: C, 66.8; H, 5.6; N, 4.1%

The following compounds (Examples 218–26) were prepared following the general procedure of Examples 216 and 17.

EXAMPLE 218

(4R,SR)-4-(Phenylsulphinyl)-N-(4-phenyl-2-oxobutyl)azetidin-2-one

White crystalline solid, m.p. 123–4° C., 26% yield from Example 211. 1H NMR δ (CDCl$_3$), 2.78 (2H, m, CH$_2$CO), 2.87 (1H, dd, J=4.7, 15.0 Hz, H$_{3a}$), 2.94 (2H, m, CH$_2$Ph), 3.42 (1H, dd, J=2.0, 150 Hz, H$_{3b}$), 3.85, 4.46 (each 1H, d, J=18.9 Hz, CH$_2$N), 4.73 (1H, dd, J=2.1, 4.7 Hz, H$_4$), 7.17–7.35 (5H, m, Ph—H), 7.55 (5H, s, SOPh—H Found: C, 66.3; H, 5.6; N, 4.4%; C$_{19}$H$_{19}$NO$_3$S. 0.15 H$_2$O requires: C, 66.3; H, 5.7; N, 4.1% [a]$_D$=−309.69° (c 0.42, chloroform, 25° C.)

EXAMPLE 219

(4R,SS)-4-(Phenylsulphinyl)-N-(4-phenyl-2-oxobutyl)azetidin-2-one

White crystalline solid, m.p. 49–51° C., 6% yield from Example 211. 1H NMR δ (CDCl$_3$), 2.38–2.62 (2H, m, CH$_2$CO), 2.81 (2H, m, CH$_2$Ph), 3.13–3.30 (2H, m, H$_{3a}$+H$_{3b}$), 3.73, 4.30 (each 1H, d, J=18.8 Hz, CH$_2$N), 4.80 (1H, dd, J=2.8, 4.8 Hz, H$_4$), 7.11–7.33 (5H, m, Ph—H), 7.50–7.65 (5H, m, SOPh—H). Found: C, 66.3; H, 5.7; N, 4.5%; C$_{19}$H$_{19}$NO$_3$S. 0.15 CH$_3$CN requires: C, 66.7; H, 5.6; N, 4.6% [a]$_D$=+161.8° (c 0.1, chloroform, 25° C.)

EXAMPLE 220

(4R,SR/4S,SS) 4-(2-Methoxyphenylsulphinyl)-N-(4-phenyl-2-oxobutyl)azetidin-2-one White crystalline solid, m.p. 129–31° C., 12% yield 1H NMR δ (CDCl$_3$), 2.79 (3H, m, H$_{3a}$+CH2CO), 2.96 (2H, m, CH$_2$Ph), 3.35 (1H, dd, J=1.6, 14.9 Hz, H$_{3b}$), 3.87 (3H, s, OCH$_3$), 3.93, 4.50 (each 1H, d, J=18.9 Hz, NCH$_2$), 5.13 (1H, dd, J=2.1, 4.7 Hz, H$_4$), 6.93 (1H, d, 3-(2-CH$_3$OPh)-H), 7.16–7.34 (6H, Ph—H+5-(2-CH$_3$OPh)-H), 7.49 (1H, m, 4-(2-CH$_3$OPh)-H), 7.67 (1H, dd, 6-(2-CH$_3$OPh)-H). Found: C, 64.0; H, 5.8; N, 3.9%; C$_{20}$H$_{21}$NO$_4$S. 0.2 H$_2$O requires: C, 64.0; H, 5.8; N, 3.7%

EXAMPLE 221

(4R,SS/4S,SR)-4-(2-Methoxyphenylsulphinyl)-N-(4-phenyl-2-oxobutyl)azetidin-2-one White crystalline solid, m.p. 85–7° C., 31% yield 1H NMR δ (CDCl$_3$), 2.20, 2.44 (2H, m, CH2CO), 2.67 (2H, m, CH$_2$Ph), 3.26–3.45 (2H, m, H$_{3a}$+H$_{3b}$), 3.39, 4.22 (each 1H, d, J=19.1 Hz, NCH$_2$), 3.85 (3H, s, OCH$_3$), 5.36 (1H, dd, J=2.5, 4.9 Hz, H$_4$), 6.83 (1H, d, 3-(2-CH$_3$OPh)-H), 7.08–7.32 (6H, m, 5-(2-CH$_3$OPh)-H+Ph—H), 7.46 (1H, m, 4-(2-CH$_3$OPh)-H), 7.76 (1H, dd, 6-(2-CH$_3$OPh)-H). Found: C, 64.2; H, 5.7; N, 3.7%; C$_{20}$H$_{21}$NO$_4$S requires: C, 64.7; H, 5.7; N, 3.8%

EXAMPLE 222

(4R,SS/4S,SR)-4-(3,4-dimethoxyphenylsulphinyl)-N-(4-phenyl-2-oxobutyl)azetidin-2-one White crystalline solid, m.p. 110–112° C., 11% yield Found: C, 62.6; H, 5.8; N, 3.7%; $C_{21}H_{23}NO_5S$ requires: C, 62.8; H, 5.8; N, 3.5%

EXAMPLE 223

(4R,SR/4S,SS)-4-(3-methoxyphenylsulphinyl)-N-(4-phenyl-2-oxobutyl)azetidin-2-one White crystalline solid, m.p. 94–95° C., 15% yield Found: C, 64.4; H, 5.7; N, 3.9%; $C_{20}H_{21}NO_4S$ requires: C, 64.7; H, 5.7; N, 3.8%

EXAMPLE 224

(4R,SS/4S,SR)-4-(3-methoxyphenylsulphinyl)-N-(4-phenyl-2-oxobutyl)azetidin-2-one White crystalline solid, m.p. 88–90° C., 4% yield Found: C, 64.4; H, 5.7; N, 3.9%; $C_{20}H_{21}NO_4S$ requires: C, 64.7; H, 5.7; N, 3.8%

EXAMPLE 225

(4R,SR/4S,SS)-4-(4-methoxyphenylsulphinyl)-N-(4-phenyl-2-oxobutyl)azetidin-2-one White crystalline solid, m.p. 154–155° C., 42% yield Found: C, 64.6; H, 5.8; N, 3.9%; $C_{20}H_{21}NO_4S$ requires: C, 64.7; H, 5.7; N, 3.8%

EXAMPLE 226

(4R,SS/4S,SR)-4-(4-methoxyphenylsulphinyl)-N-(4-phenyl-2-oxobutyl)azetidin-2-one White crystalline solid, m.p. 67–69° C., 13.5% yield Found: C, 64.6; H, 5.8; N, 3.9%; $C_{20}H_{21}NO_4S$ requires: C, 64.7; H, 5.7; N, 3.8%

EXAMPLE 224

4-Phenylsulphonyl)-N-(4-phenyl-2-oxobutyl)azetidin-2-one

To a cooled and stirring solution of 4-(phenylthio)-N-(4-phenyl-2-oxobutyl)azetidin-2-one (0.5 g, 1.54 mmol) in dichloromethane (20 ml) was added dropwise a solution of m-chloroperbenzoic acid (0.66 g, 3.84 mmol) in dichloromethane (25 ml). The cooling bath was removed and a further portion of m-chloroperbenzoic acid (0.13 g, 0.75 mmol) added to complete the reaction. After 30 min., the mixture was shaken with a mixture of saturated aqueous sodium sulphite and saturated sodium hydrogen carbonate and the organic layer collected, dried (MgSO$_4$) and evaporated to an oil which crystallised under pet. ether. Recrystallisation from dichloromethane-ether gave the title compound as a white solid, yield 0.45 g (82%), m.p. 110–11° C. 1H NMR δ (CDCl$_3$), 2.68 (2H, m, CH$_2$CO), 2.89 (2H, t, CH$_2$Ph), 3.06 (1H, dd, J=1.9, 15.3 Hz, $H_{3a}$), 3.35 (1H, dd, J=5.2, 15.1 Hz, $H_{3b}$), 3.94, 4.41 (each 1H, d, J=18.8 Hz, CH$_2$N), 5.02 (1H, dd, J=2.2, 5.2 Hz, H$_4$), 7.15–7.34 (5H, m, Ph—H), 7.58–7.89 (5H, m, SO$_2$Ph—H). Found: C, 63.4; H, 5.4; N, 4.2%; $C_{19}H_{19}NO_4S$ requires: C, 63.9; H, 5.4; N, 3.9%

EXAMPLE 228

4-(2-Methoxyphenylsulphonyl)-N-(4-phenyl-2-oxobutyl)azetidin-2-one

Prepared according to the general procedure of Example 227 and obtained as a white crystalline solid, m.p. 122–3° C., 70% yield 1H NMR δ (CDCl$_3$), 2.44 (2H, m, CH2CO), 2.57 (2H, m, CH$_2$Ph), 3.37 (2H, m, $H_{3a}$+$H_{3b}$), 3.67, 4.36 (each 1H, d, J=19.0 Hz, NCH$_2$), 3.93 (3H, s, OCH$_3$), 5.49 (1H, dd, J=2.7, 4.7 Hz, H$_4$), 6.99 (1H, d, 3-(2-CH$_3$OPh)-H), 7.11–7.33 (6H, m, 5-(2-CH$_3$OPh)-H+Ph—H), 7.63 (1H, m, 4-(2-CH$_3$OPh)-H), 7.93 (1H, dd, 6-(2-CH$_3$OPh)-H). Found: C, 61.8; H, 5.5; N, 3.7%; $C_{20}H_{21}NO_5S$ requires: C, 62.0; H, 5.5; N, 3.6%

EXAMPLE 229

N-[6-(4-Chlorophenyl)hexyl]-4-(4-methylphenylthio)-2-oxoazetidin-1-ylacetamide a. 6-(3-chlorophenyl)hexyn-1-ol A mixture of 3-chloroiodobenzene (14.3 g, 60 mmol), tetrakis(triphenylphosphine) palladium (2.1 g, 1.8 mmol) and 5-hexyn-1-ol (5.9 g, 60 mmol) in triethylamine (120 ml) was stirred at 25° C. for 3H and partitioned between water and ether. The White crystalline solid, m.p. 88–90° C., 4% yield ether layer was separated and the aqueous extracted with ether. The combined ether extracts were washed with 1N HCl and dried (Na$_2$SO$_4$). The ether was evaporated and the residue purified by flash chromatography on silica using dichloromethane as eluant. Evaporation of the appropriate fractions gave the product alcohol as an oil (11.5 g, 92%).

b. 1-(Phthalimido)-6-(3-chlorophenyl)hex-1yne

A solution of 6-(3-chlorophenyl)hexyn-1-ol (11.5 g, 55 mmol), triphenylphosphine (14.5 g, 55 mol) and phthalimide (8.1 g, 55 mol) in dry THF (110 ml) was treated with a solution of diethylazodicarboxylate (9.6 g, 55 mmol) in THF (20 mol) over several minutes. After 16 h, violates were removed in vacuo and the residue treated with ether. The precipitated solid was removed, the filtrate evaporated and the residue purified by flash chromatography on silica using dichloromethane as eluant. Evaporation of the appropriate fractions gave the product as a solid (16.5 g, 89%)

c. 6-(3-Chlorophenyl)hexylamine

A suspension of 1-(phthalimido)-6-(3-chlorophenyl)hex-1-yne (10 g, 30 mmol) in methanol (100 ml) was treated with platinum oxide (250 mg) and the mixture hydrogenated at 50 psi for 72 h. Further quantities of catalyst were added at intervals and when the theoretical uptake of hydrogen was complete, the mixture was filtered and the filtrate evaporated to a brown oil (9.5 g, 96%). This was dissolved in ethanol (100 ml) and treated with hydrazine hydrate (2.8 g, 56 mmol) under reflux for 16 h. The mixture was cooled to 5° c. and the precipitated solid removed by filtration. Evaporation of the filtrate gave an oil which was taken up in ether, washed with water, dried (Na$_2$SO$_4$) and evaporated to a brown oil (5.8 g, 98%)

d. N-[6-(4-Chlorophenyl)hexyl]-1-bromoacetamide

A cooled solution of 6-(4-chlorophenyl)hexylamine (20 g) and Hunig's base (12.15 g) in dry dichloromethane (250 ml) was treated with bromoacetylbromide (190 g) in dichloromethane (50 ml) at 0–5° C. After workup and chromatography N-[6-(4-chlorophenyl)hexyl]-1-bromoacetamide was obtained as a white solid, (20.4 g, 65% yield), m.p. 63–65° C.

e. 4-Methylphenylthio-2-oxo-azetidin-1-one

4-Methylphenylthio-2-oxo-azetidin-1-one was prepared from 4-methylphenylthiol and 4-acetoxyazetidinone in the presence of sodium ethoxide in ethanol and was isolated as a cream solid, m.p. 105–107° C., 4.3% yield; $^1$H NMR δ (CDCl$_3$) 2.35(3H s, CH$_3$), 2.85,3.32(each 1H, dd, J=2.5,15 Hz, $H_{3a}$), 3.34,3.40 (1H, dd, J=5.15 Hz, $H_{3b}$), 4.93 (1H, m, $H_4$), 5.03 (1H, m, $H_4$), 6.41 (1H, bs, NH), 7.14 (2H, d, J=10 Hz, Ph-H), 7.36 (2H, d, J=10 Hz, Ph-H).

f. N-[6-(4-Chlorophenyl)hexyl]-4-(4-methylphenylthio)-2-oxoazetidin-1-ylacetamide 4-(4-Methylphenylthio)-2-oxoazetidinone (2.5 g) was treated N-[6-(4-chlorophenyl)hexyl]-1-bromoacetamide (4.3 g) in dry THF (100 ml) in the presence of 18-crown-6 (~5 mg) and tetra-n-butylammonium bromide (1.44 g) to give N-[6-(4-chlorophenyl)hexyl]-4-(4-methylphenylthio)-2-oxoazetidin-1-ylacetamide (2.35 g, 43% yield) as colourless microprisms, m.p. 63–65° C., after chromatography. [1] NMR δ (CDCl$_3$)1.28–1.34(2H, m, CH$_2$),1.45–1.60(4H, m, (CH$_2$)$_2$), 2.6 (2H, t, J=7.75 Hz, CH$_2$), 2.89,290(each 1H, dd, J=2.5,15 Hz, H$_{3a}$), 2.85 (2H, q, J=7.5 Hz, NHCH$_2$) 3.34,3.40 (1H, dd, J=5,15 Hz, H$_{3b}$), 3.80,3.96 (each 1H, dd, J=19.00 Hz, NCH$_2$), 5.03 (1H, m, H$_4$), 6.14 (1H, bs, NH), 7.06–7.32 (8H, m, Ph-H).

EXAMPLE 230

(R,R/S,S)-N-[6-(4-chlorophenyl)hexyl]-4-(4-methylphenyl)sulfinyl-2-oxo-azetidinyl-1-yl acetamide Treatment of N-[6-(4-chlorophenyl)hexyl]-4-(4-methylphenylthio)-2-oxoazetidin-1-ylacetamide with mCPBA as for Example 202 gave the title compound as white microprisms after crystallisation from the mixture of diastereoisomers, m.p. 133–134° C., 32% yield; ν$_{c=o}$ 1790,1690 cm$^{-1}$ Found: C, 62.3; H, 6.2; N, 6.0%; C$_{24}$H$_{29}$ClN$_2$O$_3$S requires:C, 62.5; H, 6.3; N, 6.1%

EXAMPLE 231

(R,S/S,R)-N-[6-(4-chlorophenyl)hexyl]-4-(4-methylphenyl)sulfinyl-2-oxo-azetidinyl-1-yl acetamide Evaporation of the mother liquors from the crystallisation in Example 230 yielded the title compound as a waxy solid, m.p. indeterminate, 11% yield; ν$_{c=o}$ 1791,1690 cm$^{-1}$. Found: C, 60.2; H, 6.0; N, 5.8%; C$_{24}$H$_{29}$ClN$_2$O$_3$S.1H$_2$O requires: C, 60.5; H, 6.5; N, 5.9%

EXAMPLE 232

N-[6-(4-chlorophenyl)hexyl]-4-(4-methylphenyl)sulfonyl-2-oxo-azetidinyl-1-yl acetamide Treatment of N-[6-(4-chlorophenyl)hexyl]-4-(4-methylphenylthio)-2-oxoazetidin-1-ylacetamide with mCPBA (2 equivalents) as for Example 204 gave the title compound as white microprisms, m.p. 132–133° C., 71% yield; ν$_{c=o}$ 1794, 1690 cm$^{-1}$ Found:C, 60.1; H, 6.1; N, 5.9%; C$_{24}$H$_{29}$ClN$_2$O$_4$S requires: C, 60.4; H, 6.1; N, 5.9%

EXAMPLE 233

(+/−)-N-[6-(4-Chlorophenyl)hexyl]-4-phenylthio-2-oxoazitedin-1-ylacetamide hydrate Treatment (4-phenylthio-2-oxo)azitedin-1-ylacetic acid with 6-(4-chlorophenyl)hexylamine under the conditions described in Example 201 gave the title compound as colourless crystals, m.p. 57–9° C., 96% yield; Found: C,61.3; H, 6.3; N, 6.3%; C$_{23}$H$_{27}$ClN$_2$O$_2$S.H$_2$O requires: C, 61.5; H, 6.3; N, 6.5%

The above racemic compound (Example 233) was separated by high performance liquid chromatography on a chiral support to give the constitutive enantiomers (Examples 234, 35)

EXAMPLE 234

(−)-N-[6-(4-Chlorophenyl)hexyl]-4-phenylthio-2-oxoazitedin-1-ylacetamide hydrate Colourless oil, [α]$_D^{20}$=−59.9 (CHCl$_3$, c=0.2%w/v)

EXAMPLE 235

(+)-N-[6(4-Chlorophenyl)hexyl]-4-phenylthio-2-oxoazitedin-1-ylacetamide hydrate Colourless oil, [α]$_D^{20}$=+56.0 (CHCl$_3$, c=0.3%)

Treatment of (+/−)-N-[6-(4-chlorophenyl)hexyl]-4-phenylthio-2-oxoazitedin-1-ylacetamide with mCPBA as described for Examples 202 and 203 gave the following sulfoxides (Examples 236, 237).

EXAMPLE 236

(R,R/S,S)-N-[6-(4-Chlorophenyl)hexyl]-4-phenylsulfinyl-2-oxoazetidin-1-ylacetamide Colourless solid, m.p. 110–111° C., 23% yield Found: C, 61.7; H, 6.1; N, 6.3%; C$_{23}$H$_{27}$ClN$_2$O$_3$S requires:C, 61.8; H, 6.1; N, 6.3%

EXAMPLE 237

(R,S/S,R)-N-[6-(4-Chlorophenyl)hexyl]-4-phenylsulfinyl-2-oxoazetidin-1-ylacetamide Colourless crystals, m.p. 85–88° C., 30% yield Found: C, 61.9; H, 6.1; N, 6.3%; C$_{23}$H$_{27}$ClN$_2$O$_3$S requires: C, 61.8; H, 6.1; N, 6.3%

(R,R/S,S)-N-[6-(4-Chlorophenyl)hexyl]-4-phenylsulfinyl-2-oxoazetidin-1-ylacetamide (Example 236) was separated by high performance liquid chromatography on a chiral support to give the constitutive enantiomers (Examples 238, 39).

EXAMPLE 238

(−)-(R,R or S,S)-N-[6-(4-Chlorophenyl)hexyl]-4-phenylsulfinyl-2-oxoazetidin-1-ylacetamide Colourless solid, m.p. 115–118° C., [α]$_D^{20}$=−238.6 (CHCl$_3$, c=0.04% w/v)

EXAMPLE 239

(+)-(R,S or S,R)-N-[6-(4-Chlorophenyl)hexyl]-4-phenylsulfinyl-2-oxoazetidin-1-ylacetamide Colourless solid, m.p. 116–118.5° C., [α]$_D^{20}$=+251.5 (CHCl$_3$, c=0.03% w/v)

(R,S/S,R)-N-[6-(4-Chlorophenyl)hexyl]-4-phenylsulfinyl-2-oxoazetidin-1-ylacetamide (Example 237) was separated by high performance liquid chromatography on a chiral support to give the constitutive enantiomers (Examples 240, 41).

EXAMPLE 240

(+)-(R,S or S,R)-N-[6-(4-Chlorophenyl)hexyl]-4-phenylsulfinyl-2-oxoazetidin-1-ylacetamide Colourless solid, m.p. 115–116.5° C., [α]$_D^{20}$=+188.6 (CHCl$_3$, c=0.04% w/v)

EXAMPLE 241

(−)-(R,R, or S,S)-N-[6-(4-Chlorophenyl)hexyl]-4-phenylsulfinyl-2-oxoazetidin-1-ylacetamide Colourless solid, m.p. 113–115° C., $[\alpha]_D^{20}=-212.8$ (CHCl$_3$, c=0.04% w/v)

EXAMPLE 242

N-[6-(4-Chlorophenyl)hexyl]-4-phenylsulfonyl-2-oxoazetidin-1-ylacetamide

Treatment of (R,R/S,S)-N-[6-(4-Chlorophenyl)hexyl]-4-phenylsulfinyl-2-oxoazetidin-1-ylacetamide with mCPBA in dichloromethane gave the title compound as colourless crystals, m.p. 144–146° C., 92%

Found: C, 59.6; H, 5.9; N, 6.1%; $C_{23}H_{27}ClN_2O_4S$ requires: C, 59.7; H, 5.9; N, 6.1%

(+/−)-N-[6-(4-Chlorophenyl)hexyl]-4-phenylsulfonyl-2-oxoazetidin-1-ylacetamide (Example 242) was separated by high performance liquid chromatography on a chiral support to give the constitutive enantiomers (Examples 243, 244).

EXAMPLE 243

(−)-N-[6-(4-Chlorophenyl)hexyl]-4-phenylsulfonyl-2-oxoazetidin-1-ylacetamide

Colourless solid, m.p. 106–109° C., $[\alpha]_D^{20}=-67.7$ (CHCl$_3$, c=0.07% w/v)

EXAMPLE 244

(+)-N-[6-(4-Chlorophenyl)hexyl]-4-phenylsulfonyl-2-oxoazetidin-1-ylacetamide

Colourless solid, m.p. 110–111° C., $[\alpha]_D^{20}=+69.1$ (CHCl$_3$, c=0.08% w/v)

EXAMPLE 245

N-[6-(4-Chlorophenyl)hexyl]-4-(4-methoxyphenylthio)-2-oxoazetidin-1-ylacetamide

The title compound was prepared by the methods described in Example 201 and was isolated as colourless crystals, m.p. 84–86° C., in 94% yield.

Found: C, 62.4; H, 6.3; N, 6.1%; $C_{24}H_{29}ClN_2O_3S$ requires: C, 62.5; H, 6.3; N, 6.1%

Treatment of N-[6-(4-chlorophenyl)hexyl]-4-(4-methoxyphenylthio)-2-oxoazetidin-1-ylacetamide with mCPBA as described for Examples 202 and 203 gave the following sulfoxide diastereoisomers (Examples 246, 247).

EXAMPLE 246

(R,R/S,S)-N-[6-(4-Chlorophenyl)hexyl]-4-(4-methoxyphenylsulfinyl)-2-oxoazetidin-1-ylacetamide Colourless crystals, m.p. 114–116° C., 39% yield.

Found: C, 60.1; H, 6.0; N, 6.0%; $C_{24}H_{29}ClN_2O_4S$ requires: C, 60.4; H, 6.1; N, 5.9%

EXAMPLE 247

(R,S/S,R)-N-[6-(4-Chlorophenyl)hexyl]-4-(4-methoxyphenylsulfinyl)-2-oxoazetidin-1-ylacetamide Colourless crystals, m.p. 74–77° C., 24% yield Found: C, 60.5; H, 6.0; N, 5.9%; $C_{24}H_{29}ClN_2O_4S$ requires: C, 60.4; H, 6.1; N, 5.9%

EXAMPLE 248

N-[6-(4-Chlorophenyl)hexyl]-4-(4-methoxyphenylsulfonyl)-2-oxoazetidin-1-ylacetamide Treatment of (R,R/S,S)-N-[6-(4-chlorophenyl)hexyl]-4-(4-methoxyphenylsulfinyl)-2-oxoazetidin-1-ylacetamide with mCPBA gave the title compound as colourless crystals, m.p. 105–7° C., 91% yield;

Found: C, 58.6; H, 5.9; N, 5.8%; $C_{24}H_{29}ClN_2O_5S$ requires: C, 58.5; H, 5.9; N, 5.7%

EXAMPLE 249

N-Benzyl-[4-(4-methoxyphenylthio)-2-oxoazetidin-1-yl]acetamide

Treatment of (4-(4-methoxyphenylthio)-2-oxoazetidin-1yl)acetic acid with benzylamine under the conditions described in Example 86 gave the title compound as a colourless oil, 74% yield. $^1$H NMR δ (CDCl$_3$) 2.80, 2.86 (1H, dd, J=2.3, 15.2 Hz, H$_3$), 3.29, 3.35 (1H, dd, J=5, 15.2 Hz, H$_3$), 3.79 (3H, s, OCH$_3$), 3.85, 4.05 (each 1H, d, J=16.7 Hz, NCH$_2$), 4.43 (2H, d, J=5.7 Hz, NHCH$_2$), 4.97 (1H, m, H$_4$) 6.5 (1H, m, NH), 6.83 (2H, d, J=8.6 Hz, 4-OCH$_3$Ph-H), 7.24–7.35 (7H, m, Ph-H, 4-OCH$_3$Ph-H). $\nu_{c=o}$ 1775 cm$^{-1}$. Found: C, 64.0 H, 5.8; N, 8.1%. $C_{19}H_{20}N_2O_3S$ requires: C, 64.0; H, 5.7 N, 7.9%

Treatment of N-benzyl-[4-(4-methoxyphenylthio)-2-oxoazetidin-1-yl]acetamide with mCPBA followed by recryatallisation as described for Examples 2 and 3 gave the compounds described in Examples 250 and 251.

EXAMPLE 250

N-Benzyl-[4-(4-methoxyphenylsulphinyl)-2-oxoazetidin-1-yl]acetamide (Diastereomer 1)

Colourless solid, m.p. 165° C., 35% yield. $^1$H NMR δ (CDCl$_3$) 2.75, 2.81 (1H, dd, J=4.7, 15 Hz, H$_3$), 3.41, 3.47 (1H, dd, J=2.2, 15 Hz, H$_3$), 3.86 (3H, s, OCH$_3$), 3.99, 4.16 (each 1H, d, J=17.2 Hz, NCH$_2$), 4.47 (2H, m, NHCH$_2$), 4.55 (1H, m, H$_4$), 7.05 (2H, m, 4-OCH$_3$Ph-H), 7.1 (1H, m, NH), 7.33 (5H, m, Ph-H), 7.47 (2H, m, 4-OCH$_3$Ph-H). $\nu_{c=o}$ 1791 cm$^{-1}$. Found: C, 61.3 H, 5.4; N, 7.5%. $C_{19}H_{20}N_2O_4S$ requires: C, 61.3; H, 5.4 N, 7.5%

EXAMPLE 251

N-Benzyl-[4-(4-methoxyphenylsulphinyl)-2-oxoazetidin-1-yl]acetamide (Diastereomer 2)

Foam, 21% yield. $^1$H NMR δ (CDCl$_3$) 3.23 (2H, m, 2x, H$_3$), 3.35, 3.89 (each 1H, d, J=16.9 Hz, NCH$_2$), 3.83 (3H, s, OCH$_3$), 4.39, 4.57 (2H, 2xd of d, J=6,15 Hz, NHCH$_2$), 4.65 (1H, m, H$_4$), 6.90 (2H, m, 4-OCH$_3$Ph-H), 7.26–7.50 (7H, m, Ph-H, 4-OCH$_3$Ph-H), 7.60 (1H, m, NH). $\nu_{v=o}$ 1790 cm$^{-1}$. Found: C, 60.9; H, 5.5; N, 7.4%. $C_{19}H_{20}N_2O_2S$ requires: C, 61.3; H, 5.4 N, 7.5%

EXAMPLE 301

Methyl (4-(4-methoxybenzylthio)-2-oxoazetidin-1-yl)acetate

Treatment of 4-(4-methoxybenzylthio)-azetidin-2-one (7 g) with methyl bromoacetate (5.3 g) under the conditions described for Example 29a gave the title compound as a colourless solid, m.p. 45–46° C., (5.9 g, 64%)

EXAMPLE 302

Methyl (4-methoxyphenylthio-2-oxoazetidin-1-yl) acetate

To a solution of 4-(4-methoxyphenylthio)azetidin-2-one (H. Gu et. al., J. Org. Chem., 1990, 55, 5655) (11.6 g, 55 mmol), methyl bromoacetate (9.2 g, 60 mmol) and tetrabutylammonium bromide (1.8 g, 0.56 mmol) in dry THF (300 ml) was added powdered potassium hydroxide (3.4 g, 60 mmol). The resulting mixture was stirred for two hours at room temperature before water (100 ml) was added. The solution was extracted with ethyl acetate (3×150 ml portions) and the combined extracts dried (MgSO$_4$) and evaporated. The residue was purified by flash chromatography on silica gel eluted with ethyl acetate/hexane (1:1→2:1) to give the product as a solid m.p. 101–103° C., 58% yield $^1$H NMR δ (CDCl$_3$) 2.80(1H, dd, J=2.2,15 Hz H$_{3a}$), 3.34 (1H, dd, J=5,15 Hz, H$_{3b}$), 3.72 (3H, s, OCH$_3$), 3.77,4.29 (each 1H, d, J=18.00 Hz, NCH$_2$), 3.80 (3H, s, SCH$_3$), 5.07 (1H, m, H$_4$), 6.87 (2H, d, J=10 Hz, 2,6Ph-H), 7.35 (2H, d, J=10 Hz, 3,5Ph-H).

EXAMPLE 303

Methyl (4-phenylthio-2-oxoazetidin-1-yl)acetate

Treatment of 4-phenylthioazetidin-2-one (Iwata-Reuyl et. al., J. Nat. Prod., 1993, 56(8), 1373) (8 g) with methyl bromoacetate (7.5 g) under the conditions described for Example 1b gave the title compound as a colourless oil (6 g, 53% yield). $^1$H NMR δ (CDCl$_3$) 2.87 (1H, dd, H$_{3a}$), 3.42 (1H, dd, H$_{3b}$), 3.70 (3H, s, CH$_3$), 3.75, 4.29 (each 1H, d, NCH$_2$), 5.22, (1H, dd, H$_4$), 7.26–7.46 (5H, m, Ph-H).

EXAMPLE 304

Methyl [(3S,4R)-4-benzylthio-3-chloro-2-oxoxazetidin-1-yl)acetate a. Method (6S)-chloropenicillanate 1-oxide A solution of methyl (6S)-chloropenicillanate (13.34 g, 0.0534 mol) (Tet.Lett. No.11, p1205–1210, 1966) in dichloromethane (200 ml) was cooled to –70° C. and treated with a solution of 3-chloroperoxybenzoic acid (16.76 g, 0.0534 mol) in dichloromethane (400 ml) over 1 hour maintaining temperature at –70° C. The cooling bath was removed and the reaction was stirred for 1.5 hr. A solution of 3-chloroperoxybenzoic acid (0.5 g) in dichloromethane (100 ml) was added and stirred for 30 minutes. The reaction mixture was washed successively with 10% aq. sodium sulphite, sat. NaHCO$_3$, water, dried (MgSO$_4$) and evaporated. Purification by flash chomatography (silica, pet.ether-ethyl acetate) gave the title compound as a colourless oil, 14.1 g (99%).

b. Methyl 2-[(3S,4R)-4-acetylthio-3-chloro-2-oxoazetidin-1-yl]-3-methylbut-2-enoate A mixture of methyl (6S)-chloropenicillanate 1-oxide (13.94 g, 0.0625 mol), acetic anhydride (24.7 ml, 0.2618 mol) and triisopropyl phosphite (14.25 ml, 0.0578 mol) in benzene (150 ml) was stirred at reflux for 21 hr. The solvents were evaporated and the residue revaporated twice from xylene. The orange oil was diluted with ethyl acetate (150 ml) and treated with triethylamine (0.53 g, 0.00524 mol) and stirred for 1 hr. The reaction was washed successively with 5% aq. citric acid, brine, 5%aq. NaHCO$_3$, brine, dried (MgSO$_4$), and evaporated to a brown oil. Distillation to remove volatile impuities and chromatography (silica, dichloromethane), followed by precipitation from pet. ether gave the title compound as a cream solid, 6.7 g (44%, m.p. 62–63° C.).

c. Methyl [(3S,4R)-4-acetylthio-3-chloro-2-oxo-azetidin-1-yl]acetate

Ozonised oxygen was bubbled through a solution of methyl 2-[(3S,4R)-4-acetylthio-3-chloro-2-oxoazetidin-1-yl]-3-methylbut-2-enoate (7.6 g, 0.026 mol) in ethyl acetate (300 ml) at –65 to –70° C. until a permanent blue colour was obtained. Excess ozone was removed by the passage of oxygen, then trimethyl phosphite (30.7 ml, 0.26 mol) was added dropwise. After 15 minutes the solution was allowed to warm to room temperature and stirred for 19 hr. The solvents were evaporated and the residue reevaporated twice from toluene, then disolved in ethyl acetate (175 ml) and stirred vigourously with a solution of p-toluenesulphonic acid (1.14 g) in water (60 ml). After dilution with water the organic layer was separated and the aqueous layer further extracted with ethyl acetate. The combined organic extracts were washed successively with saturated aq. sodium hydrogen carbonate and brine, dried (MgSO$_4$) and evaporated. Purification by flash chromatography (silica, pet. ether-ethyl acetate) gave the title compound as a colourless solid 3.69 g (56%, m.p. 82–83° C.).

d. Silver (3S,4R)-3-chloro-1-(methoxycarbonylmethyl)-2-oxoazetidine-4-thiolate

A solution of methyl [(3S,4R)-4-acetylthio-3-chloro-2-oxo-azetidin-1-yl]acetate (3.64 g, 0.0145 mol) in methanol (125 ml) was added with stirring in subdued light to a solution of silver nitrate (3.2 g, 0.0188 mol) in methanol (55 ml). Triethylamine (2.6 ml, 0.0187 mol) was then added with ice cooling, and the reaction was stirred for 1 hr at 5–10° C. followed by 40 minutes at room temperature. The mixture was filtered and the solid washed with methanol (x2) and hexane to yield the title compound, 4.19 g (92%).

e. Methyl [(3S,4R)-4-benzylthio-3-chloro-2-oxoazetidin-1-yl)acetate

A solution of silver (3S,4R)-3-chloro-1-(methoxycarbonylmethyl)-2-oxoazetidine-4-thiolate (4.12 g, 0.013 mol) in acetonitrile (125 ml) was treated with benzyl bromide (2.3 ml, 0.0193 mol) under nitrogen and the mixture was stirred in the dark for 18 hr. The mixture was filtered and the filtrate was evaporated. Purification by flash chromatography (silica, pet. ether-ethyl acetate) gave the title compound as a colourless solid, 2.93 g (75%, m.p. 77–79° C.).

$^1$H nmr (CDCl$_3$) 3.57, 4.0 (each 1H, d, J=18 Hz, NCH$_2$), 3.72 (3H, s, CH$_3$), 3.82 (2H, s, SCH$_2$), 4.62 (1H, d, J=1.7 Hz, H$_4$), 4.87 (1H, d, J=1.7 Hz, H$_3$), 7.3 (5H, m, Ph-H)

We claim:

1. A compound of formula (I):

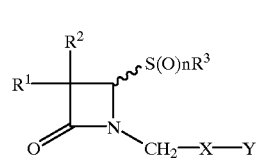

in which:

R$^1$ and R$^2$, which may be the same or different, is each selected from hydrogen, halogen or C$_{(1-8)}$alkyl;

R$^3$ is aryl or arylC$_{(1-4)}$alkyl which said aryls may be optionally substituted by up to five substituents selected from halogen, cyano, $(C_{1-6})$alkyl, $(C_{3-7})$cycloalkyl, $(C_{1-6})$alkoxy, halo$(C_{1-6})$alkyl, hydroxy, amino, mono- or di$(C_{1-6})$alkylamino, acylamino, nitro, carboxy, $(C_{1-6})$alkoxycarbonyl, $(C_{2-6})$alkenyloxycarbonyl, $(C_{1-6})$alkoxycarbonyl$(C_{1-6})$alkyl, $(C_{2-6})$alkenoxycarbonyl$(C_{1-6})$alkyl, $(C_{1-6})$alkylcarbonyloxy, carboxy$(C_{1-6})$alkoxy, $(C_{1-6})$alkoxycarbonyl$(C_{1-6})$alkoxy, $(C_{2-6})$alkenoxycarbonyl$(C_{1-6})$alkoxy, $(C_{1-6})$alkylcarbonyloxy, $(C_{1-6})$alkylthio, $(C_{1-6})$alkylsulphinyl, $(C_{1-6})$alkylsulphonyl, sulphamoyl, mono- and di-$(C_{1-6})$-alkylsulphamoyl, carbamoyl, mono- and di-$(C_{1-6})$alkylcarbamoyl;

X is a direct bond and n is 1 or 2; or

X is a group X'$(CH_2)_m$ in which X' is CO, CONR$^5$, COO, CONR$^5$CO, or CON(H)O in which R$^5$ is hydrogen or $C_{(1-6)}$alkyl and m is 0 or an integer from 1 to 12; or a $C_{(1-12)}$alkylene chain optionally interupted by X' and n is 0, 1 or 2; and Y is an aryl group optionally substituted by up to five substituents selected from halogen, cyano, $(C_{1-6})$alkyl, $(C_{3-7})$cycloalkyl, $(C_{1-6})$alkoxy, halo$(C_{1-6})$alkyl, hydroxy, amino, mono- or di-$(C_{1-6})$alkylamino, acylamino, nitro, carboxy, $(C_{1-6})$alkoxycarbonyl, $(C_{2-6})$alkenyloxycarbonyl, $(C_{1-6})$alkoxycarbonyl$(C_{1-6})$alkyl, $(C_{2-6})$alkenoxycarbonyl$(C_{1-6})$alkyl, $(C_{1-6})$alkylcarbonyloxy, carboxy$(C_{1-6})$alkoxy, $(C_{1-6})$alkoxycarbonyl$(C_{1-6})$alkoxy, $(C_{2-6})$alkenoxycarbonyl$(C_{1-6})$alkoxy, $(C_{1-6})$alkylcarbonyloxy, $(C_{1-6})$alkylthio, $(C_{1-6})$alkylsulphinyl, $(C_{1-6})$alkylsulphonyl, sulphamoyl, mono- and di-$(C_{1-6})$-alkylsulphamoyl, carbamoyl, mono- and di-$(C_{1-6})$alkylcarbamoyl; proved that when R$^3$ and Y are both unsubstituted phenyl and n is 0 or 1, X is not a direct bond.

2. A compound as claimed in claim 1 in which R$^1$ and R$^2$ is each hydrogen.

3. A compound as claimed in claim 1 in which R$^3$ is arylC$_{(1-3)}$alkyl.

4. A compound as claimed in claim 1 in which, in R$^3$, the aryl group is optionally substituted phenyl.

5. A compound as claimed in claim 1 in which R$^3$ is optionally substituted benzyl.

6. A compound as claimed in claim 1 in which R$^3$ is 4-carboxybenzyl or a corresponding $C_{(1-6)}$alkyl or $C_{(2-6)}$alkenyl ester thereof.

7. A compound as claimed in claim 1 in which n is 1.

8. A compound as claimed in claim 1 in which S(O)$_n$R$^3$ is 4-carboxybenzylsulphinyl or a corresponding $C_{(1-6)}$alkyl or $C_{(2-6)}$alkenyl ester thereof.

9. A compound as claimed in claim 1 in which X is CO(CH$_2$)$_m$, CONH(CH$_2$)$_m$, COO(CH$_2$)$_m$, CONHCO(CH$_2$)$_m$, CONHO(CH$_2$)$_m$ and $C_{(1-12)}$alkylene.

10. A compound as claimed in claim 9 in which X is CONH(CH$_2$)$_6$.

11. A compound as claimed in claim 1 in which Y is a benzene ring, optionally substituted by up to three further substituents.

12. A compound as claimed in claim 11 in which Y is phenyl optionally substituted by halo.

13. A compound as claimed in claim 12 in which Y is 4-chloro or 4-fluoro-phenyl.

14. A compound of formula (I) as defined in claim 1 in which the relative configurations at C-4 and the S(O)n moiety, when n=1, are R,S and S,R.

15. A compound as claimed in claim 1 in which the absolute configurations at C-4 and the S(O)n moiety, when n=1, are R and S respectively.

16. A compound of formula (I) as defined in claim 1 selected from:

4-(Benzylthio)-1-(4-phenyl-2-oxobutyl)azetidin-2-one;

(4R,SR/4S,SS) 4-(Benzylsulphinyl)-1-(4-phenyl-2-oxobutyl)azetidin-2-one;

(4R,SS/4S,SR) 4-(Benzylsulphinyl)-1-(4-phenyl-2-oxobutyl)azetidin-2-one;

4-(Benzylsulphonyl)-N-(4-phenyl-2-oxobutyl)azetidin-2-one;

4-(Benzylthio)-1-(2-phenyl-2-oxoethyl)azetidin-2-one;

(4R,SR/4S,SS) 4-(Benzylsulphinyl)-1-(2-phenyl-2-oxoethyl)azetidin-2-one;

(4R,SS/4S,SR) 4-(Benzylsulphinyl)-1-(2-phenyl-2-oxoethyl)azetidin-2-one;

4-(Benzylthio)-1-(9-phenyl-2-oxononyl)azetidin-2-one;

(4R,SR/4S,SS) 4-(Benzylsulphinyl)-1-(9-phenyl-2-oxononyl)azetidin-2-one;

(4R,SS/4S,SR) 4-(Benzylsulphinyl)-1-(9-phenyl-2-oxononyl)azetidin-2-one;

4-(2-Methoxybenzylthio)-N-(4-phenyl-2-oxobutyl)azetidin-2-one;

(4R,SR/4S,SS) 4-(2-Methoxybenzylsulphinyl)-N-(4-phenyl-2-oxobutyl)azetidin-2-one;

(4R,SS/4S,SR) 4-(2-Methoxybenzylsulphinyl)-N-(4-phenyl-2-oxobutyl)azetidin-2-one;

4-(4-Fluorobenzylthio)-N-(4-phenyl-2-oxobutyl)azetidin-2-one;

(4R,SR/4S,SS) 4-(4-Fluorobenzylsulphinyl)-N-(4-phenyl-2-oxobutyl)azetidin-2-one;

(4R,SS/4S,SR) 4-(4-Fluorobenzylsulphinyl)-N-(4-phenyl-2-oxobutyl)azetidin-2-one;

4-(4-methoxybenzylthio)-N-(4-phenyl-2-oxobutyl)azetidin-2-one;

(4R,SR/4S,SS) 4-(4-methoxybenzylsulphinyl)-N-(4-phenyl-2-oxobutyl)azetidin-2-one;

(4R,SS/4S,SR) 4-(4-methoxybenzylsulphinyl)-N-(4-phenyl-2-oxobutyl)azetidin-2-one;

4-(phenethylthio)-N-(4-phenyl-2-oxobutyl)azetidin-2-one;

(4R,SR/4S,SS) 4-(phenethylsulphinyl)-N-(4-phenyl-2-oxobutyl)azetidin-2-one;

(4R,SS/4S,SR) 4-(phenethylsulphinyl)-N-(4-phenyl-2-oxobutyl)azetidin-2-one;

4-(3-Phenylpropylthio)-N-(4-phenyl-2-oxobutyl)azetidin-2-one;

(4R,SR/4S,SS) 4-(3-Phenylpropylsulphinyl)-N-(4-phenyl-2-oxobutyl)azetidin-2-one;

(4R,SS/4S,SR) 4-(3-Phenylpropylsulphinyl)-N-(4-phenyl-2-oxobutyl)azetidin-2-one;

trans 3-Methyl-4-(benzylthio)-1-(4-phenyl-2-oxobutyl)azetidin-2-one;

(4R,SR/4S,SS) trans 3-Methyl-4-(benzylsulphinyl)-1-(4-phenyl-2-oxobutyl)azetidin-2-one;

(4R,SS/4S,SR) trans 3-methyl-4-(benzylsulphinyl)-1-(4-phenyl-2-oxobutyl)azetidin-2-one;

N-(6-phenylhexyl)-(4-benzylthio-2-oxoazetidin-1-yl)acetamide;

(4R,SR/4S,SS) N-(6-phenylhexyl)-(4-benzylsulphinyl-2-oxoazetidin-1-yl)acetamide;

(4R,SS/4S,SR) N-(6-phenylhexyl)-(4-benzylsulphinyl-2-oxoazetidin-1-yl)acetamide;

N-benzyl-(4-benzylthio-2-oxoazetidin-1-yl)acetamide;

(4R,SR/4S,SS) N-benzyl-(4-benzylsulphinyl-2-oxoazetidin-1-yl)acetamide;

(4R,SS/4S,SR) N-benzyl-(4-benzylsulphinyl-2-oxoazetidin-1-yl)acetamide;

N-(4-Phenylbutyl)-(4-benzylthio-2-oxoazetidin-1-yl)acetamide;

(4R,SR/4S,SS) N-(4-Phenylbutyl)-(4-benzylsulphinyl-2-oxoazetidin-1-yl)acetamide;

(4R,SS/4S,SR) N-(4-Phenylbutyl)-(4-benzylsulphinyl-2-oxoazetidin-1-yl)acetamide;

N-(9-Phenylnonyl)-(4-benzylthio-2-oxoazetidin-1-yl)acetamide;

(4R,SR/4S,SS) N-(9-Phenylnonyl)-(4-benzylsulphinyl-2-oxoazetidin-1-yl)acetamide;

(4R,SS/4S,SR) N-(9-Phenylnonyl)-(4-benzylsulphinyl-2-oxoazetidin-1-yl)acetamide;

N-Methyl-N-(6-phenylhexyl)-(4-benzylthio-2-oxoazetidin-1-yl)acetamide;

(4R,SR/4S,SS) N-Methyl-N-(6-phenylhexyl)-(4-benzylsulphinyl-2-oxoazetidin-1-yl)acetamide;

(4R,SS/4S,SR) N-Methyl-N-(6-phenylhexyl)-(4-benzylsulphinyl-2-oxoazetidin-1-yl)acetamide;

N-[6-(3,5-di-tert-butyl-4-hydroxyphenyl)hexyl]-(4-benzylthio-2-oxoazetidin-1-yl)acetamide;

(4R,SS/4S,SR) N-[6-(3,5-Di-tert-butyl-4-hydroxyphenyl)hexyl]-(4-benzylsulphinyl-2-oxoazetidin-1-yl)acetamide;

N-6-(4-methoxyphenyl)hexyl-(4-benzylthio-2-oxoazetidin-1-yl)acetamide;

(4R,SR/4S,SS) N-6-(4-methoxyphenyl)hexyl-(4-benzylsulphinyl-2-oxoazetidin-1-yl)acetamide;

(4R,SS/4S,SR) N-6-(4-methoxyphenyl)hexyl-(4-benzylsulphinyl-2-oxoazetidin-1-yl)acetamide;

N-(6-(4-chlorophenyl)hexyl)-(4-benzylthio-2-oxoazetidin-1-yl)acetamide;

(4R,SR/4S,SS) N-(6-(4-chlorophenyl)hexyl)-(4-benzylsulphinyl-2-oxoazetidin-1-yl)acetamide;

(4R,SS/4S,SR) N-(6-(4-chlorophenyl)hexyl)-(4-benzylsulphinyl-2-oxoazetidin-1-yl)acetamide;

N-(6-(3,5-dichlorophenyl)hexyl)-(4-benzylthio-2-oxoazetidin-1-yl)-acetamide;

(4R,SR/4S,SS) N-(6-(3,5-dichlorophenyl)hexyl)-(4-benzylsulphinyl-2-oxoazetidin-1-yl)acetamide;

(4R,SS/4S,SR) N-(6-(3,5-dichlorophenyl)hexyl)-(4-benzylsulphinyl-2-oxoazetidin-1-yl)acetamide;

N-(6-(3-chlorophenyl)hexyl)-(4-benzylthio-2-oxoazetidin-1-yl)-acetamide;

(4R,SR/4S,SS) N-(6-(3-chlorophenyl)hexyl)-(4-benzylsulphinyl-2-oxoazetidin-1-yl)acetamide;

(4R,SS/4S,SR) N-(6-(3-chlorophenyl)hexyl)-(4-benzylsulphinyl-2-oxoazetidin-1-yl)acetamide;

N-6-(4-hydroxyphenyl)hexyl-(4-benzylthio-2-oxoazetidin-1-yl)-acetamide;

(4R,SR/4S,SS) N-6-(4-hydroxyphenyl)hexyl-(4-benzylsulphinyl-2-oxoazetidin-1-yl)acetamide;

(4R,SS/4S,SR) N-6-(4-hydroxyphenyl)hexyl-(4-benzylsulphinyl-2-oxoazetidin-1-yl)acetamide;

N-(6-Phenylhexyl)-(4-(4-ethoxycarbonyl)benzylthio-2-oxoazetidin-1-yl)acetamide;

(4R,SS/4S,SR) N-(6-Phenylhexyl)-(4-(4-ethoxycarbonyl)benzylsulphinyl-2-oxoazetidin-1-yl)acetamide;

N-(6-phenylhex-1-yl)-4-(4-chlorobenzylthio)-2-oxoazetidin-1-ylacetamide;

(4R,SR/4S,SS) N-(6-phenylhex-1-yl)-4-(4-chlorobenzylsulphinyl)-2-oxoazetidin-1-ylacetamide;

(4R,SS/4S,SR) N-(6-phenylhex-1-yl)-4-(4-chlorobenzylsulphinyl)-2-oxoazetidin-1-ylacetamide;

trans N-(6-Phenylhexyl)-(4-benzylthio-3-methyl-2-oxoazetidin-1-yl)acetamide;

trans N-(6-Phenylhexyl)-(4-benzylsulphinyl-3-methyl-2-oxoazetidin-1-yl)acetamide;

N-(6-phenylhexyl)-(4-benzylsulphonyl-2-oxoazetidin-1-yl)acetamide;

N-(6-(3,5-dichlorophenyl)hexyl)-(4-benzylsulphonyl-2-oxoazetidin-1-yl)acetamide;

N-(6-(3-chlorophenyl)hexyl)-(4-benzylsulphinyl-2-oxoazetidin-1-yl)acetamide;

4-(Benzylthio)-1-(3-phenylpropyl)azetidin-2-one;

(4R,SR/4S,SS) 4-Benzylsulphinyl-1-(3-phenylpropyl)azetidin-2-one;

(4R,SS/4S,SR) 4-Benzylsulphinyl-1-(3-phenylpropyl)azetidin-2-one;

4-Benzylthio-1-(2-phenethyl)azetidin-2-one;

(4R,SR/4S,SS) 4-Benzylsulphinyl-1-(2-phenethyl)azetidin-2-one;

(4R,SS/4S,SR) 4-Benzylsulphinyl-1-(2-phenethyl)azetidin-2-one 4-(Benzylthio)-1-(4-phenylbutyl)azetidin-2-one;

(4R,SS/4S,SR) 4-Benzylsulphinyl-1-(4-phenylbutyl)azetidin-2-one;

p-Methoxybenzyl [(3S, 4R)-4-benzylthio-3-bromo-2-oxoazetidin-1-yl]acetate;

(3S,4R)-N-(6-phenylhexyl)-1-(4-benzylthio-3-bromo-2-oxoazetidin-1-yl)acetamide;

(3S,4R,SR)-N-(6-phenylhexyl)-4-benzylsulphinyl-3-bromo-2-oxoazetidin-1-yl acetamide;

(3S,4R,SS)-N-(6-phenylhexyl)-4-benzylsulphinyl-3-bromo-2-oxoazetidin-1-ylacetamide;

(4R,SS/4R,SR)-N-(6-phenylhexyl)-4-benzylsulphinyl-2-oxoazetidin-1-yl acetamide;

(3S,4R)-N-(6-phenylhexyl)-1-(4-benzylthio-3-bromo-2-oxoazetidin-1-yl)acetamide;

(4R,SS)-N-(6-(4-chlorophenyl)hexyl)-(4-benzylsulphinyl-2-oxoazetidin-1-yl)acetamide;

N-[6-(4-Fluorophenyl)hexyl]-4-(4-methoxybenzylthio)-2-oxoazetidin-1-ylacetamide;

N-(6-(2,4-Difluorophenyl)hexyl)-(4-benzylthio-2-oxoazetidin-1-yl)acetamide;

N-[6-(4-Chlorophenyl)hexyl]-4-(4-methoxybenzylthio)-2-oxoazetidin-1-ylacetamide;

N-(6-(3,4-Difluorophenyl)hexyl)-(4-benzylthio-2-oxoazetidin-1-yl)acetamide;

N-(7-phenylhept-1yl)-4-benzylthio-2-oxoazetidin-1-yl acetamide;

N-(6-[4-chlorophenyl]hex-1-yl)-(4-methoxycarbonylbenzylthio)-2-oxoazetidin-1-yl acetamide;

N-(5-phenylpentyl)-4-benzylthio-2-oxo-azetidinyl-1-yl acetamide;

N-(6-(4-Bromophenyl)hexyl)-4-benzylthio-2-oxoazetidin-1-ylacetamide;

N-(6-(4-Fluorophenyl)hexyl)-4-benzylthio-2-oxoazetidin-1-ylacetamide;

N-[5-(4-chlorophenyl)pentyl]-4-benzylthio-2-oxo-azetidin-1-yl acetamide;

N-[6-(2-Chlorophenyl)hexyl]-4-benzylthio-2-oxo-azetidin-1yl acetamide;

N-(6-[4-chlorophenyl]hex-1-yl)-(4-allyloxycarbonylbenzylthio)-2-oxoazetidin-1-yl-acetamide;
N-[6-(4-methylphenyl)-hexyl]-[4-benzylsulphinyl-2-oxo-azetidin-1-yl]-acetamide;
6-Phenylhexyl (4-benzylthio-2-oxo-azetidin-1-yl)acetate;
6-(4-Chlorophenyl)hexyl-[4-benzylthio-2-oxo-azetidin-1yl] acetate;
1-(9-Phenylnonyl)-4-benzylthio-2-oxoazetidine;
(4R,SR/4S,SS)-N-[6-(4-Fluorophenyl)hexyl]-4-(4-methoxybenzylsulphinyl)-2-oxoazetidin-1-ylacetamide;
(4R,SS/4S,SR)-N-[6-(4-Fluorophenyl)hexyl]-4-(4-methoxybenzylsulphinyl)-2-oxoazetidin-1-ylacetamide;
(4R,SR/4S,SS)-N-(6-(2,4-Difluorophenyl)hexyl)-(4-benzylsulphinyl-2-oxoazetidin-1-yl)acetamide;
N-(6-(2,4-Difluorophenyl)hexyl)-(4-benzylsulphinyl-2-oxoazetidin-1-yl)acetamide;
(4R,SR/4S,SS)-N-[6-(4-Chlorophenyl)hexyl]-4-(4-methoxybenzylsulphinyl)-2-oxoazetidin-1-ylacetamide;
(4R,SS/4S,SR)-N-[6-(4-Chlorophenyl)hexyl]-4-(4-methoxybenzylsulphinyl)-2-oxoazetidin-1-ylacetamide;
(4R,SR/4S,SS)-N-(6-(3,4-Difluorophenyl)hexyl)-(4-benzylsulphinyl-2-oxoazetidin-1-yl)acetamide;
(4R,SS/4S,SR)-N-(6-{3,4-Difluorophenyl}hexyl)-(4-benzylsulphinyl-2-oxoazetidin-1-yl)acetamide;
(4R,SR/4S,SS)-N-(7-phenylhept-1-yl)-4-benzylsulphinyl-2-oxoazetidin-1-yl acetamide;
(4R,SR/4S,SR)-N-(7-phenylhept-1-yl)-4-benzylsulphinyl-2-oxoazetidin-1-yl acetamide;
(4R,SR/4S,SS)-N-(6-[4-chlorophenyl]hex-1-yl)-(4-methoxycarbonylbenzylsulphinyl)-2-oxoazetidin-1-yl acetamide;
(4R,SS/4S,SR)-N-(6-[4-chlorophenyl]hex-1-yl)-(4-methoxycarbonylbenzyl sulphinyl)-2-oxoazetidin-1-yl acetamide;
(4R,SR/4S,SS)-N-(6-phenylhex-1-yl)-(4-ethoxycarbonylbenzylsulphinyl)-2-oxoazetidin-1-yl acetamide;
(4R,SS/4S,SR)-N-(6-[4-chlorophenyl]hex-1-yl)-(4-allyloxycarbonyl-benzylsulphinyl)-2-oxoazetidin-1-yl acetamide;
N-(5-phenylpentyl)-4-benzylsulphinyl-2-oxo-azetidinyl-1-yl acetamide;
(4R,SR/4S,SS)-N-(5-(4-Chlorophenyl)pentyl)-4-benzylsulphinyl-2-oxo-azetidin-1yl acetamide;
(4R,SS/4S,SR)-N-(5-(4-Chlorophenyl)pentyl)-4-benzylsulphinyl-2-oxo-azetidin-1yl acetamide;
(4R,SR/4S,SS)-N-[5-(2-Chlorophenyl)hexyl]-4-benzylsulphinyl-2-oxo-azetin-1yl acetamide;
N-[5-(2-Chlorophenyl)hexyl]-4-benzylsulphinyl-2-oxo-azetidin-1yl acetamide;
(4R,SR/4S,SS)-N-(6-(4-Bromophenyl)hexyl)-4-benzylsulphinyl-2-oxoazetidin-1-ylacetamide;
(4R,SS/4S,SR)-N-(6-(4-Bromophenyl)hexyl)-4-benzylsulphinyl-2-oxoazetidin-1-ylacetamide;
(4R,SR/4S,SS)-N-(6-(4-Fluorophenyl)hexyl)-4-benzylsulphinyl-2-oxoazetidin-1-ylacetamide;
(4R,SS/4S,SR)-N-(6-(4-Fluorophenyl)hexyl)-4-benzylsulphinyl-2-oxoazetidin-1-ylacetamide;
(4R,SR/4S,SS)-6-Phenylhexyl (4-benzylsulphinyl-2-oxoazetidin-1-yl)acetate;
(4R,SS/4S,SR)-6-Phenylhexyl (4-benzylsulphinyl-2-oxoazetidin-1-yl)acetate;
6-(4-Chlorophenyl)hexyl-(4-benzylsulphinyl-2-oxoazetidin-1-yl) acetate;
(4R,SR/4S,SS)-1-(9-Phenylnonyl)-4-benzylsulphinyl-2-oxoazetidine;
(4R,SS/4S,SR)-1-(9-Phenylnonyl)-4-benzylsulphinyl-2-oxoazetidine;
N-[6-(4-Methylphenyl)-hexyl]-[4-benzylsulphinyl-2-oxo-azetidin-1-yl]-acetamide;
N-[6-(4-Methylphenyl)-hexyl]-[4-benzylsulphinyl-2-oxo-azetidin-1-yl]-acetamide;
N-(6-(4-chlorophenyl)hex-1-yl)-((4-carboxybenzylsulphinyl)-2-oxoazetidin-1-yl) acetamide;
N-[6-(4-Fluorophenyl)hexyl]-4-(4-methoxybenzylsulphonyl)-2-oxoazetidin-1-ylacetamide;
N-(6-(2,4-Difluorophenyl)hexyl)-(4-benzylsulphonyl-2-oxoazetidin-1-yl)acetamide;
N-[6-(4-Chlorophenyl)hexyl]-4-(4-methoxybenzylsulphonyl)-2-oxoazetidin-1-ylacetamide;
N-(6-(3,4-Difluorophenyl)hexyl)-(4-benzylsulphonyl-2-oxoazetidin-1yl)acetamide;
N-(7-phenylhept-1-yl)-4-benzylsulphonyl-2-oxoazetidin-1-yl acetamide;
N-[6-(4-Chlorophenyl)hexyl]-(4-(4-carboxybenzylsulphonyl)-2-oxo-azetidin-1yl) acetamide;
N-[5-(4-Chlorophenyl)pentyl]-4-benzylsulphonyl-2-oxo-azetidin-1yl acetamide;
N-[5-(2-Chlorophenyl)hexyl]-4-benzylsulphonyl-2-oxo-azetidin-1yl acetamide;
N-(6-(4-Fluorophenyl)hexyl)-4-benzylsulphonyl-2-oxoazetidin-1-ylacetamide;
6-Phenylhexyl-[4-benzylsulphonyl-2-oxo-azetidin-1yl] acetate;
6-(4-Chlorophenyl)hexyl-(4-benzylsulphonyl-2-oxoazetidin-1-yl] acetate;
1-(9-Phenylnonyl)-4-benzylsulphonyl-2-oxoazetidine;
N-[6-(4-Methylphenyl)-hexyl]-[4-benzylsulphonyl-2-oxo-azetidin-1-yl]-acetamide;
N-(6-Phenylhexanoyl)-(4-benzylthio-2-oxoazetidin-yl) acetamide;
N-(6-Phenylhexanoyl)-(4-benzylsulphinyl-2-oxoazetidin-yl)acetamide;
N-(5-Phenylpentyloxy)-(4-benzylthio-2-oxoazetidin-1-yl)acetamide;
(4R,SR/4S,SS)-N-(5-Phenylpentyloxy)-(4-benzylsulphinyl-2-oxoazetidin-1-yl)acatamide;
(4R,SS/4S,SR)-N-(5-Phenylpentyloxy)-(4-benzylsulphinyl-2-oxoazetidin-1-yl)acatamide;
4R-N-(6-(4-Chlorophenyl)hexyl)-(4-benzythio-2-oxoazetidin-1-yl)acetamide;
4S-N-(6-{4-Chlorophenyl}hexyl)-(4-benzythio-2-oxoazetidin-1-yl)acetamide;
(4R,SR)-N-(6-(4-Chlorophenyl)hexyl)-(4-benzysulphinyl-2-oxoazetidin-1-yl)acetamide;
(4S,SS)-N-(6-(4-Chlorophenyl)hexyl)-(4-benzysulphinyl-2-oxoazetidin-1-yl)acetamide;

(4R,SS)-N-(6-(4-Chlorophenyl)hexyl)-(4-benzylsulphinyl-2-oxoazetidin-1-yl)acetamide;
(4R,SS)-N-(6-(4-Chlorophenyl)hexyl)-(4-benzylsulphinyl-2-oxoazetidin-1-yl)acetamide;
(4R,SS)-N-(6-(4-Chlorophenyl)hexyl)-(4-benzylsulphinyl-2-oxoazetidin-1-yl)acetamide;
(4R,SS)-N-(6-(4-Chlorophenyl)hexyl)-(4-benzylsulphinyl-2-oxoazetidin-1yl)acetamide;
(4S,SR)-N-(6-(4-Chlorophenyl)hexyl)-(4-benzysulphinyl-2-oxoazetidin-1-yl)acetamide;
4R-N-(6-(4-Chlorophenyl)hexyl)-(4-benzysulphonyl-2-oxoazetidin-1-yl)acetamide;
4S-N-(6-(4-Chlorophenyl)hexyl)-(4-benzysulphonyl-2-oxoazetidin-1-yl)acetamide;
4R-(6-Phenylhexyl)-(4-benzylthio-2-oxoazetidin-1-yl)acetamide;
(4R,SR)-N-(6-Phenylhexyl)-(4-benzylsulphinyl-2-oxoazetidin-1-yl)acetamide;
N-(6-{4-Fluorophenyl}hexyl)-4-(4-allyloxycarbonylbenzylthio-2-oxoazetidin-1-yl)acetamide;
(4R,SR/4S,SS)-N-(6-{4-Fluorophenyl}hexyl)-4-(4-allyloxycarbonylbenzylsulphinyl-2-oxoazetidin-1-yl)acetamide;
(4R,SS/4S,SR)-N-(6-{4-Fluorophenyl}hexyl)-4-(4-allyloxycarbonylbenzylsulphinyl-2-oxoazetidin-1-yl);
(4R,SS/4S,SR)-N-(6-{4-Fluorophenyl}hexyl)-4-(4-carboxybenzylsulphinyl-2-oxoazetidin-1-yl)acetamide;
(4R,SS/4S,SR)-N-(6-{4-Fluorophenyl}hexyl)-4-(4-isopropyloxycarbonylbenzylsulphinyl-2-oxoazetidin-1-yl)acetamide;
(4R,SS/4S,SR)-N-(6-{4-Fluorophenyl}hexyl)-4-(4-propyloxycarbonylbenzylsulphinyl-2-oxoazetidin-1-yl)acetamide;
(4R,SS/4S,SR)-N-[6-(4-Fluorophenyl)hexyl]-[4-(4-ethyloxycarbonylbenzyl)sulphinyl-2-oxo-azetidin-1-yl]-acetamide;
N-(6-[4-Fluorophenyl]hex-1-yl)-4-carboxybenzylthio)-2-oxoazetidin-1-yl acetamide;
N-(6-[4-Fluorophenyl]hex-1-yl)-(4-methylcarboxybenzylthio)-2-oxoazetidin-1-yl acetamide;
(4R,SS/4S,R)-N-[6-(4-Fluorophenyl)hexyl]-[4-(4-methyloxycarbonylbenzyl)sulphinyl-2-oxo-azetidin-1-yl]-acetamide;
(4R,SS/4S,SR)-N-(6-{4-Chlorophenyl}hexyl)-4-(4-isopropyloxycarbonylbenzylsulphinyl-2-oxoazetidin-1-yl)acetamide;
(4R,SS/4S,SR)-N-(6-{4-Chlorophenyl}hexyl)-4-(4-propyloxycarbonylbenzylsulphinyl-2-oxoazetidin-1-yl)acetamide;
(4R,SS/4S,SR)-N-(6-{4-Chlorophenyl}hexyl)-4-(4-ethyloxycarbonylbenzylsulphinyl-2-oxoazetidin-1-yl)acetamide;
N-[6-(4-Fluorophenyl)hexyl]-[4-(4-(allyloxycarbonylmethyl)benzyl)thio-2-oxo-azetidin-1-yl]-acetamide;
N-[6-(4-Fluorophenyl)hexyl]-[4-(4-(allyloxycarbonylmethyl)benzyl)sulphinyl-2-oxo-azetidin-1-yl]-acetamide;
N-[6-(4-Fluorophenyl)hexyl]-[4-(4-(allyloxycarbonylmethyl)benzyl)sulphinyl-2-oxo-azetidin-1-yl]-acetamide;
N-[6-(4-Fluorophenyl)hexyl]-[4-(4-(carboxymethyl)benzyl)thio-2-oxo-azetidin-1-yl]-acetamide;
N-[6-(4-Fluorophenyl)hexyl]-[4-(4-(carboxymethyl)benzyl)sulphinyl-2-oxo-azetidin-1-yl]-acetamide;
N-[6-(4-Fluorophenyl)hexyl]-[4-(4-(carboxymethyl)benzyl)sulphinyl-2-oxo-azetidin-1-yl]-acetamide;
N-2,4-Dichlorobenzyl-(4-benzylthio-2-oxoazetidin-1-yl)acetamide;
(4R,SR/4S,SS)-N-2,4-Dichlorobenzyl-(4-benzylsulphinyl-2-oxoazetidin-1-yl)acetamide;
(4R,SS/4S,SR)-N-2,4-Dichlorobenzyl-(4-benzylsulphinyl-2-oxoazetidin-1-yl)acetamide;
N-2,4-Dichlorobenzyl-(4-benzylsulphonyl-2-oxoazetidin-1-yl)acetamide;
N-3,4-Dichlorobenzyl-(4-benzylthio-2-oxoazetidin-1-yl)acetamide;
(4R,SR/4S,SS)-N-3,4-Dichlorobenzyl-(4-benzylsulphinyl-2-oxoazetidin-1-yl)acetamide;
(4R,SS/4S,SR)-N-3,4-Dichlorobenzyl-(4-benzylsulphinyl-2-oxoazetidin-1-yl)acetamide;
N-3,4-Dichlorobenzyl-(4-benzylsulphonyl-2-oxoazetidin-1-yl)acetamide;
(3S,4R)-N-(6-{4-Fluorophenyl}hexyl)-(3-chloro-4-benzylthio-2-oxoazetidin-1-yl)acetamide;
(3S,4R,SR)-N-(6-{4-Fluorophenyl}hexyl)-(3-chloro-4-benzylsulphinyl-2-oxoazetidin-1-yl)acetamide;
(SS,3S,4R)-N-(6-{4-Fluorophenyl}hexyl)-(3-chloro-4-benzylsulphinyl-2-oxoazetidin-1-yl)acetamide;
(3S,4R)-N-(6-(4-Fluorophenyl)hexyl)-4-benzylthio-3-((R)-hydroxyethyl)-2-oxoazetidin-1-ylacetamide;
(3S,4R)-N-(6-(4-Fluorophenyl)hexyl)-4-benzylsulphinyl-3-((R)-hydroxyethyl)-2-oxoazetidin-1-ylacetamide;
N-(6-phenylhexyl)-(4-(4-methoxyphenylthio)-2-oxoazetidin-1-yl)acetamide;
(4R,SR/4S,SS) N-(6-phenylhexyl)-(4-(4-methoxyphenyl)sulfinyl)-2-oxoazetidin-1-yl)acetamide;
(4R,SS/4S,SR)-N-(6-phenylhexyl)-(4-(4-methoxyphenyl)sulfinyl)-2-oxoazetidin-1-yl)acetamide;
N-(6-phenylhexyl)-(4-(4-methoxyphenyl)sulfonyl)-2-oxoazetidin-1-yl)acetamide;
N-(6-phenylhexyl)-(4-(3,4-dimethoxyphenylthio)-2-oxoazetidin-1-yl)acetamide
(4R,SS/4S,SR)-N-(6-phenylhexyl)-(4-(3,4-dimethoxyphenylsulfinyl)-2-oxoazetidin-1-yl)acetamide;
(4R,SR/4S,SS) N-(6-phenylhexyl)-(4-(3,4-dimethoxyphenylsulfinyl)-2-oxoazetidin-1-yl)acetamide;
N-(6-phenylhexyl)-(4-(4-chlorophenylthio)-2-oxoazetidin-1-yl)acetamide;
4-(Phenylthio)-N-(4-phenyl-2-oxobutyl)azetidin-2-one;
(4S)-4-(Phenylthio)-N-(4-phenyl-2-oxobutyl)azetidin-2-one;
(4R)-4-(Phenylthio)-N-(4-phenyl-2-oxobutyl)azetidin-2-one;
4-(2-Methoxyphenylthio)-N-(4-phenyl-2-oxobutyl)azetidin-2-one;
4-(3,4-dimethoxyphenylthio)-N-(4-phenyl-2-oxobutyl)azetidin-2-one;
4-(3-methoxyphenylthio)-N-(4-phenyl-2-oxobutyl)azetidin-2-one;

4-(4-methoxyphenylthio)-N-(4-phenyl-2-oxobutyl) azetidin-2-one;

(4R,SR/4S,SS) 4-(Phenylsulphinyl)-N-(4-phenyl-2-oxobutyl)azetidin-2-one;

(4R,SS/4S,SR)-4-(Phenylsulphinyl)-N-(4-phenyl-2-oxobutyl)azetidin-2-one;

(4R,SR)-4-(Phenylsulphinyl)-N-(4-phenyl-2-oxobutyl) azetidin-2-one;

(4R,SS)-4-(Phenylsulphinyl)-N-(4-phenyl-2-oxobutyl) azetidin-2-one;

(4R,SR/4S,SS) 4-(2-Methoxyphenylsulphinyl)-N-(4-phenyl-2-oxobutyl)azetidin-2-one;

(4R,SS/4S,SR)-4-(2-Methoxyphenylsulphinyl)-N-(4-phenyl-2-oxobutyl)azetidin-2-one;

(4R,SS/4S,SR)-4-(3,4-dimethoxyphenylsulphinyl)-N-(4-phenyl-2-oxobutyl)azetidin-2-one;

(4R,SR/4S,SS) 4-(3-methoxyphenylsulphinyl)-N-(4-phenyl-2-oxobutyl)azetidin-2-one;

(4R,SS/4S,SR)-4-(3-methoxyphenylsulphinyl)-N-(4-phenyl-2-oxobutyl)azetidin-2-one;

(4R,SR/4S,SS) 4-(4-methoxyphenylsulphinyl)-N-(4-phenyl-2-oxobutyl)azetidin-2-one;

(4R,SS/4S,SR)-4-(4-methoxyphenylsulphinyl)-N-(4-phenyl-2-oxobutyl)azetidin-2-one;

4-(Phenylsulphonyl)-N-(4-phenyl-2-oxobutyl)azetidin-2-one;

4-(2-Methoxyphenylsulphonyl)-N-(4-phenyl-2-oxobutyl) azetidin-2-one;

N-[6-(4-Chlorophenyl)hexyl]-4-(4-methylphenylthio)-2-oxoazetidin-1-ylacetamide;

(4R,SR/4S,SS)-N-[6-(4-chlorophenyl)hexyl]-4-(4-methylphenyl)sulfinyl-2-oxo-azetidinyl-1-yl acetamide;

(4R,SS/4S,SR)-N-[6-(4-chlorophenyl)hexyl]-4-(4-methylphenyl)sulfinyl-2-oxo-azetidinyl-1-yl acetamide;

N-[6-(4-chlorophenyl)hexyl]-4-(4-methylphenyl) sulfonyl-2-oxo-azetidinyl-1-yl acetamide;

(+/−)-N-[6-(4-Chlorophenyl)hexyl]-4-phenylthio-2-oxoazetidin-1-ylacetamide hydrate;

(−)-N-[6-(4-Chlorophenyl)hexyl]-4-phenylthio-2-oxoazetidin-1-ylacetamide hydrate;

(+)-N-[6-(4-Chlorophenyl)hexyl]-4-phenylthio-2-oxoazetidin-1-ylacetamide hydrate;

(4R,SR/4S,SS)-N-[6-(4-Chlorophenyl)hexyl]-4-phenylsulfinyl-2-oxoazetidin-1-ylacetamide;

(4R,SS/4S,SR)-N-[6-(4-Chlorophenyl)hexyl]-4-phenylsulfinyl-2-oxoazetidin-1-ylacetamide;

(−)-(4R,SR or 4S,SS)-N-[6-(4-Chlorophenyl)hexyl]-4-phenylsulfinyl-2-oxoazetidin-1-ylacetamide;

(+)-(4R,SS or 4S,SR)-N-[6-(4-Chlorophenyl)hexyl]-4-phenylsulfinyl-2-oxoazetidin-1-ylacetamide;

(+)-(4R,SS or 4S,SR)-N-[6-(4-Chlorophenyl)hexyl]-4-phenylsulfinyl-2-oxoazetidin-1-ylacetamide;

(−)-(4R,SR or 4S,SS)-N-[6-(4-Chlorophenyl)hexyl]-4-phenylsulfinyl-2-oxoazetidin-1-ylacetamide;

N-[6-(4-Chlorophenyl)hexyl]-4-phenylsulfonyl-2-oxoazetidin-1-ylacetamide;

(−)-N-[6-(4-Chlorophenyl)hexyl]-4-phenylsulfonyl-2-oxoazetidin-1-ylacetamide;

(+)-N-[6-(4-Chlorophenyl)hexyl]-4-phenylsulfonyl-2-oxoazetidin-1-ylacetamide;

N-[6-(4-Chlorophenyl)hexyl]-4-(4-methoxyphenylthio)-2-oxoazetidin-1-ylacetamide;

(4R,SR/4S,SS)-N-[6-(4-Chlorophenyl)hexyl]-4-(4-methoxyphenylsulfinyl)-2-oxoazetidin-1-ylacetamide;

(4R,SS/4S,SR)-N-[6-(4-Chlorophenyl)hexyl]-4-(4-methoxyphenylsulfinyl)-2-oxoazetidin-1-ylacetamide;

N-[6-(4-Chlorophenyl)hexyl]-4-(4-methoxyphenylsulfonyl)-2-oxoazetidin-1-ylacetamide N-Benzyl-[4-(4-methoxyphenylthio)-2-oxoazetidin-1-yl]acetamide;

(4R,SR/4S,SS)-N-Benzyl-[4-(4-methoxyphenylsulphinyl)-2-oxoazetidin-1-yl]acetamide; and (4R,SS/4S,SR)-N-Benzyl-[4-(4-methoxyphenylsulphinyl)-2-oxoazetidin-1-yl]acetamide;

in which 3R or 3S describes the absolute configuration at the C3 chiral centre in the azetidinone, 4R or 4S describes the absolute configuration at the C4 chiral centre in the azetidinone, and SR or SS describes the absolute configuration at sulfoxide chiral centre, the "S" refers to sulphur; and "/" denotes "and" and rather than "or".

17. A pharmaceutical composition comprising a compound of formula (I) as defined in claim 1 and a pharmaceutically acceptable carrier.

18. A method of treating atheroscelorsis that comprises administering an anti-atherosclerotic effective amount of a compound of formula (I) as defined in claim 1 to a patient in need thereof.

19. A compound of formula (VII)

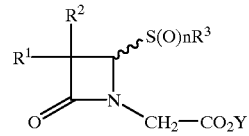

(VII)

in which:

Y is $(C_{1-6})$alkyl; and n, $R^1$, $R^2$ and $R^3$ are as defined in claim 1.

20. A compound of formula (VII) as defined in claim 19 selected from:

Methyl-(4-benzylthio-2-oxoazetidin-1-yl)acetate;

Methyl (4-(4-methoxybenzylthio)-2-oxoazetidin-1-yl) acetate;

Methyl (4-methoxyphenylthio-2-oxoazetidin-1-yl) acetate; and

Methyl (4-phenylthio-2-oxoazetidin-1-yl)acetate.

21. A process for preparing a compound of formula (I) as defined in claim 1 which process comprises:

(i) treating an azetidinone of formula (II):

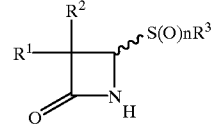

(II)

in which:

n, $R^1$, $R^2$ and $R^3$ are as hereinbefore defined;

with an alkylating agent of the formula (III):

$$ZCH_2XY \quad (III)$$

in which Z is a leaving group; and
X and Y are as hereinbefore defined;
under alkylating conditions;

(ii) when X denotes a group $CONR^5(CH_2)_m$ or $CONHO(CH_2)_m$, treating an acid of the formula (IV):

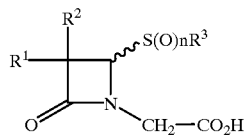
(IV)

in which:
n, $R^1$, $R^2$ and $R^3$ are as hereinbefore defined;
with an amine of the formula (V):

$$NHR_5(CH_2)_mY \quad (V)$$

or a hydroxylamine of the formula (VI):

$$NH_2O(CH_2)_mY \quad (VI)$$

in which Y and m are as hereinbefore defined,
under amide or hydroxamate bond forming conditions;

(III) when X denotes a group $COO(CH_2)_m$, treating a compound of formula (IV) as hereinbefore defined with an alcohol $Y(CH_2)_mOH$ or an activated derivative thereof under ester forming conditions; or (iv) treating a compound of formula (VIII):

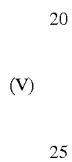
(VIII)

in which $R^1$, $R^2$, $R^3$, X and Y are as hereinbefore defined;
with an alkylating agent of the formula (IX):

$$R^3Z \quad (IX)$$

in which $R^3$ and Z are as hereinbefore defined;
under alkylating conditions.

* * * * *